US007439251B2

(12) United States Patent
Fisher et al.

(10) Patent No.: US 7,439,251 B2
(45) Date of Patent: Oct. 21, 2008

(54) METHODS AND COMPOSITIONS FOR TREATMENT OF CENTRAL AND PERIPHERAL NERVOUS SYSTEM DISORDERS AND NOVEL COMPOUNDS USEFUL THEREFOR

(75) Inventors: Abraham Fisher, Holon (IL); Nira Bar-Ner, Rishon de Zion (IL); Yishai Karton, Ness Ziona (IL)

(73) Assignee: Israel Institute for Biological Research, Ness Ziona (IL)

( * ) Notice: Subject to any disclaimer, the term of this patent is extended or adjusted under 35 U.S.C. 154(b) by 316 days.

(21) Appl. No.: 10/512,673

(22) PCT Filed: May 1, 2003

(86) PCT No.: PCT/IL03/00357

§ 371 (c)(1),
(2), (4) Date: Jul. 8, 2005

(87) PCT Pub. No.: WO03/092580

PCT Pub. Date: Nov. 13, 2003

(65) Prior Publication Data

US 2006/0052406 A1 Mar. 9, 2006

Related U.S. Application Data

(60) Provisional application No. 60/377,433, filed on May 3, 2002.

(51) Int. Cl.
*A61K 31/438* (2006.01)
*C07D 513/10* (2006.01)

(52) U.S. Cl. .............................. 514/278; 546/19; 546/16
(58) Field of Classification Search ................. 514/278; 546/19, 16
See application file for complete search history.

(56) References Cited

U.S. PATENT DOCUMENTS 3,723,442 A    3/1973   Nakanishi et al.
5,534,520 A    7/1996   Fisher et al.
5,852,029 A    12/1998  Fisher et al.

FOREIGN PATENT DOCUMENTS

EP    0 711 292 B1   1/2002
WO    WO 85/03866    9/1985

OTHER PUBLICATIONS

English Abstract, Caplus DN 102:226107 Matsuda, Rieko et al 1985.
Data Base Caplus [Online] Chemical Abstracts Service, Columbus Ohio US; 1989 Menendez, J.C. et al; "Synthesis and antibacterial activity of some 1-thia-4, 8-diazaspiro [4.5]decan-3-ones, thiazolo[2,3-a]-3-onesi and 1,3-onesi and 1,3-thiazino [2,3-a] isoquinolin-4-ones" XP002385656.
Data Base Caplus [Online] Chemical Abstract Service, Columbus, Ohio, US 1971 Nakanishi, Michio et al: "Piperidine derivatives. IV. Synthesis of 3-oxo-1-thia-4,8-diazaspiro[4,5]decane derivatives. 2" XP002385657.
Beach et al., Reduction of cerebrospinal fluid amyloid β after systematic administration of M1 muscarinic agonists. Brain Research, 905:220-223, 2001.
Fisher et al., AF150(S) and AF267(b). Journal of Molecular Neuroscience, 19:145-153, 2002.
Fisher, Therapeutic strategies in Alzheimer's disease: M1 muscarinic agonists. Jpn. J. Pharmacol. 84:101-112, 2000.
Fisher et al., $M_1$ muscarinic agonists can modulate some of the hallmarks in Alzheimer's disease: Implications in future therapy. Journal of Molecular Neuroscience, 20(3): 349-356, 2003.
Ikonen and Tanila, Effects of metrifonate on the hippocampal theta rhythm of freely moving intact as MS-lesioned mice. Pharmacology, Biochemistry and Behavior, 69:165-172, 2001.

*Primary Examiner*—Charanjit S Aulakh
(74) *Attorney, Agent, or Firm*—Foley & Lardner LLP; Stephen E. Reiter

(57) ABSTRACT

There are provided methods for the treatment of diseases involving dysfunction of the peripheral and central nervous system comprising administering one or more spiro compounds. Also provided are pharmaceutical compositions useful in such methods, compounds for use in the preparation of such pharmaceutical compositions, processes for preparing compounds useful in the practice of such methods, and some novel such compounds per se.

25 Claims, No Drawings

METHODS AND COMPOSITIONS FOR TREATMENT OF CENTRAL AND PERIPHERAL NERVOUS SYSTEM DISORDERS AND NOVEL COMPOUNDS USEFUL THEREFOR

RELATED APPLICATIONS

This application is a 371 of PCT Application No. IL2003/00357, which claims the benefit of U.S. Provisional Application Ser. No. 60/377,433, filed May 3, 2002, the entire contents of which are hereby incorporated by reference herein.

FIELD OF THE INVENTION

The invention relates to methods for treating various central and peripheral nervous system disorders.

BACKGROUND OF THE INVENTION

The following documents, the contents of which are incorporated herein by reference, are believed to be relevant:

Fisher and Barak. Drug News & Perspectives 7: 453-64, 1994; Review: Fisher. Jap J Pharmacol 84: 101-112, 2000; Wolozin et at. Arch Neurol. 57:1439-43, 2000; Sparks et al. Neurosci Lett 187:142-144, 1995; Refolo et al. Soc Neurosci Abst, San Diego, Calif., USA, 2001; Refolo et al. Neurobiol Dis 8: 890-899, 2001; Review: Cedazo-Minguez and Cowburn. J Cell Mol Med 5:254-266, 2001; Bales et al. PNAS 96: 15233, 1999; Buttini et al. Neurosci 97: 207, 2000;, Hartmann et al, Exp Neurol 170: 326, 2001; Mudher and Lovestone. Trends Neurosci 25:22-6, 2002; Mudher et al. J Neurosci 21:4987-95, 2001; Zhang et al. Nature 395: 698-702, 1998; De Ferrari et al. Brain Res Brain Res Rev 33:1-12, 2000; Garrido et al. FASEB J 16:1982-4, 2002; Eldar-Finkelman. Trends Molec Med. 8:126-32, 2002; Bhat et al. Neurosignals 11:251-61, 2002; Gentleman et al. NeuroReport 8: 1519-1522, 1997; Roberts et al. J Neurol Neurosurg Psychiat, 57: 419-425, 1994; Havlik et al. Neurobiol Aging S140, 587, 1998; Mayeux et al. Neurol, 45: 556-557, 1995; Nicoll et al. Ann NY Acad Sci, 777: 271-275, 1996; Capruso and Levin. Neurol Clin 10: 879-893, 1992; Dixon et. al. Behav Brain Res 70:125-131, 1995; Pike and Hamm Exptl Neurol, 147: 55-65, 1997; Pike and Hamm. Pharmacol Biochem Behav, 57: 785-791, 1997; Pike and Hamm. J Neurotrauma, 14: 897-905, 1997; U.S. Pat. Nos. 4,855,290, 4,981,858, 4,900,830, 4,876,260, 5,053,412, 5,407,938, 6,277,874, 6,274,603;

Irwin, S. PSYCHOPHARM 13:222-257, 1968; Beach et al, Neurosci Lett 283: 9-12, 2000; Beach et al., Brain Res 905: 220-223, 2001; Pfeifer et al., Science 2002 298:1379; Nicoll et al, Nature Medicine, March 2003, Sparks et al. Neurosci Lett 1995; 187:142-144; Refolo et al Neurobiol Dis 8: 890-899, 2001; Refolo et al, Soc Neurosci Abst 2001, San Diego, Calif., USA; Cedazo-Minguez et al, Neurosci, 105: 651-661, 2001; Sparks et al. Neurosci Lett 1995; 187:142-144; Dean et at, Mol Psychiatry 1996; 1:54-8; Dean et al, Mol Psychiatry 2002; 7: 1083-91; Raedler et al, Am J. Psychiatry 160: 118, 2003; Borda et al J Immunol 2002; 168:3667-74; Felder et al, Life Sci 2001 8:2605-13; Bymaster et al, Current Drug Targets—CNS & Neurological Disorders 2002; 1:147-164; Sullivan et al, Br J Psychiatry 2000; 177:177-8; Gould and Manji. Neuroscientist 2002; 8:497-511; Cotter et al, NeuroReport 9: 1379, 1998; Casanova M F et al Acta Neuropathol (Berl) 2002 103: 313-20; Auld et al Prog Neurobiol 2002, 68:20945; Poeggeler et al, Brain Res 815: 382-388, 1999; Chyan et al. J Biolog Chem 274: 21937-21942, 1999; Bons et al., Allheimer's Res (1995) 1:83-87; Mazzoti et at (Proceedings of the Chiral Europe 96 Symp, Spring Innovations, Stockport UK, p 103, 1996; Krise et al, J Med. Chem. 42: 3094-3100 (1999); Fassbeder et al, PNAS, 98: 5856, 2001; Sparks et al. Exp Neurol 1994; 126:88-94; Sparks Nutr Metab Cardiovasc Dis 1997: 7:255-266; Beach et al, Neurosci Lett 283: 9-12, 2000; Beach et al Brain Res. 905: 220-223, 2001; Klausner, Biotechnol 5:779-786, 1987; Lipman et al, Cytotechnol 8:129-176, 1992; Rappoport and Ferreira J. Neurochem. 74:125133 (2000); Ekinci et al J. Biol. Chem. 274: 30322-30327 (1999); Sadot et al J.Neurochem. 66:877880, 1996; Poirier et al Neuroscience 55: 81-90 (1993); Cedazo-Minuez et al [Neurosci 105: 651-661, 2001; Gurwitz et al Eur. J. Pharmacol. 267, 21, 1993; Fisher et al, J. Neural Transm Suppl 62: 189, 2002; Chen et al, J Neurotrauma, 15: 231-237, 1998; Dantzer et al. Psychopharmacol. 91:363-368, 1987; Perio et al Psychopharmacol. 97: 262-268. 1989; Perio et al Psychopharmacol. 97: 262-268. 1989; Fisher et al, J. Pharmacol. Exptl. Therap., 257: 392, 1991; Simons et al Life Sci., 42, 375-383, 1988; Simons et al, 1988; Vincent et al Brain Res., 597, 264-268, 1992; Schwarz et al Drug Dev. Res., 40, 133-143, 1997; Voll et et al, Stroke, 20: 1700-1706, 1989; Bymaster et al. J Pharmacol Exp Ther 267: 16-24, 1993; Roldan et al Neurosci. Lett 230: 93-96, 1997; Kimura et al Brain Res. 834: 612, 1999; Garrido J L et al. (FASEB J 2002; 16:1982.

SUMMARY OF THE INVENTION

There is provided in accordance with an embodiment of the invention a compound of the formula (I):

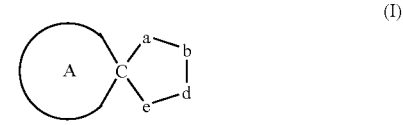

wherein:
C denotes a spiro carbon atom shared by ring A and the ring containing a, b, d and e;
A is selected from the group consisting of:

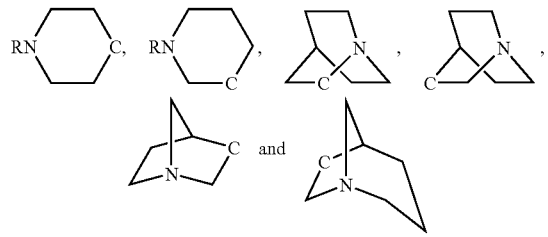

wherein R is selected from H, $C_1$-$C_8$ straight- or branched-chain alkyl, or —$CH_2$—P(=O)($OH$)$_2$;
a is —O— or —S—;
b is —$CR^1R^2$— or —$C(R_1)$=;
d is selected from the group consisting of =N—, —C(=O)—, —C(=S)— and =N($R^3$)=O;
e is selected from the group consisting of —$CH^2$—, —$CHR^4$—, —NH—, —$NR^5$—, —N($SO_2R^6$)— and —N(C(=O)$R^6$)—;
R, $R^1$, $R^2$, $R^3$, $R^4$ are each independently selected from H, $C_{1-6}$ alkyl optionally substituted by one, two or three phenyls, $C_{1-6}$ alkoxy, $C_{2-6}$ hydroxyalkyl, $C_{2-6}$ alkenyl, and $C_{2-6}$ alkynyl;

R$^5$ is independently selected from H, C$_{1-6}$ alkyl optionally substituted by one, two or three phenyls, C$_{1-6}$ alkoxy, C$_{2-6}$ hydroxyalkyl, C$_{2-6}$ alkenyl, C$_{2-6}$ alkynyl, substituted phenyl, and heteroaryl; and R$^6$ is selected from C$_{1-6}$ alkyl, C$_{1-6}$ alkoxy, C$_{1-6}$ alkylthio, C$_{2-6}$ hydroxyalkyl, C$_{2-6}$ alkenyl, C$_{2-6}$ alkynyl, and C$_{3-7}$ cycloalkyl, each optionally substituted by from 1-6 halogen atoms, hydroxy-C$_{1-6}$-alkyl, aryl substituted with a halogen, nitro, amino, hydroxyl, or CF$_3$ group, and C$_{1-6}$ alkyl substituted by one, two or three aryl groups, C$_{1-6}$ alkyl indole, isoindolyl, 3-pyridinyl, 3-piperidinyl, benzimidazolyl, thienyl, isothiazolyl, imidazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,5-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, and pteridinyl;

or an enantiomer, diastereomer, racemate, tautomer, geometrical isomer, dimer, metabolite or pharmaceutically acceptable salt thereof, with the proviso that when A is

R is —CH$_3$, a is S, b is —CH(CH$_2$CH$_3$)— and d is —C(=O)—, then e is not —NH— (AF267 or an enantiomer thereof), and with the further proviso that when A is

R is —CH$_3$, a is S, b is —C(CH$_3$)= and d is =N—, then e is not —CH$_2$— (AF150(S)).

In an embodiment of the invention, R$^5$ is heteroaryl selected from the group consisting of indole, pyrrolidinyl, piperidinyl, piperazinyl, furyl, pyridyl, pyrimidyl, thienyl, isothiazolyl, imidazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,5-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl.

In an embodiment of the invention, the compound is a dimer of a compound of formula 1, wherein e is —NR$^5$— and the two formula 1 moieties share a common group R$^5$ which is selected from the group consisting of —(CH$_2$)$_n$— and —(CH$_2$O)$_n$—, wherein n is 1 to 6, or an enantiomer, diastereomer, racemate, tautomer, metabolite or pharmaceutically acceptable salt thereof.

In an embodiment of the invention, the compound is selected from the group consisting of:

N-[(2,8-Dimethyl-1-oxa-8-aza-spiro[4.5]dec-3-ylidene) amine]-N-oxide; N-[(2-Ethyl-8-methyl-1-oxa-8-aza-spiro [4.5]dec-3-ylidene)-amine]-N-oxide; N-[(2-Methyl-8-phenyl-1-oxa-8-aza-spiro[4.5]dec-3-ylidene)-amine]-N-oxide; Thia-4,8-diaza-spiro[4.5]decan-3-one; 4-(2,4-Dimethoxy-benzyl)-8-methyl-1-thia-4,8-diaza-spiro[4.5] decan-3-one (AF286); 8-Methyl-4-pyrrolidin-1-ylmethyl-1-thia-4,8-diaza-spiro[4.5]decan-3-one (AF287); 2-(1-Hydroxy-ethyl)-8-methyl-1-thia-4,8-diaza-spiro[4.5] decan-3-one (AF298); (S)-2-Ethyl-8-methyl-8-oxy-1-thia-4,8-diaza-spiro[4.5]decan-3-one (AF299); 4-(2,4-Dimethoxy-benzyl)-2-ethyl-8-methyl-1-thia-4,8-diaza-spiro[4.5]decan-3-one (AF288); (S)-2-Ethyl-8methyl-1-oxo-1λ$^4$-thia-4,8-diaza-spiro[4.5]decan-3-one (AF300); 2-Ethyl-8-methyl-1-thia-4,8diaza-spiro[4.5]decane-3-thione (AF510); (S)-2-Ethyl-4-(4-fluoro-benzenesulfonyl)-8-methyl-1-thia-4,8-diaza-spiro[4.5]deca-3-one (AF700); 2-Ethyl-4-[2-(1H-indol-3-yl)-ethyl]-8-methyl-1-thia-4,8-diaza-spiro[4.5]deca-3-one (AF703); 2-Ethyl-4-(3-1H-indol-3-yl-propionyl)-8-methyl-1-thia-4,8-diaza-spiro[4.5]decan-3-one (AF704); (S)-Ethyl-4-(3-1H-indol-3-yl-propionyl)-8-methyl-1-thia-4,8-diaza-spiro [4.5]decan-3-one (AF704B); (R)-Ethyl-4-(3-1H-indol-3-yl-propionyl)-8-methyl-1-thia-4,8-diaza-spiro[4.5]decan-3-one (AF704A); and 2-Methyl-8-methyl-d$_3$-1-thia-3,8-diaza-spiro[4.5]dec-2-ene (AF402), or an enantiomer, diastereomer, racemate, tautomer, geometrical isomer, metabolite, or a pharmaceutically acceptable salt thereof.

In an embodiment of the invention, the compound is AF292 or a pharmaceutically acceptable salt thereof.

In an embodiment of the invention, the compound is a compound wherein A is

R is H, a is —S—; b is —CH(CH$_2$CH$_3$)—; d is —(C=O)—; and e is —NH—, i.e. 2-Ethyl-1-thia-4,8-diaza-spiro[4.5]decan-3-one (AF504), or an enantiomer, diastereomer, geometrical isomer, racemate, tautomer, dimer, metabolite or pharmaceutically acceptable salt thereof.

In an embodiment of the invention, the compound is (S)-2-Ethyl-1-thia-4,8-diaza-spiro[4.5]decan-3-one (AF292) or its HCl salt.

In an embodiment of the invention, the compound is (R)-2-Ethyl-1-thia-4,8-diaza-spiro[4.5]decan-3-one (AF291).

In an embodiment of the invention, the compound is a compound wherein A is

R is —CH$_3$, a is —O—, d is =N(R$^3$)=O, or an enantiomer, diastereomer, racemate, tautomer, geometrical isomer, dimer, metabolite or pharmaceutically acceptable salt thereof. In an embodiment of the invention, b is —CH(CH$_3$)— and R$^3$ is —CH$_3$, i.e. N-[(2,8-Dimethyl-1-oxa-8-aza-spiro[4.5]dec-3-ylidene)-methyl-amine]-N-oxide (AF600). In an embodiment of the invention, b is —CH(CH$_3$)— and R$^3$ is benzyl, i.e. N-[(2,8-Dimethyl-1-oxa-8-aza-spiro[4.5]dec-3-ylidene-benzyl-amine]-N-oxide (AF604). In an embodiment of the invention, b is —CH(CH$_3$)— and R$^3$ is isopropyl, i.e. N-[(2, 8-Dimethyl-1-oxa-8-aza-spiro[4.5]dec-3-ylidene)-isopropyl-amine]-N-oxide (AF605). In an embodiment of the invention, b is —CH(CH₂CH₃)— and R³ is —CH₃, i.e. N-[(2-Ethyl-8-methyl-1-oxa-8-aza-spiro[4.5]dec-3-ylidene) methyl-amine]-N-oxide (AF601). In an embodiment of the invention, b is —CH(CH₃)— and R³ is phenyl, i.e. N-[(2-Methyl-8-phenyl-1-oxa-8-aza-spiro[4.5]dec-3-ylidene)-methyl-amine]-N-oxide (AF602).

In an embodiment of the invention, the compound is a compound wherein A is

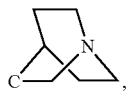

R is —CH₃, a is —O—, d is =N(R³)=O, or an enantiomer, diastereomer, racemate, tautomer, geometrical isomer, dimer, metabolite or pharmaceutically acceptable salt thereof. In an embodiment of the invention, b is —CH(CH₃)— and R³ is methyl, i.e. Dihydro-5'-methylspiro[1-azabicyclo[2.2.2]octane-3,5'-(4'H) 3'-ylidene-methylamine]-N-oxide (AF603).

In an embodiment of the invention, the compound is a compound wherein A is

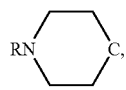

R is methyl, a is —S—, b is —CH(CH₂CH₃)—; d is —C(=O)—; e is —NR⁵— wherein R⁵ is selected from —(CH₂)₃-indolyl and —C(=O)—(CH₂)₃-indolyl, i.e. 2-Ethyl-4-[2-(1H-indol-3-yl)-ethyl]-8-methyl-1-thia-4,8-diaza-spiro[4.5]decan-3-one (AF703) or 2-Ethyl-4-(3-1H-indol-3-yl-propionyl)-8-methyl-1-thia-4,8-diaza-spiro[4.5]decan-3-one (AF704), or an enantiomer, diastereomer, geometrical isomer, racemate, tautomer, dimer, metabolite or pharmaceutically acceptable salt thereof. In an embodiment of the invention, the is (S)-Ethyl-4-(3-1H-indol-3-yl-propionyl)-8-methyl-1-thia-4,8-diaza-spiro[4.5]decan-3-one (AF704B).

There is also provided in accordance with an embodiment of the invention the use of a compound of formula (I), or an enantiomer, diastereomer, racemate, tautomer, geometrical isomer, dimer, metabolite or pharmaceutically acceptable salt thereof, in the preparation of a pharmaceutical composition. In an embodiment of the invention, the compound is AF292 or a prodrug of AF292 or a pharmaceutically acceptable salt of either AF292 or a prodrug of AF292. In an embodiment of the invention, the prodrug is AF767B or a pharmaceutically acceptable salt thereof.

There is also provided in accordance with an embodiment of the invention a pharmaceutical composition comprising at least one compound of formula (I), or an enantiomer, diastereomer, racemate, tautomer, geometrical isomer, dimer, metabolite or pharmaceutically acceptable salt thereof, and a pharmaceutically acceptable carrier, diluent or excipient therefor. In an embodiment of the invention, the compound is AF292 or a prodrug of AF292 or a pharmaceutically acceptable salt thereof. In an embodiment of the invention, the prodrug is AF267B or a pharmaceutically acceptable salt thereof.

There is also provided in accordance with an embodiment of the invention a method of stimulating the M1 muscarinic receptor, comprising administering to a patient in need thereof an efficacious amount of a compound selected from the group consisting of compounds of formula (I), AF267 and AF150(S), or an enantiomer, diastereomer, racemate, tautomer, geometrical isomer, dimer, metabolite or pharmaceutically acceptable salt thereof. In an embodiment of the invention, the compound is AF292 or a prodrug of AF292 or a pharmaceutically acceptable salt thereof. In an embodiment of the invention, the prodrug is AF267B or a pharmaceutically acceptable salt thereof.

There is also provided in accordance with an embodiment of the invention a compound of formula (I) wherein A is

R is —CH₃, a is —O—, d is =N(R³)=O, or an enantiomer, diastereomer, racemate, tautomer, geometrical isomer, dimer, metabolite or pharmaceutically acceptable salt thereof in the preparation of a pharmaceutical composition for both stimulating the M1 muscarinic receptor and retarding oxidation in the vicinity of said M1 muscarinic receptor.

There is also provided in accordance with an embodiment of the invention a pharmaceutical composition comprising an M1 muscarinic receptor agonistic efficacious amount of a compound of formula (I) wherein A is

R is —CH₃, a is —O—, d is =N(R³)=O, or an enantiomer, diastereomer, racemate, tautomer, geometrical isomer, dimer, metabolite or pharmaceutically acceptable salt thereof, and at least one pharmaceutically acceptable carrier, diluent or excipient therefor.

There is also provided in accordance with an embodiment of the invention a method of stimulating the M1 muscarinic receptor, comprising administering to a patient in need thereof an efficacious amount of a compound of formula (I) wherein A is

R is —CH₃, a is —O—, d is =NR³)=O, or an enantiomer, diastereomer, racemate, tautomer, geometrical isomer, dimer, metabolite or pharmaceutically acceptable salt thereof.

There is also provided in an embodiment of the invention the compound (S)-2-Ethyl-4(4-fluoro-benzenesulfonyl)-8-methyl-1-thia-4,8-diaza-spiro[4.5]decan-3-one (AF700).

There is also provided in accordance with an embodiment of the invention the use of the compound AF700, or an enantiomer, diastereomer, racemate, tautomer, metabolite or pharmaceutically acceptable salt thereof, in the preparation of a pharmaceutical composition for both stimulating the M1 muscarinic receptor and activating α secretase.

There is also provided in accordance with an embodiment of the invention a pharmaceutical composition comprising an M1 muscarinic receptor stimulating and α-secretase activating efficacious amount the compound AF700, or an enantiomer, diastereomer, racemate, tautomer, metabolite or pharmaceutically acceptable salt thereof, and at least one pharmaceutically acceptable carrier, diluent or excipient therefor.

There is also provided in accordance with an embodiment of the invention a method of stimulating the M1 muscarinic receptor and activating α secretase, comprising administering to a patient in need thereof an efficacious amount of the compound AF700, or an enantiomer, diastereomer, racemate, tautomer, metabolite or pharmaceutically acceptable salt thereof.

There is also provided in accordance with an embodiment of the invention the use of the compound AF700, or an enantiomer, diastereomer, racemate, tautomer, metabolite or pharmaceutically acceptable salt thereof, in the preparation of a pharmaceutical composition for both stimulating the M1 muscarinic receptor and antagonizing β secretase.

There is also provided in accordance with an embodiment of the invention a pharmaceutical composition comprising an M1 muscarinic receptor agonistic and β-secretase antagonistic efficacious amount of the compound AF700, or an enantiomer, diastereomer, geometrical isomer, racemate, tautomer, dimer, metabolite or pharmaceutically acceptable salt thereof, and at least one pharmaceutically acceptable carrier, diluent or excipient therefor.

There is also provided in accordance with an embodiment of the invention a method of stimulating the M1 muscarinic receptor and antagonizing β-secretase, comprising administering to a patient in need thereof an efficacious amount of the compound AF700, or an enantiomer, diastereomer, geometrical isomer, racemate, tautomer, dimer, metabolite or pharmaceutically acceptable salt thereof.

There is also provided in accordance with an embodiment of the invention the use of the compound AF700, or an enantiomer, diastereomer, racemate, tautomer, metabolite or pharmaceutically acceptable salt thereof, in the preparation of a pharmaceutical composition for both stimulating the M1 muscarinic receptor and antagonizing β-secretase.

There is also provided in accordance with an embodiment of the invention a pharmaceutical composition comprising an M1 muscarinic receptor agonistic and γ-secretase antagonistic efficacious amount of the compound AF700, or an enantiomer, diastereomer, racemate, tautomer, metabolite or pharmaceutically acceptable salt thereof, and at least one pharmaceutically acceptable carrier, diluent or excipient therefor.

There is also provided in accordance with an embodiment of the invention a method of stimulating the M1 muscarinic receptor and antagonizing γ-secretase, comprising administering to a patient in need thereof an efficacious amount of the compound AF700, or an enantiomer, diastereomer, racemate, tautomer, metabolite or pharmaceutically acceptable salt thereof.

There is also provided in accordance with an embodiment of the invention the use of the compound (S)-2-Ethyl-1-thia-4,8-diaza-spiro[4.5]decan-3-one (AF292), or a metabolite or pharmaceutically acceptable salt thereof, in the preparation of a pharmaceutical composition for both stimulating the M1 muscarinic receptor and antagonizing the M3 muscarinic receptor.

There is also provided in accordance with an embodiment of the invention a pharmaceutical composition comprising an M1 muscarinic receptor agonistic and M3 muscarinic receptor antagonistic efficacious amount of the compound (S)-2-Ethyl-1-thia-4,8-diaza-spiro[4.5]decan-3-one (AF292), or a metabolite or pharmaceutically acceptable salt thereof, and at least one pharmaecutically acceptable carrier, diluent or excipient therefor.

There is also provided in accordance with an embodiment of the invention human or animal blood containing the compound (S)-2-Ethyl-1-thia-4,8-diaza-spiro[4.5]decan-3-one (AF292), or a metabolite or pharmaceutically acceptable salt thereof. In an embodiment of the invention, the blood is located in a human or animal body. In an embodiment of the invention, the blood is not located in a human or animal body.

There is also provided in accordance with an embodiment of the invention human or animal blood plasma containing the compound (S)-2-Ethyl-1-thia-4,8-diaza-spiro[4.5]decan-3-one (AF292), or a metabolite or pharmaceutically acceptable salt thereof. In an embodiment of the invention, the blood is located in a human or animal body. In an embodiment of the invention, the blood is not located in a human or animal body.

There is also provided in accordance with an embodiment of the invention the compound (S)-2-Ethyl-1-thia-4,8-diaza-spiro[4.5]decan-3-one (AF292) according to claim 1, or a metabolite or pharmaceutically acceptable salt thereof whenever located in a human or animal body.

There is also provided in accordance with an embodiment of the invention the compound (S)-2-ethyl-8-methyl-1-thia-4,8-diaza-spiro[4.5]decan-3-one (AF267B) for use as a prodrug of the compound (S)-2-Ethyl-1-thia-4,8-diaza-spiro[4.5]decan-3-one (AF292).

There is also provided in accordance with an embodiment of the invention the use of the compound (S)-2-ethyl-8-methyl-1-thia-4,8-diaza-spiro[4.5]decan 3-one (AF267B) as a prodrug of the compound (S)-2-Ethyl-1-thia-4,8-diaza-spiro[4.5]decan-3-one (AF292).

There is also provided in accordance with an embodiment of the invention the use of a combination of the compounds (S)-2-ethyl-8-methyl-1-thia-4,8-diaza-spiro[4.5]decan-3-one (AF267B) and (S)-2-Ethyl-1-thia-4,8-diaza-spiro[4.5]decan-3-one (AF292) in the preparation of pharmaceutical composition for stimulating the M1 muscarinic receptor and antagonizing the M3 muscarinic receptor.

There is also provided in accordance with an embodiment of the invention a pharmaceutical composition comprising an M1 muscarinic receptor agonistic and M3 muscarinic receptor antagonistic amount of a combination of the compounds AF267B and AF292 and at least one pharmaceutically acceptable carrier, diluent or excipient therefor.

There is also provided in accordance with an embodiment of the invention a method of stimulating the M1 muscarinic receptor and antagonizing the M3 muscarinic receptor in a patient, comprising administering to a patient an efficacious amount of a combination of the compounds AF267B and AF292.

In an embodiment of the invention, AF267B and AF292 are administered together. In an embodiment of the invention, AF267B and AF292 are administered separately. In an embodiment of the invention, AF267B and AF292 are administered at different times. In an embodiment of the invention, AF267B and AF292 are administered at the same times.

There is also provided in accordance with an embodiment of the invention the use of a combination of a first compound which is (S)-2-Ethyl-1-thia-4,8-diaza-spiro[4.5]decan-3-one (AF292) and a second compound selected from the group consisting of compound of formula (I), AF267B and AF150(S), including racemates, enantiomers, diastereomers, tautomers, geometric isomers and pharmaceutically acceptable salts thereof, in the preparation of a pharmaceutical composition for stimulating the M1 muscarinic receptor while minimizing adverse side-effects due to stimulation of other mAChR subtypes.

There is also provided in accordance with an embodiment of the invention a pharmaceutical composition comprising an M1 muscarinic receptor agonistic amount of a combination of a first compound which is AF292 and a second compound selected from the group consisting of compounds of formula (I), AF267B and AF150(S), including racemates, enantiomers, diastereomers, geometric isomers, tautomers and pharmaceutically acceptable salts thereof, and at least one pharmaceutically acceptable carrier, diluent or excipient therefor.

There is also provided in accordance with an embodiment of the invention a method of stimulating the M1 muscarinic receptor while minimizing adverse side-effects due to stimulation of other mAChR subtypes in a patient, comprising administering to a patient an efficacious amount of a combination of a first compound which is AF292 and a second compound selected from the group consisting of compounds of formula (I), AF267B and AF150(S), including racemates, enantiomers, diastereomers, tautomers, geometric isomers and pharmaceutically acceptable salts thereof. In an embodiment of the invention, the first compound and the second compound are administered together. In an embodiment of the invention, the first compound and the second compound are administered separately. In an embodiment of the invention, the first compound and the second compound are administered at different times. In an embodiment of the invention, the first compound and the second compound are administered at the same time.

There is also provided in accordance with an embodiment of the invention a method for stimulating the M1 muscarinic receptor in a patient simultaneously with AF267B and AF292, comprising administering to a patient an amount of AF267B efficacious to form in vivo an amount of a mixture of AF267B and AF292 efficacious to stimluate the M1 muscarinic receptor.

There is also provided in accordance with an embodiment of the invention 2-Ethyl-4-(3-1H-indol-3-yl-propionyl)-8-methyl-1-thia-4,8-diaza-spiro[4.5]decan-3-one in racemic form (AF704) or as the S-enantiomer thereof (AF704B), for use as a prodrug of at least one of the group of AF267B, AF292 and indole-3-propionic acid There is also provided in accordance with an embodiment of the invention the use of 2-Ethyl-4-(3-1H-indol-3-yl-propionyl)-8-methyl-1-thia-4,8-diaza-spiro[4.5]decan-3-one in racemic form (AF704) or as the S-enantiomer thereof (AF704B), in the preparation of a pharmaceutical composition for stimulating the M1 muscarinic receptor, retarding oxidation in the vicinity of the M1 muscarinic receptor, and providing neuroprotectant activity.

There is also provided in accordance with an embodiment of the invention a pharmaceutical composition comprising an M1 muscarinic receptor stimulating, oxidation-retarding and neuroprotectant activity efficacious amount of the compound 2-Ethyl-4-(3-1H-indol-3-yl-propionyl)-8-methyl-1-thia-4,8-diaza-spiro[4.5]decan-3-one in racemic form (AF704) or as the S-enantiomer thereof (AF704B), and a pharmaceutically acceptable carrier, diluent, or excipient therefor.

There is also provided in accordance with an embodiment of the invention a process for the preparation of 2-ethyl-8-methyl-1-thia-4,8-diaza-spiro[4.5]decan-3-one (AF267), comprising reacting 4-ethyl piperidone with 2-mercaptobutyric acid and ammonia. In an embodiment of the invention, the process further comprising obtaining the enantiomers AF267A (R-enantiomer) and AF267B (S-enantiomer) by chiral separation.

There is also provided in accordance with an embodiment of the invention a process for the preparation of AF267B, comprising racemizing AF267A and isolating AF267B from the racemic mixture. In an embodiment of the invention, the isolating comprising separating the AF267B from the racemic mixture by chiral separation.

There is also provided in accordance with an embodiment of the invention a process for the synthesis of AF267B comprising contacting (R)-2-mercaptobutyric acid with ammonium acetate and 1-methyl-4-piperidone. In an embodiment of the invention the (R)-2-mercaptobutyric is obtained by contacting (R)-2-benzoylthiobutyric acid with ammonium hydroxide. In an embodiment of the invention the (R)-2-benzoylthiobutyric acid is obtained by contacting (R)-2-bromobutyric acid with cesium thiobenzoate. In an embodiment of the invention the (R)-2-bromobutyric acid is obtained by contacting 2-aminobutyric acid having the R configuration with sodium nitrite, potassium bromide and hydrobromic acid.

There is also provided in accordance with an embodiment of the invention a process for the preparation of $^{14}C$-labelled AF267B, comprising reacting AF287 with $^{14}C$-labelled ethyl bromide, deprotecting the nitrogen atom at the 4-position of the AF287, and isolating $^{14}C$-labelled AF267B by chiral chromatography.

There is also provided in accordance with an embodiment of the invention a process for the preparation of a mixture of (S)-2-Ethyl-1-thia-4,8-diaza-spiro[4.5]decan-3-one (AF292) and (R)-2-Ethyl-1-thia-4,8-diaza-spiro[4.5]decan-3-one (AF291) comprising reacting AF267 with a demethylating agent.

There is also provided in accordance with an embodiment of the invention a crystalline form of (S)-2-ethyl-8-methyl-1-thia-4,8-diaza-spiro[4.5]decane-3-one (AF267B) characterized by the following data: P212121 (No 16) a=10394 ((10) ($\alpha$=90°), b=20.133 (2) ($\beta$=90°), c=5.856 (4) ($\gamma$=90°), Å, T=110K. In an embodiment of the invention, the crystalline form is further characterized by the following data: Volume=1224.2 (9) Å$^3$, Z=4, Fw=202.32, Calculated density, Dc=1.092 Mg/m$^3$, Absorption coefficient, $\mu$=0.232 mm$^{-1}$.

There is also provided in accordance with an embodiment of the invention a crystalline form of (AF267B) having the configuration shown in Structure 1 in Example 2.

There is also provided in accordance with an embodiment of the invention a process for the preparation of 2,8-Dimethyl-1-thia-3,8-diaza-spiro[4.5]dec-2-ene [AF150(S)] comprising cyclizing 1-methyl-4-N-thioacetylamino-1,2,3,6-tetra-hydropyridine. In an embodiment of the invention the cyclizing is conducted in the presence of phosphoric acid. In an embodiment of the invention the 1-methyl-4-N-thioacetylamino-1,2,3,6-tetrahydropyridine is obtained by reduction of reduction of 1-methyl-4-N-thioacetylaminomethyl pyridinium with sodium borohydride. In an embodiment of the invention the 1-methyl-4-N-thioacetylaminomethyl pyridinium is obtained by reacting 4-(acetaminomethyl)-1-methyl-pyridinium iodide with Lawesson's reagent.

There is also provided in accordance with an embodiment of the invention apharmaceutical formulation comprising AF 150(S) in paraffin oil.

There is also provided in accordance with an embodiment of the invention a method for inhibiting the release or synthesis of beta-amyloid peptide (A$\beta$) in a mammalian cell, tissue or organism comprising administering to a mammalian cell, tissue or organism an amount of a compound or a mixture of compounds selected from the group consisting of compounds of formula (I), AF267B and AF150(S), or racemates, enantiomers, geometrical isomers, diasteromers, tautomers and pharmaceutically acceptable salts thereof effective to inhibit the cellular release or synthesis of Aβ.

There is also provided in accordance with an embodiment of the invention the use of a compound or a mixture of compounds selected from the group consisting of compounds of formula (I), AF267B and AF150(S), or racemates, enantiomers, geometrical isomers, diasteromers, tautomers and pharmaceutically acceptable salts thereof in the preparation of a pharmaceutical composition for inhibiting the release or synthesis of beta-amyloid peptide (Aβ) in a mammalian cell, tissue or organism.

There is also provided in accordance with an embodiment of the invention a method for elevating the level of secreted form of the non-amyloidogenic amyloid precursor protein (α-APPs) in a mammalian cell, tissue or organism comprising administering to a mammalian cell, tissue or organism an amount of a compound or a mixture of compounds selected from the group consisting of compound of formula (I), AF267B and AF150(S), or racemates, enantiomers, geometrical isomers, diasteromers, tautomers and pharmaceutically acceptable salts thereof effective to elevate the level of the secreted form of the non-amyloidogenic amyloid precursor protein (α-APPs).

There is also provided in accordance with an embodiment of the invention the use of a compound or a mixture of compounds selected from the group consisting of compounds of formula (I), AF267B and AF150(S), or racemates, enantiomers, geometrical isomers, diasteromers, tautomers and pharmaceutically acceptable salts, in the preparation of a pharmaceutical composition for elevating the level of secreted form of the non-amyloidogenic amyloid precursor protein (α-APPs) in a mammalian cell, tissue or organism.

There is also provided in accordance with an embodiment of the invention a method for decreasing the level of Aβ peptide in the brain of a mammal having an elevated level of Aβ in the brain, comprising administering to a mammal having an elevated level of Aβ in the brain an amount of a compound or a mixture of compounds selected from the group consisting of compounds of formula (I), AF267B and AF150(S), or racemates, enantiomers, geometrical isomers, diasteromers, tautomers and pharmaceutically acceptable salts thereof effective to decrease the level of Aβ in the brain of said mammal. In an embodiment of the invention the elevated level of Aβ in the brain is a result of hypercholesterolemia In an embodiment of the invention the elevated level of Aβ in the brain is a result of cholinergic hypofunction.

There is also provided in accordance with an embodiment of the invention the use of a compound or a mixture of compounds selected from the group consisting of compound of formula (I), AF267B and AF150(S), or racemates, enantiomers, geometrical isomers, diasteromers, tautomers and pharmaceutically acceptable salts thereof in the preparation of a pharmaceutical composition for decreasing the level of Aβ peptide in the brain of a mammal having an elevated level of Aβ in the brain.

There is also provided in accordance with an embodiment of the invention a method for inhibiting the synthesis or release of apolipoprotein (ApoE) in a mammalin cell, tissue or organism comprising administering to a mammalian cell, tissue or organism an amount of a compound or a mixture of compounds selected from the group consisting of compound of formula (I), AF267B and AF150(S), or racemates, enantiomers, geometrical isomers, diasteromers, tautomers and pharmaceutically acceptable salts thereof effective to inhibit the release or synthesis of ApoE in said mammalian cell, tissue or organism.

There is also provided in accordance with an embodiment of the invention the use of a compound or a mixture of compounds selected from the group consisting of compound of formula (I), AF267 and AF150(S), or racemates, enantiomers, geometrical isomers, diasteromers, tautomers and pharmaceutically acceptable salts thereof in the preparation of a pharmaceutical composition for inhibiting the release or synthesis of ApoE in a mammalian cell, tissue or organism. In an embodiment of the invention the ApoE is ApoE4.

There is also provided in accordance with an embodiment of the invention a method for decreasing levels of apolipoprotein (ApoE) in a mammalian cell, tissue or organism comprising administering to a mammalian cell tissue or organism an amount of a compound or a mixture of compounds selected from the group consisting of compound of formula (I), AF267B and AF150(S), or racemates, geometrical isomers, enantiomers, diasteromers, tautomers and pharmaceutically acceptable salts thereof effective to decrease the levels of ApoE in said mammalian cell, tissue or organism.

There is also provided in accordance with an embodiment of the invention the use of a compound or a mixture of compounds selected from the group consisting of compounds of formula (I), AF267B and AF150(S), or racemates, enantiomers, geometrical isomers, diasteromers, tautomers and pharmaceutically acceptable salts thereof in the preparation of a pharmaceutical composition for decreasing levels of ApoE in a mammalian cell, tissue or organism. In an embodiment of the invention the ApoE is ApoE4.

There is also provided in accordance with an embodiment of the invention a method for decreasing tau hyperphosphorylation in a mammalian cell, tissue or organism comprising administering to a mammalian cell, tissue or organism a compound or a mixture of compounds selected from the group consisting of compounds of formula (I), AF267B and AF150(S), or racemates, enantiomers, geometrical isomers, diasteromers, tautomers and pharmaceutically acceptable salts thereof effective to inhibit tau hyperphosphorylation. In an embodiment of the inventionthe tau hyperphosphorylation is Aβ-induced tau hyperphosphorylation.

There is also provided in accordance with an embodiment of the invention the use of a compound or a mixture of compounds selected from the group consisting of compounds of formula (I), AF267B and AF150(S), or racemates, enantiomers, geometrical isomers, diasteromers, tautomers and pharmaceutically acceptable salts thereof in the preparation of a pharmaceutical composition for decreasing tau hyperphosphorylation in a mammalian cell, tissue or organism.

There is also provided in accordance with an embodiment of the invention a method for decreasing paired helical formation in a mammalian cell, tissue or organism comprising administering to a mammalian cell, tissue or organism a compound or a mixture of compounds selected from the group consisting of compounds of formula (I), AF267B and AF150(S), or racemates, enantiomers, geometrical isomers, diasteromers, tautomers and pharmaceutically acceptable salts thereof effective to inhibit tau hyperphosphorylation.

There is also provided in accordance with an embodiment of the invention the use of a compound or a mixture of compounds selected from the group consisting of compounds of formula (I), AF267 and AF150(S), or racemates, enantiomers, diasteromers, tautomers, geometrical isomers and pharmaceutically acceptable salts thereof in the preparation of a pharmaceutical composition for decreasing paired helical formation in a mammalian cell.

There is also provided in accordance with an embodiment of the invention a method for activating the Wnt signaling pathway in a mammalian cell, tissue or organism comprising administering to a mammalian cell, tissue or organism a compound or a mixture of compounds selected from the group consisting of compounds of formula (I), AF267B and AF150(S), or racemates, enantiomers, diasteromers, tautomers, geometrical isomers and pharmaceutically acceptable salts thereof effective to inhibit Wnt abnormalities.

There is also provided in accordance with an embodiment of the invention the use of a compound or a mixture of compounds selected from the group consisting of compounds of formula (I), AF267 and AF150(S), or racemates, enantiomers, diasteromers, tautomers, geometrical isomers and pharmaceutically acceptable salts thereof in the preparation of a pharmaceutical composition for activating the Wnt signaling pathway in a mammalian cell, tissue or organism.

There is also provided in accordance with an embodiment of the invention a method for inhibiting GSK3β-mediated effects in a mammalian cell, tissue or organism comprising administering to a mammalian cell, tissue or organism a compound or a mixture of compounds selected from the group consisting of compounds of formula (I), AF267B and AF150(S), or racemates, enantiomers, diasteromers, tautomers, geometrical isomers and pharmaceutically acceptable salts thereof effective to inhibit GSK3β-mediated effects. In an embodiment of the invention the GSK3β-mediated effects are selected from the group consisting of tau: hyperphosphorylation, apoptosis, β-catenin degradation, and decrease in Wnt target genes.

There is also provided in accordance with an embodiment of the invention the use of a compound or a mixture of compounds selected from the group consisting of compounds of formula (I), AF267 and AF150(S), or racemates, enantiomers, diasteromers, tautomers, geometrical isomers and pharmaceutically acceptable salts thereof in the preparation of a pharmaceutical composition for inhibiting GSK3β-mediated effects in a mammal In an embodiment of the invention the method is used in response to insults induced by Aβ peptides or oxidative stress starvation to Wnt signaling, apoptosis, or cell viability.

There is also provided in accordance with an embodiment of the invention a method for enhancing the activity of endogenous growth factors, i.e. neutrophins, in a cell, comprising administering to a mammalian cell, tissue or organism an amount of a compound or a mixture of compounds selected from the group consisting of compounds of formula (I), AF267B and AF150(S), or racemates, enantiomers, geometrical isomers, diasteromers, tautomers and pharmaceutically acceptable salts thereof which alone is effective as a neurotrophic agent and which acts synergistically with said neurotrophins.

There is also provided in accordance with an embodiment of the invention the use of a compound or a mixture of compounds selected from the group consisting of compounds of formula (I), AF267B and AF150(S), or racemates, enantiomers, diasteromers, tautomers, geometrical isomers and pharmaceutically acceptable salts thereof which alone is effective as a neurotrophic agent and which acts synergistically with endogenous growth factors, i.e. neurotrophins, in the preparation of a pharmaceutical composition for enhancing the activity of neurotrophins.

There is also provided in accordance with an embodiment of the invention a pharmaceutical composition for inhibiting the release or synthesis of beta-amyloid peptide (Aβ), for elevating the level of secreted form of the non-amyloidogenic amyloid precursor protein (α-APPs), for decreasing the level of Aβ peptide in the brain of a mammal having an elevated level of Aβ in the brain, for inhibiting the release or synthesis of ApoE, for decreasing levels of ApoE, for decreasing tau hyperphosphorylation, for decreasing paired helical formation, for activating the Wnt signaling pathway, for increasing beta-catenin, for inhibiting GSK3β-mediated effects or for for enhancing the activity of neurotrophins, comprising a compound or a mixture of compounds selected from the group consisting of compounds of formula (I), AF267B and AF150(S), or racemates, enantiomers, geometrical isomers, diasteromers, tautomers and pharmaceutically acceptable salts thereof, and at least one pharmaceutically acceptable carrier, diluent or excipient.

There is also provided in accordance with an embodiment of the invention a pharmaceutical composition comprising at least one compound selected from the group consisting of compounds of formula (I), AF267B and AF150(S), or racemates, enantiomers, geometrical isomers, diasteromers, tautomers and pharmaceutically acceptable salts thereof and at least one additional pharmacologically active compound selected from the group consisting of: cholinesterase inhibitors, nicotinic agonists, cholinergic precursors and cholinergic enhancers, nootropics, peripheral antimuscarinc drugs, M2 muscarinic antagonists, M4 antagonists, benzodiapine inverse agonists, antidepressants, tricyclic antidepressants or antimuscarinic drugs used in treatment of Parkinson's disease (PD) or depression, antipsychotic and antischizophrenic agents, glutamate antagonists and modulators, NMDA antagonists, AMPA agonists, acetyl-L-carnitine, MAO-B inhibitors, peptides and growth factors, cholesterol-lowering agents, antioxidants, GSK-3β inhibitors, Wnt-ligands, β- or γ-secretase inhibitors, beta-amyloid degrading agents, beta-amyloid anti-aggregation agents, chelating agents, immunotherapeutic compounds against beta-amyloids, compounds that bind to amyloids, cyclooxygenase (COX)-2 inhibitors, non-steroidal antiinflammatory drugs, estrogenic agents, estrogenic receptor modulators, steroidal neuroprotectants, and spin trapping pharmaceuticals.

In an embodiment of the invention the compound is AF292 or a prodrug of AF292 or a pharmaceutically acceptable salt thereof.

There is also provided in accordance with an embodiment of the invention a method for treating or reducing cerebral amyloid angiopathy comprising administering to a patient in need thereof (a) an efficacious amount of a compound selected from the group consisting of AF267B, AF292, and AF704B pharmaceutically acceptable salts thereof or mixtures of such compounds or salts, and (b) an efficacious amount of a compound selected from an immunotherapeutic compound against beta-amyloids and compounds that bind to amyloids.

There is also provided in accordance with an embodiment of the invention a pharmaceutical composition comprising (a) an efficacious amount of a compound selected from the group consisting of AF267B, AF292, and AF704B pharmaceutically acceptable salts thereof or mixtures of such compounds or salts, and (b) an efficacious amount of a compound selected from an immunotherapeutic compound against beta-amyloids and compounds that bind to amyloids, and a pharmaceutically acceptable carrier, diluent or exicipient therefor.

There is also provided in accordance with an embodiment of the invention the use of a combination of (a) a compound selected from the group consisting of AF267B, AF292, and AF704B pharmaceutically acceptable salts thereof or mixtures of such compounds or salts, and (b) a compound selected from an immunotherapeutic compound against beta-amyloids and compounds that bind to amyloids, in the preparation of a pharmaceutical composition for treating or reducing cerebral amyloid angiopathy.

There is also provided in accordance with an embodiment of the invention a method for treating in a mammal diseases associated with impaired cholinergic function or diseases where there is an imbalance in cholinergic function, or diseases with impaired activity of acetylcholine receptors from the group consisting of: senile dementia of Alzheimer's type; Alzheimer's disease (AD); Lewy body dementia; mixed Alzheimer's and Parkinson's disease; multiifract dementia (MD); fronto-temporal dementia; vascular dementia; strokerischemia, MID combined with stroke/ischemia/head injury; combined MID and AD; human head injury; age-associated memory impairments; mild cognitive impairment (MCI); MCI conducive to AD; cognitive dysfunction (including forgetfulness, acute confusion disorders, attention-deficit disorders, focus and concentration disorders); hallucinatory-paranoid states; emotional and attention disorders; sleep disorders; post-operative delirium; adverse effects of tricyclic antidepressants; adverse effects of certain drugs used in the treatment of schizophrenia and Parkinson's disease; xerostomia, anomia, memory loss and/or confusion; psychosis; schizophrenia, schizophrenia comorbit with AD, late onset schizophrenia, paraphrenia, schizophreniform disorders; anxiety, bipolar disorders; mania; mood stabilization; cognitive impairments after removal of certain gliomas; tardive dyskinesia; oxidative stress during oxygen therapy, aphasia; postencephalitic amnesic syndrome; AIDS dementia; memory impairments in autoimnune diseases including lupus, multiple sclerosis, Sjogren's syndrome, chronic fatigue syndrome, and fibromyalgia; memory impairments in atypical depression or schizophrenia; pain, rheumatism, arthritis and terminal illness;, xerophtalmia, vaginal dryness, skin dryness; immune dysfunctions; neurocrine disorders and dysregulation of food intake, including bulimia and anorexia; obesity; congenital ornithine transcarbamylase deficiency; ollivopontocerebral atrophy; alcohol withdrawal symptoms; substance abuse including withdrawal symptoms and substitution therapy; Huntington's chorea; progressive supranuclear palsy; Pick's disease; Friedrick's ataxia; Gilles de la Tourette disease; Down's syndrome; glaucoma; presbyopia; autonomic disorders including dysfunction of gastrointestinal motility and function such as inflammatory bowel disease, irritable bowel syndrome, diarrhea, constipation, gastric acid secretion and ulcers; urinary urge incontinence, asthma, COPD; comprising administering to a mammal in need of such treatment a compound a mixture of compounds selected from the group consisting of compounds of formula (I), AF267B and AF150(S), or racemates, enantiomers, diasteromers, tautomers and pharmaceutically acceptable salts thereof in an amount effective to treat one of said diseases. In an embodiment of the invention the compound is AF292 or a prodrug of AF292 or a pharmaceutically acceptable salt thereof.

There is also provided in accordance with an embodiment of the invention a method for preventing or treating central or peripheral nervous system disease states due to dysfunction in one or more of the following: brain, nervous system, cardiovascular system, immune system, neurocrine system, gastrointestinal system, or endocrine and exocrine glands, eye, cornea, lungs, prostate, or other organs where the cholinergic function is mediated by muscarinic receptor subtypes, wherein said dysfunction involves: brain amyloid-mediated disorders; glycogen synthase kinase (GSK3β)-mediated disorders; tau protein hyperphosphorylation-mediated damages, dysfunctions or diseases; CNS and PNS hypercholester-olemia- and/or hyperlipidemia-mediated damages, dysfunctions or diseases; Wnt-mediated signaling abnormalities; impairment of neuroplasticity; hyperglycemia; diabetes; endogenous growth factors-mediated diseases, or combination of additional risk factors; or disease states that involve apolipoprotein E; or disturbances in which a cholinergic dysfunction has been implicated, including: senile dementia of Alzheimer's type, Alzheimer's disease (AD), delay of onset of AD symptoms in a patient at risk for developing AD, Lewy body dementia, cerebral amyloid angiopathy (CAA), cerebral amyloidosis, fronto-temporal dementia, vascular dementia, hyperlipidemia, hypercholesterolemia, multiifract dementia (MID), stroke ischemia, MID combined with stroke/ischemia/head injury, combined MID and Alzheimer's disease, human head injury, age-associated memory impairments, mild cognitive impairment (MCI), MCI conducive to AD, bipolar disorder, mania, schizophrenia, noneffective sychozophrenia, paraphrenia, immune dysfunctions, neurocrine disorders and dysregulation of food intake, including bulimia and anorea, weight control, obesity, inflammation; comprising administering to a mammal in need of such treatment a compound or a mixture of compounds selected from the group consisting of compounds of formula (I), AF267B and AF150(S), or racemates, enantiomers, diasteromers, tautomers and pharmaceutically acceptable salts thereof in an amount effective to treat at least one of said diseases. In an embodiment of the invention the compound is AF292 or a prodrug of AF292 or a pharmaceutically acceptable salt thereof.

There is also provided in accordance with an embodiment of the invention a method for treating a patient with AD, MCL Lewi Body Dementia, fronto temporal dementia, vascular dementia, memory impairment in head injury, AIDS dementia in order to inhibit further deterioration in the condition of said patient comprising administering to said patient an efficacious amount of a compound or a mixture of compounds selected from the group consisting of compounds of formula (I), AF267B and AF150(S), or racemates, enantiomers, diasteromers, tautomers, geometric isomers and pharmaceutically acceptable salts thereof.

In an embodiment of the invention the compound is AF292 or a prodrug of AF292 or a pharmaceutically acceptable salt thereof.

There is also provided in accordance with an embodiment of the invention a method of treating schizophrenia, comprising administering to a patient in need thereof an efficacious amount of a compound selected from the group consisting of AF267B, AF292, pharmaceutically acceptable salts thereof and mixtures of AF267B, AF292 or salts thereof.

There is also provided in accordance with an embodiment of the invention the use of AF267B, AF292, pharmaceutically acceptable salts thereof or a mixture of AF267B, AF292 or pharmaceutically acceptable salts thereof in the preparation of a pharmaceutical composition for the treatment of schizophrenia.

There is also provided in accordance with an embodiment of the invention a pharmaceutical composition for the treatment of schizophrenia, comprising AF267B, AF292, pharmaceutically acceptable salts thereof or a mixture of AF267B, AF292 or pharmaceutically salts thereof and at least one pharmaceutically acceptable carrier, diluent or excipient There is also provided in accordance with an embodiment of the invention a method of ameliorating symptoms of schizophrenia, comprising administering to a patient in need thereof an efficacious amount of a compound selected from the group consisting of AF267B, AF292, pharmaceutically acceptable salts thereof and mixtures of of AF267B, AF292 or pharmaceutically acceptable salts thereof.

There is also provided in accordance with an embodiment of the invention the use of AF267B, AF292, pharmaceutically acceptable salts or mixtures of AF267B, AF292 or pharmaceutically acceptable salts thereof in the preparation of a pharmaceutical composition for amelioration of symptoms of schizophrenia There is also provided in accordance with an embodiment of the invention a pharmaceutical composition for amelioration of symptoms of schizophrenia, comprising a compound selected from AF267B, AF292, pharmaceutically acceptable salts thereof and mixtures of AF267B, AF292 or pharmaceutically acceptable salts thereof and at least one pharmaceutically acceptable carrier, diluent or excipient.

In this patent application,

"alkyl" means a linear or branched chain of 1-8 carbon atoms, e.g. methyl, ethyl, propyl, isopropyl etc.

"alkoxy" means —O-alkyl, e.g. to methoxy, ethoxy, propxy, isopropoxy, etc.

"alkenyl" means a linear or branched chain of 2-8 carbon atoms having at least one C—C double bond in the chain.

"alkynyl" means a linear or branched chain of 2-8 carbon atoms having at least one C—C triple bond in the chain.

"alkylthio" means —S-alkyl, e.g. methylthio, ethylthio, propylthio, isopropylthio etc.

"cycloalkyl" refers to mono- and bicyclic ring structures containing 3-12 carbon atoms. Examples of cycloalkyl are cyclopropyl, cyclobutyl, cyclopentyl, cyclohexyl, decalinyl, and norbornyl.

"aryl" refers to a mono- or bicyclic aromatic ring structure containing 5-12 carbon atoms. Examples of aryl are phenyl, naphthyl and benzyl.

"heterocyclic" refers to mono- and bicyclic ring structures containing 4-12 carbon atoms and at least one nitrogen, oxygen or sulfur atom.

"heteroaryl" refers to a mono- or bicyclic aromatic ring structure containing 4-12 carbon atoms and at least one nitrogen, oxygen or sulfur atom. Examples of heterocyclic and heteraryl are indolyl, isoindolyl, 3-pyridinyl, 3-piperidinyl, benzimidazolyl, thienyl, isothiazolyl, imidazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,5-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, and pteridinyl, pyrrolidinyl, piperidinyl, piperazinyl, furyl, pyridyl, pyrimidyl, 5-azacytidinyl, 5-azauracilyl, triazolopyridinyl, imidazolopyridinyl, pyrrolopyrimidinyl, and pyrazolo-pyrimidinyl.

"halogen atom" may be one of fluorine, chloride, bromine and iodine.

Unless noted otherwise, the following abbreviations are used:

| | |
|---|---|
| Aβ | β-amyloid |
| AA | arachidonic acid |
| AAMI | age associated memory impairment |
| ACh | acetylcholine |
| AchE-Is | acetylcholinesterase inhibitors |
| AD | Alzheimer's disease |
| AGP | Human α-glycoprotein |
| AGP | α-glycoprotein |
| ApoE | apolipoprotein |
| APP | amyloid precursor protein |
| AUC | area under the curve |
| BDNF | brain derived growth factor |
| bFGF | basic fibroblast growth factor |
| CAA | cerebral amyloid angiopathy |
| CCh | carbachol |
| CDX | methyl-β-cyclodextrin |
| CE | collision energy |
| CHI | closed head injury |
| CNS | central nervous system |
| CSF | cerebrospinal fluid |
| DAPI | 4,6-diamidino-2-phenylindole |
| DCC | dicyclohexylcarbodiimide |
| DDW | double distilled water |
| DMF | N,N-dimethyl formamide |
| DMAP | 4-dimethylaminopyridine |
| DMPU | N,N'-dimethyl-N,N'-propylene urea |
| ECG | electrocardiogram |
| EGF | epidermal growth factor |
| FACS | Fluorescence activated cell sorter |
| FCS | fetal calf serum |
| GC | gas chromatography |
| GSK3β | glycogen synthase kinase |
| HERG | human ether-a-go-go related gene |
| HPLC | high performance liquid chromatograph |
| HS | horse serum |
| HSA | human serum albumin |
| i.c.v., icv | intracerebroventricular |
| i.p., ip | intraperitoneally |
| i.v., iv | intravenous |
| LBD | Lewy Body disease |
| LC | liquid chromatogrph |
| LDA | di-isopropylamine |
| Li | lithium |
| M1 mAChR | 1 muscarinic receptor |
| mAChR | muscarinic receptor |
| mCPBA | m-chloroperbenzoic acid |
| MCI | minimal cognitive impairment |
| MID | multiifract dementia |
| MRSA | muscarinic receptor selective agonists and potent antioxidants |
| MS | mass spectrometry |
| MTBE | Methyl-t-butyl ether |
| MTT | 3-(4,5-dimethylthiazol-2-yl)-2,5-diphenyl-tetrazolium bromide |
| MWM | Morris water maze |
| nbm | nucleus basalis magnocellularis |
| NFT | neurofibrillary tangles |
| NGF | Nerve Growth Factor |
| NMDA | N-methyl-D-Aspartate |
| NMR | nuclear magnetic resonance |
| NOAEL | no-adverse-effect-level |
| NSS | neurological severity scores |
| OXO-M | oxotremorine-M |
| PA | passive avoidance |
| PBS | phosphate-buffered saline |
| PD | Parkinson's disease |
| PHF | paired helical filaments |
| PI | phosphoinositide |
| PKC | protein kinase C |
| PMSF | Phenylmethylsulfonylfluoride |
| PNS | peripheral nervous system |
| po | per os, oral |
| PS-1 | presenilin-1 |
| PZ | pirenzepine |
| QNB | quinuclidinyl benzilate |
| REL | ratio of escape latency |
| RID | Ratio of Investigation Duration |
| ROS | reactive oxygen species |
| RPL | ratio of path length |
| RSA | Receptor Selective Antioxidants |
| s.c., sc | subcutaneously |
| SDAT | senile dementia of Alzheimer's type |
| SDS-PAGE | sodium dodecyl sulfate-polyacrylamide gel electrophoresis |
| SMB | Simulated Moving Bed |
| TBI | traumatic brain injury |
| Tg | transgenic |
| THF | tetrahydrofuran |
| TUNEL | Terminal deoxynucleotidyl transferase (TdT) mediated dUTP nick end labeling |

| | |
|---|---|
| A1 (human); A2A (human); A3 (human) | adenosine receptor subtypes |
| AT1 (Human Recombinant) | angiotensin |
| BZD (central) | benzodiazepine |
| B2 (Human Recombinant) | bradykinin |
| CCKA (Human Recombinant) (CCK1) | cholecystokinin |
| D1 (Human Recombinant); D2S (Human Recombinant) | dopamine receptor subtypes |
| ETA (Human Recombinant) | endothelin |
| GABA (non-selective) | gamma-aminobutyric acid |
| GAL2 (h) | galanin |
| IL-8B (Human Recombinant) (CXCR2) | chemokine receptor subtype |
| CCR1 (Human Recombinant) | chemokine receptor subtype |
| H1 (central); H2 | histamine receptor subtypes |
| MC4 (Human Recombinant) | melanocortine |
| ML1 | melatonin |
| NK2 (Human Recombinant); NK3 (Human Recombinant) | tachykinin |
| Y1 (human); neuropeptide, Y2 (human) | neuropeptide |
| NT1 (Human Recombinant) (NTS1) | neurotensin |
| delta 2 (Human Recombinant); (DOP); kapp (KOP); opiate, mu (Human Recombinant) (MOP) | opiate receptor subtypes |
| ORL1 (Human Recombinant) (NOP) | orphanin |
| 5-$HT_{1A}$ (Human Recombinant); 5-$HT_{1B}$; 5-$HT_{2A}$ (Human Recombinant); 5-$HT_3$ Human Recombinant); 5-$HT_{5A}$ (Human Recombinant) (5-ht5A); 5-$HT_6$ (Human Recombinant); 5-$HT_7$ (human) | serotonin sutypes |
| sst (non-selective) | somatostatin |
| VIP1 (human) (VPAC1) | vasoactive intestinal peptide |
| V1a (Human Recombinant) | vasopressin |
| NE transporter (human) | norepinephrine |

The term "geometrical isomers" refers to isomerism across a double-bond, e.g. cis/trans isomerism and E/Z isomerism, as well as conformational isomers, e.g. and syn/anti isomerism.

The term "pharmaceutically acceptable addition salts" refers to salts known in the art to be acceptable in pharmaceutical practice, for example acid addition salts such as hydrochloric acid salts, maleic acid salts, and citric acid salts. Pharmaceutically acceptable acid addition salts include salts derived form inorganic acids such as hydrochloric, nitric, phosphoric, sulfuric, hydrobromic, hydroiodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite; bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," J. of Pharmaceutical Science, 1977;66:1-19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N-dibenzylethylenediamine, chloroprocaine, choline, diethanolamine, ethylenediamine, N-methylglucamine, and procaine; see, for example, Berge et al., supra., 1977.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

The term "metabolite" refers to a form of a compound obtained in a human or animal body by action of the body on the administered form of the compound, for example a demethylated analogue of a compound bearing a methyl group which is obtained in the body after administration of the methylated compound as a result of action by the body on the methylated compound. Metabolites may themselves have biological activity.

The term "prodrug" refers to a form a compound which after administration to a human or animal body is converted chemically or biochemically to a different compound in said body having biological activity. A prodrug form of a compound may itself have biological activity.

The novel compounds of embodiments of the present invention, and compounds which may be used in accordance with embodiments of the present invention may have at least one chiral center, and may accordingly exist as enantiomers or as mixtures of enantiomers (e.g., racemic mixtures). Where the compounds possess two or more chiral centers, they may additionally exist as diastereoisomers.

In some embodiments of the present invention, there are provided pharmaceutical compositions and the use of certain compounds in the manufacture of pharmaceutical compositions. Such compositions may be in a form suitable for oral (e.g. in the form of capsules, tablets, granules, powders or beads), rectal, parenteral, intravenous, intradermal, subcutaneous, transdermal or topical administration, or for administration by insufflation or nasal spray, iontophoretic, bucal, or sublingual lingual administration. Such compositions may be in unit dosage form. The compound of formula (I), or, in those embodiments in which AF267B or AF150(S) may be employed, may be present in the unit dosage in an amount in the range of about 0.5 to about 100 mg. In an embodiment of the invention the compound is present in an amount of about 5 to about 100 mg. In an embodiment of the invention the compound is present in an amount of about 10 to about 50 mg. These amounts may represent a single dose or the total of 2-4 individual doses for administration from 2 to 4 times per day. In an embodiment of the invention, the pharmaceutical composition is in sustained release form.

Certain of the compounds in some embodiments of the present invention can exist in unsolvated forms as well as solvated forms, including hydrated forms. In general, the solvated forms, including hydrated forms, are equivalent to unsolvated forms and are intended to be encompassed within the scope of the present invention.

The compounds AF150(S) and AF267B have been described in U.S. Pat. No. 5,852,029.

In some embodiments of the invention, the compounds have antioxidant activity. Such antioxidant activity may be the result of such compounds being N-oxides, such as AF600, or it may be the result of such compounds having an antioxidant moiety linked at the 4position nitrogen.

The skilled artisan will appreciate that many factors influence the selection of any compound for application in clinical therapy, e.g., effectiveness for the intended purpose, safety, possible side-effects and therapeutic index. The skilled artisan will thus appreciate how to interpret the expression "pharmaceutically acceptable quaternary compounds" which are structurally derived from the inventive compounds having a tertiary nitrogen atom, as this expression is used in the present specification and claims.

The compounds used in embodiments of the present invention can be prepared and administered in a wide variety of oral and parenteral dosage forms. Thus, the compounds used can be administered by injection, that is, intravenously, intramuscularly, intracutaneously, subcutaneously, intraduodenally, or intraperitoneally. Also, the compounds can be administered by inhalation, for example, intranasally. Additionally, the compounds can be administered transdermally. It will be appreciated by those skilled in the art that the following dosage forms may comprise as the active component, either a compound of Formula (I) or a corresponding pharmaceutically acceptable salt of a compound of Formula (I), in accordance with embodiments of the invention optionally with AF267B or AF150(S) present as well.

For preparing pharmaceutical compositions from compounds of formula (I), optionally also including AF267B or AF150(S), pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component In tablets, the active component or components is mixed with the carrier having the necessary binding properties in suitable proportions and compacted in the shape and size desired.

In an embodiment of the invention, the powders and tablets contain from five or ten to about seventy percent of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic guns, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

In an embodiment of the invention the pharmaceutical preparation is in unit dosage form. In such form the preparation is subdivided into unit doses containing appropriate quantities of the active component The unit dosage form can be a packaged preparation, the package containing discrete quantities of preparation, such as packeted tablets, capsules, and powders in vials or ampoules. Also, the unit dosage form can be a capsule, table, cachet, or lozenge itself, or it can be the appropriate number of any of these in packaged form.

The quantity of active component in a unit dose preparation may be varied or adjusted as recited above, according to the particular application and the potency of the active component. The composition can, if desired, also contain other compatible therapeutic agents.

In therapeutic use, the compounds utilized in accordance with embodiments of this invention may be administered at the initial dosage of about 0.01 mg to about 100 mg/kg daily. In an embodiment of the invention, a daily dose range of about 0.01 mg to about 10 mg/kg is used. In another embodiment of the invention, a daily dose range of 10 to 50 mg/kg is used. The dosages, however, may be varied depending upon the requirements of the patient, the severity of the condition being treated, and the compound or compounds being employed. Determination of the proper dosage for a particular situation is within the skill of the art Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The methods used for preparing compounds of the invention include methods which are essentially known to organic chemists for the formation of the five-membered rings, ring-substitution, changing the degree of ring saturation/unsaturation, interconversion of salts and bases, quaternary salt formation, and so forth. In these synthetic methods, the starting materials may contain a chiral center and, when a racemic starting material is employed, the resulting product is a mixture of R, S enantiomers. Alternatively, a chiral isomer of the starting material may be employed and, if the reaction protocol employed does not racemize this starting material, a chiral product is obtained. Such reaction protocols may involve inversion of the chiral center during synthesis. Select compounds of formula (I) are capable of existing in a number of stereoisomeric forms including geometric isomers such as E and Z (in the nitrones) and enantiomers. The invention includes each of these stereoisomeric forms, and to mixtures thereof (including racemates). The different stereoisomeric forms may be separated one from the other by the usual methods, or any given isomer may be obtained by stereospecific or asymmetric synthesis. It will be appreciated, therefore, that while exemplary methods of preparing certain compounds of the invention will be described, other methods may also be used to prepare the compounds, as will be known by skilled person.

When the five-membered ring is thiazolidine-3'-one ring, for example, the compounds may be prepared by forming this ring by reacting the corresponding N-heterocyclic ketone with 2-mercapto carboxylic acid [$R^1CH(SH)CO_2H$] and ammonia, and the 4-N atom in the product may be substituted in known manner. These reactions may be illustrated as follows in Scheme 1, where the N-heterocyclic ketone is exemplarily 1-methylpiperidine-4-one.

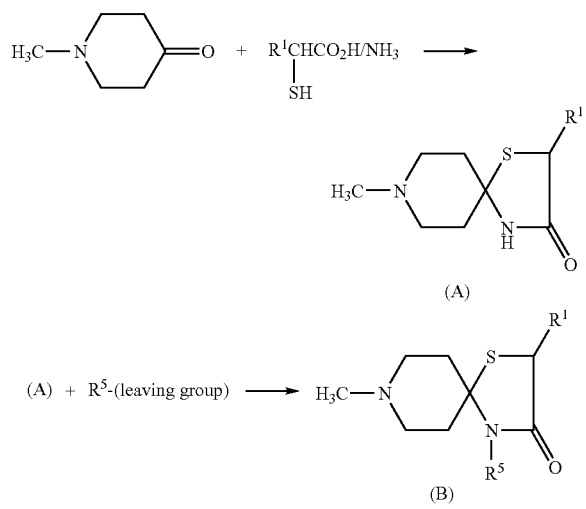

[(A) e.g. AF267: $R^1$ = Et, $R^5$ = H; AF277: $R^1$ = H, $R^5$ = H);
(B) e.g. AF700: $R^1$ = Et, $R^5$ = 4-fluorobenzenesulfonyl;
AF703: $R^1$ = Et, $R^5$ = 2-(1H-indol-3-yl)-ethyl]

The leaving group in "$R^5$-(leaving group)" may be e.g. bromide or chloride. This substitution reaction to obtain structure (B) may be conducted under essentially known condition, e.g. by reacting of (A) in presence of an alkali such as lithium di-isopropylamine (LDA) and using a solvent such as tetrahydrofuran (THF).

Compound structure (A) or compound structure (B) can be separated into two enantiomers by chiral HPLC, e.g. chiral preparative liquid chromatogrph (LC) separation of AF267 ($R^1$=Et, $R^5$=H) gave AF267A [$R^1$=(R)Et, $R^5$=H] and the active enantiomer AF267B [$R^1$=(S)Et, $R^5$=H]. A large scale cost-effective method was developed and a maximum 50% yield of each enantiomer can be obtained (yield>97% of each enantiomer, with ee>99% and HPLC purity>99%).

The method can be further expanded for an even more practical separation for those skilled in the art using a Simulated Moving-Bed (SMB) technology for chiral separation as defined by Mazzoti et al (Proceedings of the Chiral Europe 96 Symp, Spring Innovations, Stockport UK, p 103, 1996).

AF267B can also be produced by racemization of the AF267A by chemical means, e.g. base-catalysis, or by enzyme-catalyzation followed by chiral HPLC or SMB separation.

Structure (B) may be prepared by reacting the corresponding N-heterocyclic ketone with 2-mercapto acid [$R^1CH(SH)CO_2H$] and primary amine. This reaction may be illustrated as follows in Scheme 2, where the N-heterocyclic ketone is exemplarily 1-methylpiperidine-4-one:

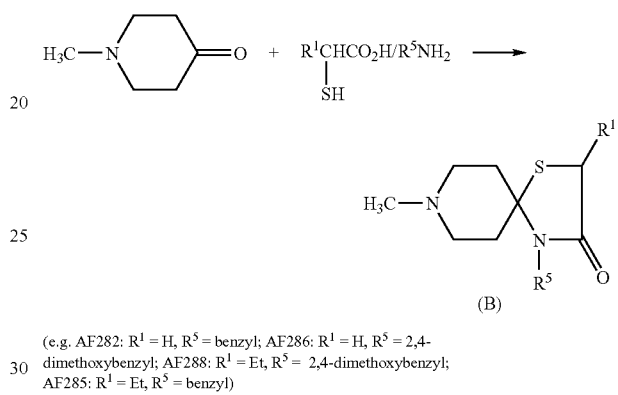

(e.g. AF282: $R^1$ = H, $R^5$ = benzyl; AF286: $R^1$ = H, $R^5$ = 2,4-dimethoxybenzyl; AF288: $R^1$ = Et, $R^5$ = 2,4-dimethoxybenzyl; AF285: $R^1$ = Et, $R^5$ = benzyl)

Structure (B) may also be obtained by reacting (A) under conditions to obtain amide bond as described below in Scheme 3, where the reacting acid is exemplarily 3-indolpropionic acid:

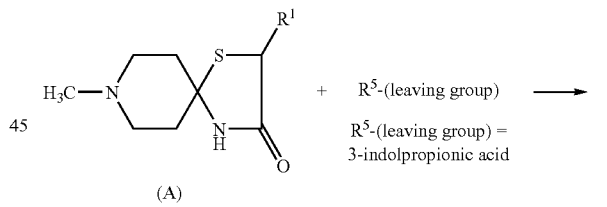

e.g. AF267 $R^1$ = Et

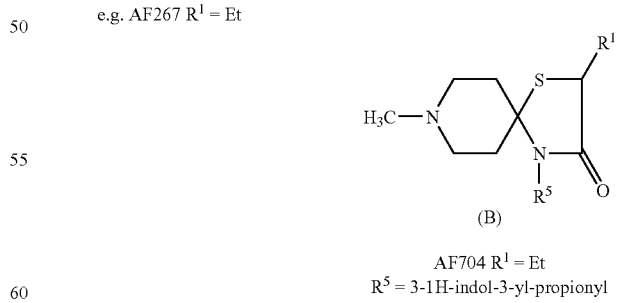

AF704 $R^1$ = Et
$R^5$ = 3-1H-indol-3-yl-propionyl

The $R^1$ group in structure (A) or in structure (B) may be obtained by reaction of the 2-unsubstituted compound (A) or (B) with alkyl halide or alkyl aldehyde under standard conditions to effect substitution in the 2 position. These reactions may be illustrated as follows in Scheme 4:

SCHEME 4

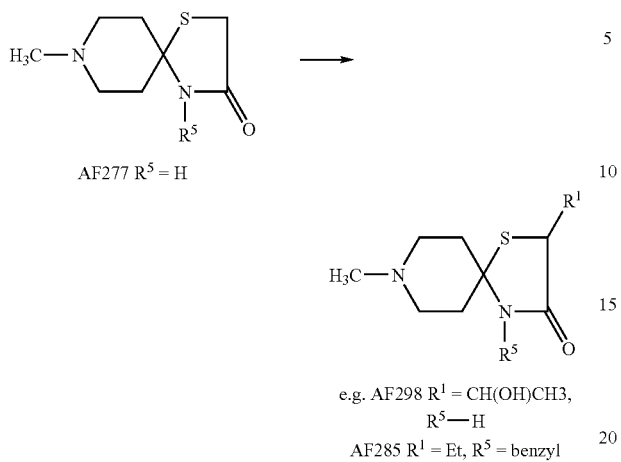

AF277 R⁵ = H e.g. AF298 R¹ = CH(OH)CH3, R⁵=H
AF285 R¹ = Et, R⁵ = benzyl

This method can be applied to $^{14}C$-labeling of AF267. The introduction of the ethyl moiety by alkylation of the readily available N-protected AF277 (AF287) with $^{14}C$-labeled ethyl bromide, followed by removal of the protecting group yield $^{14}C$-labeling of AF267. The synthetic pathway, which may be used analogously to prepare AF267 enriched with $^{13}C$, is described below in Scheme 5:

The 1-methyl group in structure (A) and in structure (B) may be removed by reaction with m-chloroperbenzoic acid/ $FeCl_2$ or with demethylating agent such as phenylchloroformate as shown in Scheme 6:

SCHEME 6

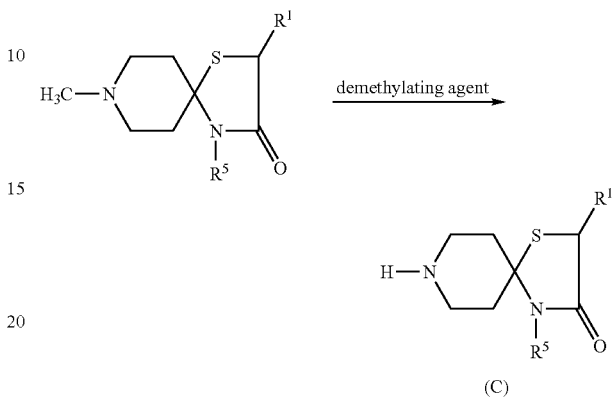

e.g. AF504 R¹ = Et, R⁵ = H; AF292 = [(S)-AF504]

AF504 or AF292 may also be prepared by reacting the corresponding N-heterocyclic ketone with 2-mercaptocarboxylic acid [$R^1CH(SH)CO_2H$] and primary amine. This

SCHEME 5

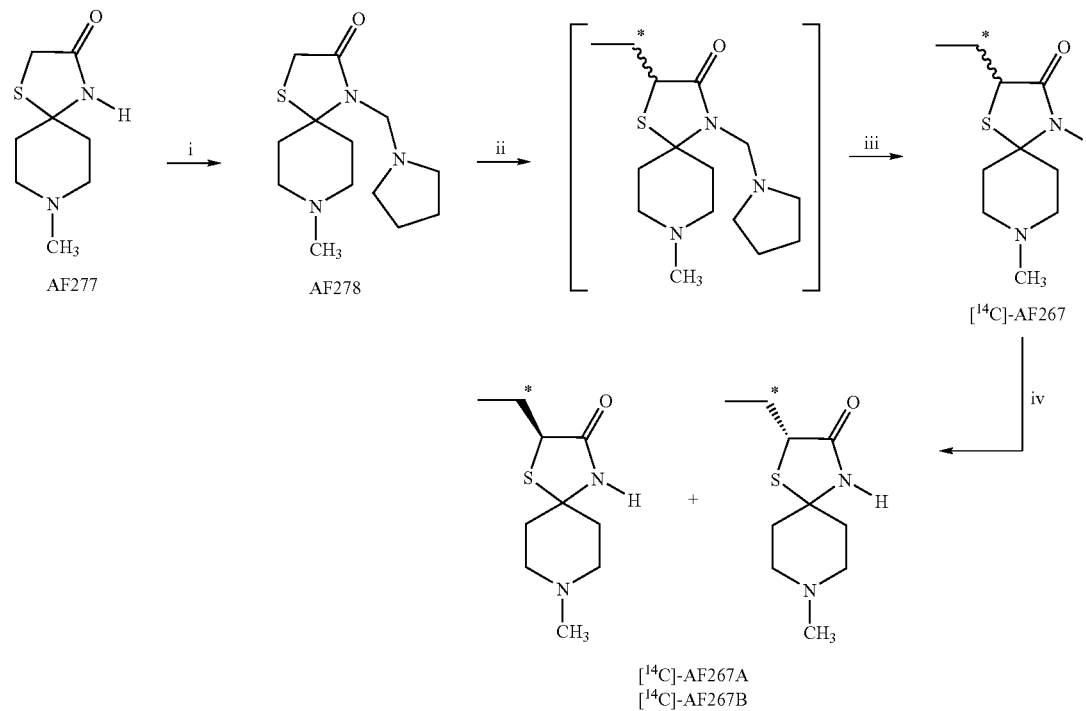

i. CH₂O, 
ii. LDA, THF-DMPU, CH₃*CH₂Br
iii. Silica-gel
iv. Chiral HPLC reaction may be illustrated as follows in Scheme 7, where the N-heterocyclic ketone is N—BOC-piperidine-4-one (BOC=tert-Butoxycarbonyl):

SCHEME 7

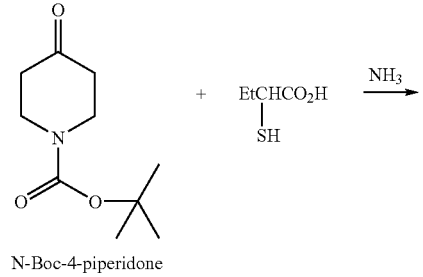

N-Boc-4-piperidone

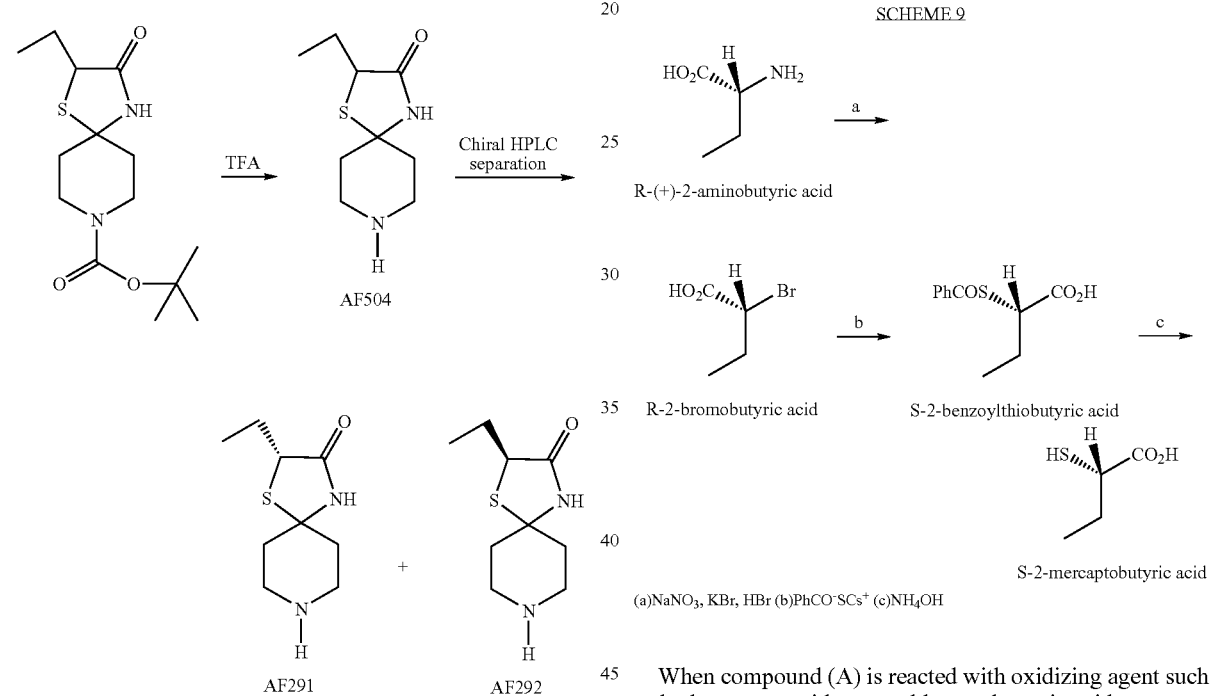

AF504

AF291          AF292

Stereospecific synthesis of structure (A) or (B) may also be obtained by reacting the corresponding N-heterocyclic ketone with the appropriate 2-mercaptocarboxylic acid, for example: when 1-methylpiperidine-4-one is reacted with (S)-2-mercaptobutyric acid and NH$_3$, AF267B is obtained, as shown in Scheme 8 [the (S) configuration is based on the x-ray crystallography of AF267B]:

SCHEME 8

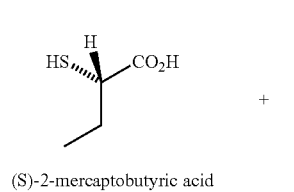

(S)-2-mercaptobutyric acid

-continued

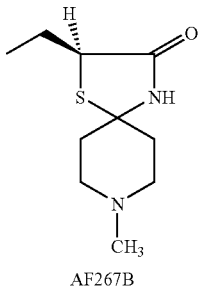

AF267B (S)-2-Mercaptobutyric acid is commercially available or is prepared from (R)-bromobutyric acid. This reaction may be illustrated as follows in Scheme 9:

SCHEME 9

R-(+)-2-aminobutyric acid

R-2-bromobutyric acid          S-2-benzoylthiobutyric acid

S-2-mercaptobutyric acid (a)NaNO$_2$, KBr, HBr (b)PhCO$^-$SCs$^+$ (c)NH$_4$OH

When compound (A) is reacted with oxidizing agent such as hydrogen peroxide or m-chloroperbenzoic acid, structure (D) or structure (E) is obtained as shown in Scheme 10:

SCHEME 10

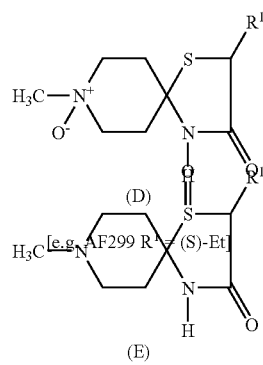

(D)

[e.g. AF299 R$^1$ = (S)-Et]

(E)

[e.g. AF300 R$^1$ = (S)-Et]

The thio analog of structure (A) or (B) may in general be obtained by reacting the corresponding thiazolidinone ring in structure (A) with Lawesson's reagent, for example as shown in Scheme 11:

SCHEME 11

(AF267)

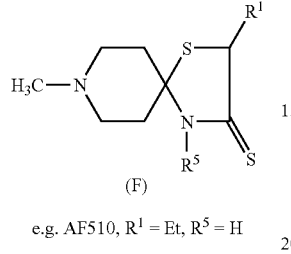

e.g. AF510, $R^1$ = Et, $R^5$ = H

Bivalent compounds containing essentially two ligands within the same molecule may be obtained by reacting the corresponding compound structure (A) with a spacer under the same conditions to obtained compound structure (B) as described earlier. The spacer-(leaving group) is exemplarily alkaneldihalide, alkanediol, alkanediacid, poly(ethylene glycol). This reaction may be illustrated as follows in Scheme 12:

SCHEME 12

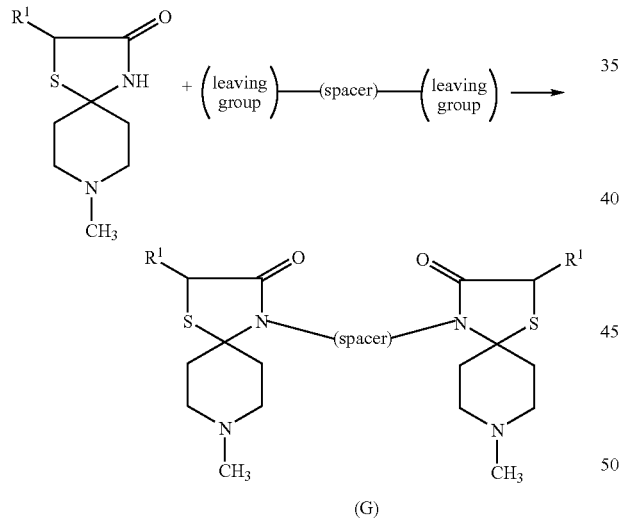

e.g. spacer = $(CH_2)_n$, $(CH_2CH_2O)_n$, n = 1–12
leaving group = Br, C(O)Cl, C(O)OH N-Phosphonooxymethyl prodrugs were reported in Krise et al, J Med. Chem. 42: 3094-3100 (1999). Such moieties of N-phosphonooxymethyl can be used also for synthesis of prodrug (H) for improving the water solubility of tertiary amine-containing compounds (B) as shown below. The tertiary amine in compound structure (B) undergoes a nucleophilic substitution reaction with di-tert-butyl chloromethyl phosphate which results in the formation of the quaternary ammonium phosphate protected prodrug. The free acid form of the prodrug is obtained after removal of the tertiary butyl groups as shown in Scheme 13:

SCHEME 13

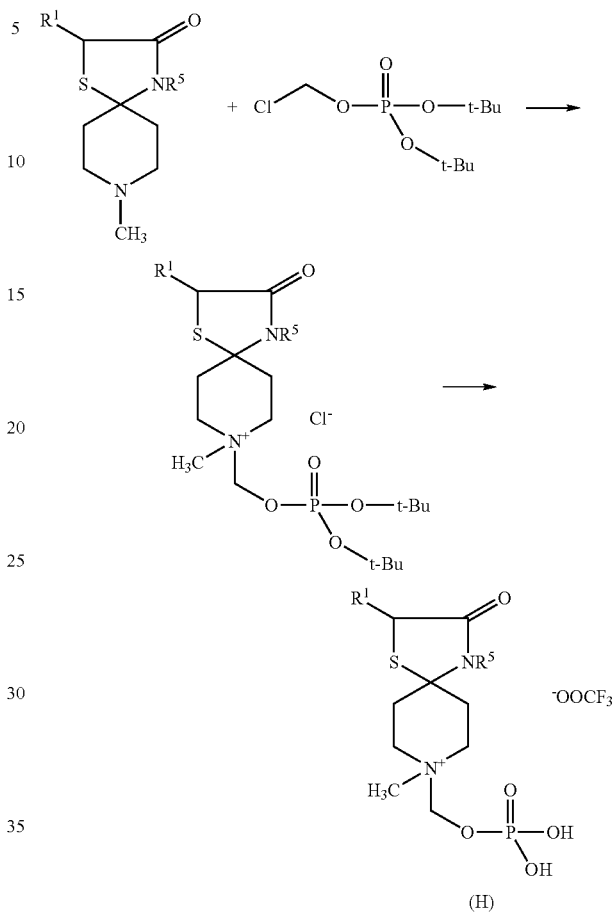

The nitrones, compounds of type (I) and (J), can be prepared by reacting the spiro-ketone with alkyl hydroxyl amine or aryl hydroxyl amine. These reactions may be illumed as follows in Schemes 14A and 14B:

SCHEME 14A (e.g. AF600: A = O, $R^1$ = Me, $R^5$ = Me; AF601: A = O, $R^1$ = Et, $R^5$ = Me; AF602: A = O, $R^1$ = Ph, $R^5$ = Me; AF604: A = O, $R^1$ = Me, $R^5$ = benzyl; AF605: A = O, $R^1$ = Me, $R^5$ = iPr)

SCHEME 14B

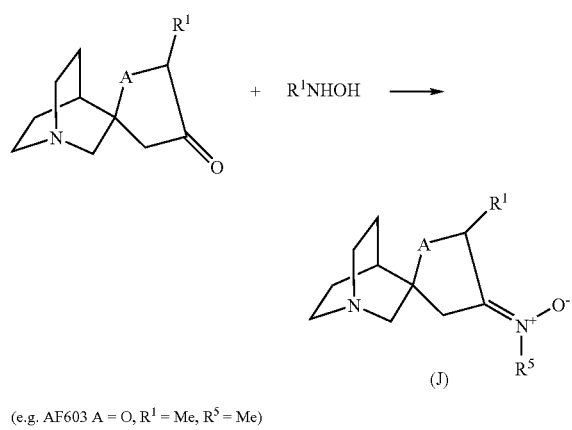

(e.g. AF603 A = O, R¹ = Me, R⁵ = Me)

Alternatively, structure (I) can be prepared by reacting a five-membered ring carbonyl with alkyl hydroxyl amine or aryl hydroxyl amine. The resulting nitrone is cyclized to form the Spiro structure.

The compound of formula

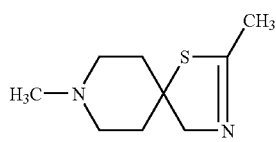

designated AF150(S), is described in U.S. Pat. No. 5,407,938. However, the synthesis of this compound has now been improved. The improved synthesis is described in the following scheme 15:

SCHEME 15

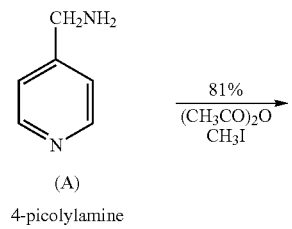

(A)
4-picolylamine

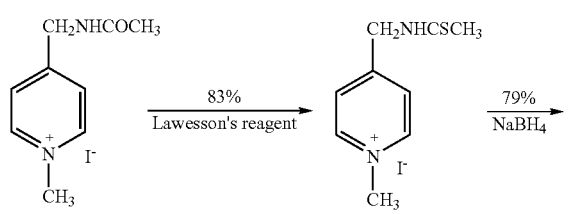

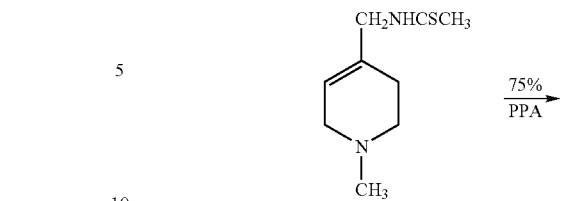

AF150(S)

AF150(S) was obtained by reaction of 4-picolylamine with acetic anhydride/methyl iodide, followed by reaction with Lawesson's Reagent. The obtained thiopyridinium iodide was reduced to give thioacetylamino-tetrahydropyridine which was cyclized to form AF150(S).

When prepared as a free base, AF150(S) is a colorless liquid. The free base may be stored cold (−20-0° C.) as a bulk material in dark storage under dry vacuum. AF150(S) may also be obtained as a salt. In an embodiment of the invention, citric acid is used to obtain a stable salt that can be used eventually in a large scale production. A white crystalline citric acid salt of AF150(S) was prepared by mixing AF150(S) free base with citric acid in 2-propanol and tetrahydrofuran solution. In comparison to the free base, the salt: (a) lacks color development even at high temperature (accelerated stability test), and (b) shows high stability if the bulk is kept under anhydrous conditions even at high temperature (accelerated stability test).

In another embodiment of the invention, AF150(S) is provided in pharmaceutical acceptable paraffin oil. The stability of 10% w/w AF150(S) in paraffin oil was examined at 40° C., under air or nitrogen atmosphere and in the presence or absence of tocopherol. No degradation products above 0.1% were detected. A slight yellow color was observed in samples without tocopherol but color was not developed in samples containing 0.5% w/w tocopherol in AF150(S).

It may noted that the N-methyl group in AF150(S) may be removed by reaction with m-chloroperbenzoic acid/FeCl$_2$ as shown in Scheme 16:

SCHEME 16

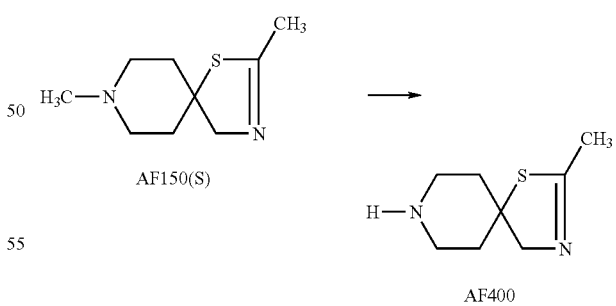

When AF150(S) is reacted with oxidizing agent such as m-chloroperbenzoic acid, AF406 is obtained.

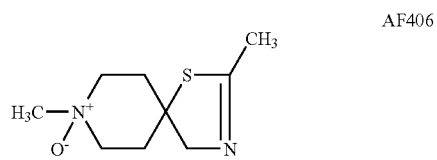

Cold simulation to $^{14}C$-labeling of AF150(S), AF402, was obtained by using $d_3$-iodomethane instead iodomethane in the first step of the synthesis, according to the scheme of the synthesis of AF150(S). The synthesis of AF402 is described in Scheme 17 below:

SCHEME 17

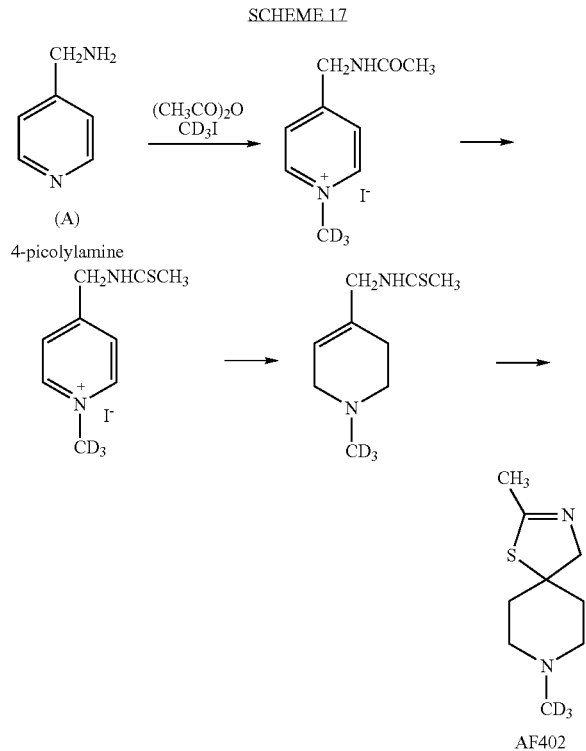

AF402

It is to be understood that whereas in the foregoing description, the illustrative compounds of the invention have shown piperidine, and quinuclidine rings, other any nitrogen-containing heterocyclic rings suitable for spiro-configuration with the depicted spiro five-membered ring may be substituted therefore. Such compounds may be made by using the corresponding ketone, in analogy to the use of 3- or 4-piperidone to obtain compounds shown above. A similar remark applies to the practical EXAMPLES, which are merely illustrative and not limitative.

The invention will now be illustrated by the following non-limiting EXAMPLES.

EXAMPLE 1

Synthesis of (S)-2-Ethyl-8-methyl-1-thia-4,8diaza-spiro[4.5]decan-3-one

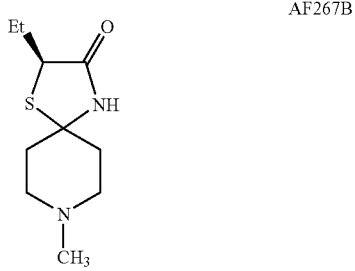

AF267B

Step 1: Synthesis of 2-mercaptobutyric acid

2-Bromobutyric acid (3.2 kg, 19.16 mol) was introduced in a cooled (ice-water bath) flask. It was stirred and aqueous potassium hydroxide (18.2 mol) was added gradually (0.5 h) while the temperature was maintained at 30-40° C. Cooling was stopped and potassium O-ethyldithiocarbonate (3.48 kg, 21.7 mol) was added in portions so that the temperature did not exceed 50° C. (0.5 h). The reaction mixture was stirred at 50° C. for 1 hour, then cooled to 15-20° C. (ice-water bath). Ethylenediamine (2.6 l, ~39 mol) was added during a period of 20 min while the temperature was maintained at 45-55° C. (external cooling). The resulting suspension was stirred at 50° C. for two hours, cooled to 20° C., filtered and the solid was washed with 2×1.5 liter warm water (40-50° C.). The aqueous filtrate and washings were combined, cooled below 20° C. (ice-water bath) and aqueous sulfuric acid [5.2 l, 50% (w/w)] was added slowly while keeping the temperature at 45-55° C. (0.5 hour, to pH=2). The solution was cooled to 30° C. and transferred to a 25 liter container equipped with a mechanical stirrer. Methyl-t-butyl ether (MTBE, 3 l) was added and the mixture stirred and left overnight at room temperature. The upper oily phase was separated and the lower aqueous phase was filtered under reduced pressure to remove a precipitate which was formed. The aqueous phase was extracted with ME, the extracts were combined and the MTBE was removed. The oily residue was dissolved in cyclohexane (5 l) and kept in a refrigerator overnight. A lower phase was formed. It was separated and extracted with cyclohexane. The cyclohexane extracts were combined with the upper phase, cyclohexane was removed and the 2-mercaptobutyric (crude) acid was dried in vacuum (54° C./2 mmHg) to yield 2-mercaptobutyric acid (2.18 kg, 18.16 mol).

Step 2: Synthesis of AF267 (racemate)

2-Mercaptobutyric acid (705 g, 5.88 moles) and a mixture of cyclohexane/tert-butyl alcohol (1;3.5(w/w), 4.3 l) were introduced into a flask. The solution obtained was stirred and heated to 40-60° C. Gaseous ammonia was bubbled through the solution till all or most of the 2-mercaptobutyric acid was converted to its ammonium salt. The bubbling of the ammonia was stopped, the reaction mixture was heated to reflux and a solution of 1-Methyl-4-piperidone (496 g, 4.39 mol) in a cyclohexane/tert-butyl alcohol mixture (500 ml) was added. After 1 hr, the solution become clear and the bubbling of ammonia was renewed and after 13 hrs (addition of piperidone and reaction time afterwards) the reaction mixture was cooled and left overnight at room temperature. Hydrochloric acid solution prepared by diluting aqueous concentrated acid (one volume) with water (two volumes) (960 ml) was added and the mixture stirred for 1 h. The solution obtained (pH~2-3) was cooled to 25° C. and the lower aqueous phase was separated and made basic with aqueous potassium hydroxide (pH~8.5-9) then left overnight at room temperature. The product which precipitated was filtered and washed with cold water (100 ml) to give wet powder. The filtrate was basified to pH 9 and left overnight at 5 ° C., filtered and washed with 50 ml cold water to give 72 g powder. The same procedure was repeated to synthesize a second batch of AF267 (multiplied by a factor of 1.2). The corps were combined to give 1.6 kg of wet product The crude combined product was dissolved in 4.5 liter of hot water (95° C.), filtered and the clear solution was left at room temperature for 10 hrs, filtered and dried for 24 hrs (50° C., 1 mmHg) to give AF267 (1.048 kg, 50.7% yield). The filtrate was concentrated, cooled overnight at 5° C., filtered, washed (100 ml cold water) and dried to give AF267 (215 g, 10.4% yield). Total AF267 yield: 61%. mp. 142-144° C.; $^1H$ NMR (CDCl$_3$) δ 1.02 (t, j=7.3 Hz, CH$_3$CH$_2$), 1.7-1.8 (m, CH$_3$CHH), 1.96-2.07 (m), 2.30 (s, NCH$_3$), 2.3-2.36 (m, 2H), 2.6-2.7 (bs, 2H), 3.80 (dd, j=8.7, 3.9 Hz, 1H, SCH) ppm. MS m/e 214(M$^+$), 181(M$^+$-SH); Anal. (C$_{10}$H$_{18}$N$_2$OS) calcd. C 56.04, H 8.47, N 13.07, S 14.96; found C 55.92, H 8.44, N 13.23, S 14.81.

Step 3: Chiral Separation of AF267B and AF267A

Prochom LC 110 High Performance Preparative Liquid Chromatograph

Column: CHIRALPAK®ASV (lot number JG 001)

Pump flow rate: 500 ml/min

Pressure: 12.7 bar

Column Temp 26° C.

Moblie phase: Acetonitrile/EtOH 85:15

Concentration: 37 gr/l

UV Detection: 240/230 nm

Following elution the eluent was evaporated to dryness.

First eluting enantiomer (AF267A): ee: 99.7 (687.1 gr, purity 99.3%; Yield: 97%)

Second eluting enantiomer (AF267B): ee: 99.8 (694.9 gr; 99.9% ; Yield: 98%).

Residual solvent (e.g. acetonitrile) was removed by further addition of ethanol and evaporation to dryness.

By analogous syntheses, AF292 and other related compounds may be prepared.

EXAMPLE 2

X-Ray Single Crystal Structure Analysis of (S)-2-Ethyl-8-methyl-1-thia-4,8-diaza-spiro[4.5]decan-3-one (AF267B)

Crystal data: $C_{10}H_{18}N_2OS+H_2O$ (monohydrate), transparent, light yellow, prisms, crystal size $0.2 \times 0.2 \times 0.4$ mm$^3$; crystal system, orthorhombic, space group: P212121 (No 16) a=10.394 (10) (α90°), b=20.133 (2) (β=90°), c=5.856 (4) (γ=90°), Å, from 25 reflection, T=110K, Volume=1224.2 (9) Å$^3$, Z=4, Fw=202.32, Calculated density, Dc=1.092 Mg/m$^3$, Absorption coefficient, μ=0.232 mm$^{-1}$.

Data collection and treatment: Rigaku AFC5R four-circle diffractometer, MoKα, graphite monochromator (λ=0.71073 Å), 11461 reflections collected, Theta range for data collection: $2.82° \leq \theta \leq 27.53°$; Index ranges: $-13 \leq h \leq 13$, $-26 \leq k \leq 26$, $0 \leq l \leq 7$, ω scan method, scan width=1.2°, scan speed 2°/min, typical half-height peak width=0.45°, 3 standards collected 62 times each, with a 3% change of intensity; Reflections collected: 6272 measurements, 2833 independent reflections [R (int)=0.0604, Bijvoet reflections kept separated].

Solution and refinement: structure solved by direct methods (SHELXS-97). Full-matrix least-squares refinement based on F$^2$ (SHELXL-97). Idealized hydrogens were placed and refined in a riding mode, water hydrogens found from the difference Fourier map, 148 parameters; final R indices: $R_1$=0.0671 (based on F$^2$) for data with I>2 sigma(I) wR$^2$=0.1484 and $R_1$=0.0747 wR$^2$=0.1553 for all data, goodness-of-fit on F$^2$=1.13, largest electron density=0.745 e/$^{-3}$ around S atom.

Absolute configuration: The absolute configuration of the molecule was determined using Flack's parameter approach and the alternative refinement of the enantiomeric twinning component. Both methods show unequivocally that the present coordinates belong to the correct absolute configuration (S enantiomer). The cystals of this compound were prepared from crystallization in toluene/petroleum ether/methanol.

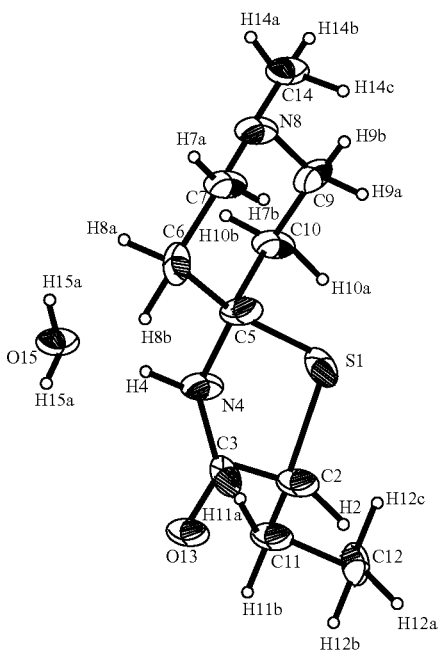

Structure 1: ORTEP structure of $C_{10}H_{18}N_2OS + H_2O$

EXAMPLE 3

Chiral Synthesis of (R)-2-Ethyl-8-methyl-1-thia-4,8-diaza-spiro[4.5]decan-3one, AF267A

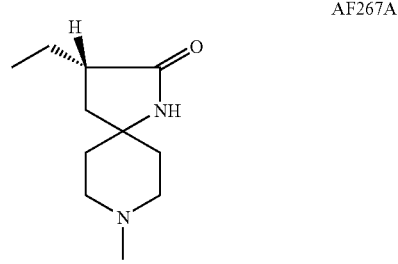

AF267A

The asymmetric synthesis of AF267A was performed in order to model the synthesis of the S enatiomer by using optically active 2-mercaptobutyric acid in the synthesis of AF267. Optically active 2-mercaptobutyric acid was synthesized starting from L-(+)-2-aminobutyric acid (I) which has the S configuration. The amino acid was converted to (S)-2-bromobutyric acid (II) with retention of configuration by treatment with sodium nitrite, potassium bromide and hydrobromic acid. The enantiomeric purity of the obtained bromide was checked by proton NMR measured in the presence of (R)-(+)-N-benzyl-α-methyl-benzylamine and compared to the spectrum of the racemic bromide measured at the same conditions. The presence of only one enantiomer was detected by this method. The bromide was converted to (R)-2-benzoylthiobutyric acid (III) (with inversion of configuration) by treatment with cesium thiobenzoate in DMF. Debenzoylation of (III) was accomplished without racemization by aminolysis (1N ammonium hydroxide at room temperature).

The obtained (R)-2-mercaptobutyric acid was purified by distillation and then reacted with ammonium acetate and 1-methyl-4-piperidone in boiling cyclohexane. The crude reaction mixture was analyzed by GC on a chiral column and found to contain AF267A accompanied by a small (2-3%) amount of AF267B.

EXAMPLE 4

Chiral Synthesis of (S)-2-Ethyl-8-methyl-1-thia-4,8-diaza-spiro[4.5]decan-3-one AF267B This compound is obtained as in EXAMPLE 3, except that the starting material used is (R)-2-bromobutyric acid.

EXAMPLE 5

Synthesis of (S)-2-Ethyl-1-thia-4,8-diaza-spiro[4.5]decan-3-one, AF292

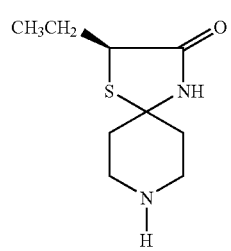

AF292

To a cooled (ice-salt bath) stirred solution of AF267B (6.1 gr, 0.028 mol) in dichloromethane (60 ml) was added m-chloroperbenzoic acid (mCPBA) in small portions over a period of 15 min mCPBA (70%, 7.02 gr, 0.028 mol total). The mixture was stirred for 1 hr and then treated with iron (II) chloride (2.14 ml of 1M solution in water). Stirring and cooling (−10 ° C.) were continued for 1 hr and then stirring continued for 2 hrs at room temperature. Ethylene diamine (1.9 ml, 0.285 mol), sodium hydroxide (30.5 ml of 2N aqueous solution), and petroleum ether 40-60° C. (60 ml) were added. After vigorous shaking the layers were separated, the aqueous layer was extracted with mixture of dichloromethane/petroleum ether 1:1 (600 ml) followed by dichloromethane (first 600 ml then 300 ml). The combined extracts were dried (Na$_2$SO$_4$), filtered and the solvents were removed under reduced pressure. Flash chromatography (silica-gel 60, 230-400 mesh, Merck 1.09385, elution with methanol/chloroform/ammonium hydroxide 10:89:1 v/v) of the residue gave AF292. $^1$H NMR (CDCl$_3$) δ 1.02 (t, j=7 Hz, 3H), 1.76 1.92 and 2.07 (3xm, 6H), 2.84 (m, 2H), 3.04 (m, 2H), 3.83 (dd, j=8.8, 4 Hz, 1H), 7.66 (NH) ppm; $^{13}$C NMR (CDCl$_3$) δ 11.50, 27.24, 42.87, 43.95, 44.10, 48.80, 64.22, 175.22 ppm: MS m/e 200(M$^+$). The compound was >99.9% purity by HPLC, GC.

The hydrochloride salt of AF292 was formed by addition of HCl (4M in methanol) and recrystallised from methanol-diethyl ether to give a white precipitate that was filtered and dried. $^1$H NMR (D$_2$O) δ 0.78 (t, j =7.3 Hz, 3H), 1.58 (m, 1H), 1.76 (m, 1H), 2.05 (m, 4H), 3.07 (m, 2H), 3.30 (m, 2H), 3.92 (dd, j=7.9, 4.0 Hz, 1H) ppm.

EXAMPLE 6

Reactions for Preparation of [$^{14}$C]-2-Ethyl-8-methyl-1-thia-4,8-diaza-spiro[4.5]decan-3-one: R and S isomers

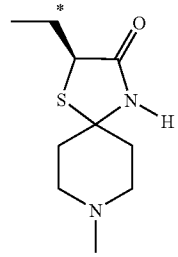

[$^{14}$C]-AF267B

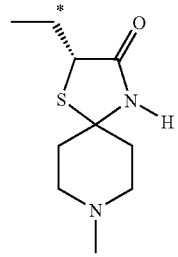

[$^{14}$C]-AF267A

In a septum-capped dried flask (10 ml) equipped with a magnetic bar and nitrogen inlet, a solution of diisopropylamine (0.078 ml, 0.56 mmol) in dry THF (1.4 ml) is introduced by a syringe and cooled to 0° C. n-BuLi (0.9 M in hexane, 0.62 ml, 0.56 mmol) is added, the reaction mixture is stirred at 0° C. for 20 min and then cooled to −78° C. A solution of AF287 (0.1375 gr, 0.51 mmol) in dry THF (0.4 ml) and dry N,N'-dimethyl-N,N'-propylene urea (DMPU) (0.6 ml) is added dropwise (30 min) and the reaction mixture is stirred for 20 min at −78° C. Ethyl bromide (0.043 ml, 0.56 mmol) labeled at the 1-carbon with $^{14}$C is added in one portion, the temperature is allowed to rise to room temperature and the reaction mixture is stirred for an additional 4 h. The solvents are removed under reduced pressure, first using a water pump at 25° C. for 20 min and then an oil pump (~4 mm Hg) at ~60° C. for ~30 min (using a needle which introduced a stream of air to remove the solvent faster). Flash chromatography of the residue gives racemic AF267 (95 mg, ~86% yield). Preparative chiral HPLC may be used to separate the enantiomers. By following the above procedure using ethyl bromide which was not labelled, preparative HPLC of 60 mg of the racemate obtained after flash chromatography afforded non-isotopically labeled AF267B (17.6mg).

EXAMPLE 7

Synthesis of (S)-2-Ethyl-8-methyl-8-oxy-1-thia-4,8-diaza-spiro[4.5]decan-3-one, AF299

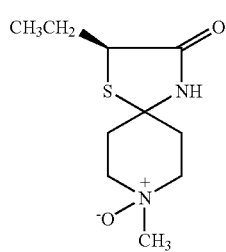

AF299

A solution of mCPBA (70%, 2.62 gr, 10.64 nmmol) in dichloromethane (40 ml) was added slowly (0.5 hr) to a cold (0° C.) and stirred solution of AF267B (2.07 gr, 9.67 mmol) in dichloromethane (40 ml). The cooling bath was removed and the reaction mixture was stirred at room temperature for 2 hrs and then the solvent was removed under reduced pressure. Flash chromatography (methanol/chloroform/ammonium hydroxide 10:89:1 v/v) of the residue and precipitation of the product as a solid from methanol-acetonitrile gave the N-oxide, AF299; $^1$H NMR (CDCl$_3$) δ 0.99 (t, j=7.3 Hz CH$_3$CH$_2$), 1.74 and 2.09 (2m, CH$_3$CH$_2$), 1.82 (m, 2H), 3.9 (m, 2H), 3.36 (s, CH$_3$N$^+$), 3.33-3.45 (m, 4H), 3.78 (br NH), 3.83 (dd, j=3.74, 8.84 Hz, CH$_3$CH$_2$CH) ppm; MS m/e 230 (M$^+$).

EXAMPLE 8

Synthesis of (S)-2-Ethyl-8-methyl-1-oxo-1λ$^4$-thia-4,8-diaza-spiro[4.5]decan-3-one, AF300

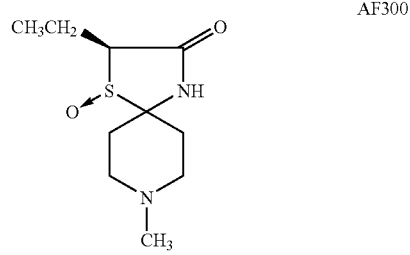

AF300

A solution of AF267B (1.72 gr, 0.008 mol) in water (2.5 ml) was cooled (ice-water bath) and trifluoroacetic acid (3.5 ml) was added. To the cold stirred obtained mixture was added hydrogen peroxide (30%, 0.57 ml, 0.008 mol), the cooling bath was removed and the reaction mixture was stirred at room temperature over night Sodium sulfite was added and the pH of the solution was adjusted to 9 with a saturated solution of sodium carbonate. The aqueous phase was extracted with dichloromethan (2×100 ml) and then with ethyl acetate (1×50 ml). The organic extracts were combined, dried (MgSO$_4$) and the solvent was evaporated. Flash chromatography (silica-gel 60, 230-400 mesh, Merck 1.09385, elution with methanol/chloroform/ammonium hydroxide 10:89:1 v/v) gave AF300. $^1$H NMR (CDCl$_3$) δ 1.19 (t, j=7.3 Hz, 3H, CH$_3$), 1.85-2.0 (m, 5H), 2.17 (m, 1H), 2.27 (m, 1H), 2.34 (s, 3H, NCH$_3$), 2.6 (m, 2H), 3.30 (dd, j=3.56, 11.13 Hz,: CH$_3$CH$_2$CH), 6.37 (br NH) ppm; MS (EI) m/e 230 (M$^+$).

EXAMPLE 9

Synthesis of 2-(1-Hydroxy-ethyl)-8-methyl-1-thia-4,8-diaza-spiro[4.5]decan-3-one (AF298)

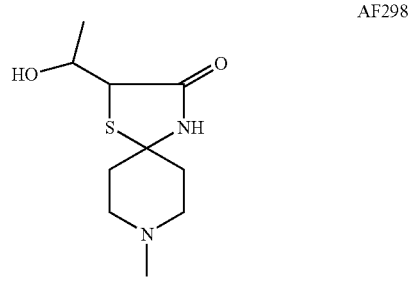

AF298

To a cold (0° C.) solution of diisopropylamine (0.28 ml, 0.002 mol) in dry THF (12 ml) under argon atmosphere was added a solution of n-butyllithium (1.4M in hexane, 1.4 ml, 0.002 mol), the mixture was stirred for 20 min and then cooled to −78° C. A solution of AF287 (0.41 g, 0.0015 mol) in THF (3 ml) was added dropwise (10 min) and the resulting mixture was stirred at −78° C. for additional 10 min. Acetaldehyde (0.85 ml, 0.015 mol) was added in one portion and after ten min at −78° C. acetic acid (0.11 ml, 0.002 mol) was added in one portion and the temperature was allowed to raise to room temperature. The reaction mixture was added to chloroform (200 ml) and the organic phase was washed with water (2×20 ml), separated and dried. The solvent was evaporated and flash chromatography (silica, CHCl$_3$/MeOH/NH$_4$OH 80/20/1) of the residue gave AF298 (0.132 g). $^1$H-NMR (CDCl$_3$) δ 1.24 (d, j=6.05 Hz, 3H, CH$_3$), 1.7-2.2 (m, CH$_2$), 2.31 (s, 3H, NCH$_3$), 2.60-2.80 (m, CH$_2$), 3.71 (d, j=9.4 Hz, 1H, SCM), 3.94-4.04 (m, 1H, CHO), 4.75-4.9 (br OH), 7.1-7.2 (br NH) ppm. MS m/e 230 M($^+$).

EXAMPLE 10

Synthesis of (S)-2-Ethyl-4-(4-fluoro-benzenesulfonyl)-8-methyl-1-thia-4,8diaza-spiro[4.5]decan-3-one, AF700

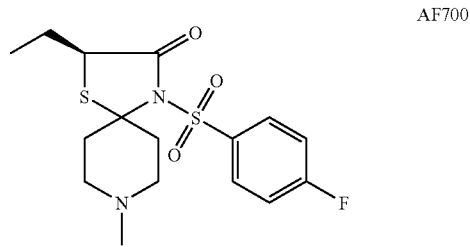

AF700

Into a cold (0° C., ice-water bath) solution of lithium hexamethyldisilazane (8 ml, 1M in THF) was added AF267B (1.5 g, 0.007 mol) in small portions over a period of 15 min under argon atmosphere. The cooling bath was removed and the reaction mixture was stirred at room temperature for 40 min. 4-fluorobenzylsulfonyl chloride (1.37 g, 0.007 mol) was added (during the addition the temperature was kept below 20° C., cooling bath) and the reaction mixture was left at room temperature under argon atmosphere overnight. Dichloromethane (100 ml) was added. The reaction mixture was washed with water (20 ml) the organic phase was separated, dried (MgSO$_4$) and evaporated. Flash chromatography (silica, ethyl acetate/methanol/aqueous ammonia 10/2/0.1) gave AF700 (0.46 gr, 0.0015 mol). $^1$H-NMR (CDCl$_3$, 300 MHz) δ 0.94(t, j=7.14 Hz, 3H CH$_3$), 1.64-1.77(m, 3H, CHH+CH$_2$), 1.88-2.00(m, 3H, CHH+CH$_2$), 2.15-2.29(br, 2H, CH$_2$), 2.29(s, 3H, NCH$_3$), 2.51-2.60(br, 2H, CH$_2$), 4.24(dd, j=7.99, 3.72 Hz, 1H, SCH), 7.21(app. t, j=8.53 Hz, 2H, Ar), 8.07-8.12(m, 2H, Ar).

EXAMPLE 11

Synthesis of 8-Methyl-4-pyrrolidin-1-ylmethyl-1-thia-4,8-diaza-spiro[4.5]decan-3-one, AF287

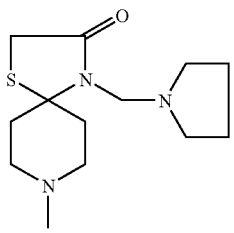

AF287

A solution of 8-Methyl-1-thia-4,8-diaza-spiro[4.5]decan-3-one (AF277 5.13 g, 0.0275 mol), formaldehyde (37% solution, 2.75 ml), and pyrrolidine (2.3 ml, 0.0275 mole) in ethanol (2.3 ml) was refluxed for 4 h, then left at room temperature over night. Toluene (10 ml) was added and the solvent was evaporated. Boiling pentane (100 ml) was added to the residue and the solution was decanted. The trituration with hot pentane was repeated four times, the pentane layers were combined, cooled to 0° C. and the precipitate was collected and identified as AF287 (4.6 gr, 63% yield). $^1$H-NMR (CDCl$_3$) δ 1.69-1.77(m, 5H), 2.20-2.29(s and m, 5H, CH$_3$ and CH$_2$), 2.43-2.58(m, 6H), 2.82-2.86(m, 2H), 3.50 (s, 2H, SCH$_2$), 4.14(s, 2H, NCH$_2$N)ppm. MS (EI) m/e 269(M+); 198; 84; 70.

EXAMPLE 12

Synthesis of 2-Ethyl-4(3-1H-indol-3-yl-propionyl)-8-methyl-1-thia-4,8-diaza-spiro[4.5]decan-3-one, AF704

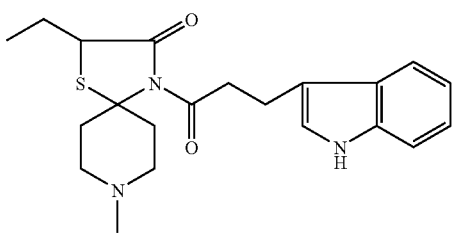

AF704

A solution of AF267 (1.2 gr, 0.0056 mol), 3-indolpropionic acid (1.37 gr, 0.0072 mol), dicyclohexylcarbodiimide (DCC) (1.57 gr, 0.0076 mol) and 4-dimethylaminopyridine (DMAP) (0.93 gr, 0.0076 mol) in dichloromethane (120 ml) was stirred at room temperature for 3 days. The reaction mixture was washed with water (2×40ml), the organic phase was dried and evaporated. Flash chromatography (silica, CHCl$_3$/MeOH/NH$_4$OH 90/10/1) gave the title compound which was triturated in acetone. The solution was filtered to remove the impurities, then the acetone was evaporated and the obtained thick oil was triturated in ether. The obtained solid (AF704), 400mg, was filtered and dried. Mp. 122.5-124.5° C.; $^1$H-NMR (CDCl$_3$) δ 1.01 (t, j=7.4 Hz, 3H, CH$_3$CH$_2$), 1.50 (m, 1H), 1.59 (m, 1H), 1.61-1.73 (m, 1H, CH$_3$CHH), 2.1-2.15 (m, 1H, CH$_3$CHH), 2.18 (dt, j=12.4, 2.4 Hz, 1H), 2.29 (s, 3H, NCH$_3$), 2.33 (m, 1H), 2.83 (m, 2H), 2.99 (dt, j=12.55, 4.39 Hz, 1H), 3.01 (t, J=7.42 Hz, 2H, CH$_2$), 3.16 (dt, j=12.7, 4.39 Hz, 1H), 3.28 (m, 2H), 3.67 (dd, j=8.9, 4.18 Hz, 1H, SCH), 7.04 (br s, C═CH), 7.11 (t, j=7.8 Hz, ArH), 7.18 (t, j=7.1 Hz, ArH), 7.34 (d, =8.08 Hz, ArH), 7.64 (d, j=7.58 Hz, ArH), 8.01 (br NH) ppm; MS (EI) m/e 385 M($^+$), 214, 181, 171,143, 130 (100%).

When the starting material is AF267B, the enantiomer AF704B is obtained.

EXAMPLE 13

Synthesis of 2-Ethyl-4-[2-(1H-indol-3-yl)ethyl]-8-methyl-1-thia-4,8-diaza-spiro[4.5]decan-3-one, AF703

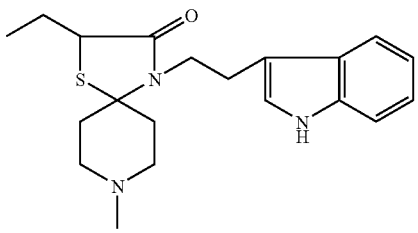

AF703

In a three-necked flask equipped with a magnetic stirrer and Dean-Stark and dropping funnel a solution of 2-mercaptobutyric acid (7.38 gr, 0.065 mol) in a mixture of t-butanol/cyclohexane (30/104 gr/gr, 86 ml) was heated to 40° C. Tryptamine (10.8 gr, 0.068 mol) was added in four portions (20 min), the reaction mixture was stirred for additional 45 min. and then heated to reflux. A solution of 1-methyl-4-piperidone (6.18 ml, 0.049 mol) in t-butanol/cyclohexane (30/104 gr/gr, 10 ml) was added dropwise during 40 min and the reflux continued for 5 hrs (1 ml water was collected). Mixture of HCl/water (2:2 v/v) was added until pH 2-3, the aqueous phase was separated, basified to pH 10 with solution of potassium hydroxide and extracted with dichloromethane. The organic phase was separated, dried and the solvent was evaporated. Flash chromatography (silica, CHCl$_3$/MeOH/NH$_4$OH 90/10/1) of the residue gave the title compound. Recrystallization from boiling hexane gave pure AF703. $^1$H-NMR (CDCl$_3$) δ 1.04 (t, j=7.35 Hz, 3H, CH$_3$), 1.65-1.68 (m, 2H), 1.71-1.80 (m, 1H, CH$_3$CHH), 2.13-2.34 (m, 5H), 2.31 (s, 3H, NCH), 2.86 (m, 2H), 3.05-3.10 (m, 2H), 3.41-3.49 (m, 1H), 3.51-3.65 (m, 1H), 3.80 (dd, j=8.8, 3.9 Hz, 1H, SCH), 7.02 (d, j=2.32 Hz, 1H, ArH), 7.14 (ddd, j=7.35, 7.35, 1.17 Hz, 1H, ArH), 7.20 (ddd, j=7.45, 7.45, 1.39 Hz, 1H, ArH), 7.35 (d, j=7.4 Hz, 1H, ArH), 7.77 (d, j=7.42 Hz, 1H, ArH), 8.03 (brNH) ppm.

EXAMPLE 14

Synthesis of 2,8-Dimethyl-1-thia-3,8-diaza-spiro[4.5]dec-2-ene AF150(S)

AF150(S)

Step 1: Synthesis of 4-(acetaminomethyl)-1-methyl-pyridinium iodide

To a cold (ice-water bath) solution of 4-picolylamine (1070 gr, 9.9 mol) in methanol (3 l) was added dropwise acetic anhydride (1400 gr, 13.7 mol). During addition the reaction temperature was kept between 10 and 30° C. When the addition of the reagent was complete the reaction mixture was left overnight at room temperature. Iodomethane (800 ml, 24.8 mol) was added to the reaction mixture which was cooled with water bath, under nitrogen atmosphere. During addition the reaction temperature was kept below 25° C. When the addition was complete, the reaction mixture was protected from light and left at room temperature overnight The excess iodomethane was evaporated, crystallization was induced, the reaction mixture was cooled (ice bath) and isopropanol (1.5 l) was added. The reaction mixture was left at −30° C. overnight, the precipitate was filtered off, washed with isopropanol and dried. 4-(Acetaminomethyl)-1-methyl-pyridinium iodide (2043 gr, 7 mol) was obtained as yellow powder (71% yield). $^1$H-NMR (D$_2$O) δ 2.10 (s, CH$_3$CO), 4.32 (s, CH$_3$N$^+$), 4.63 (s, CH$_2$NHCO), 7.89 (d, j=6.6 Hz, 2H), 8.67 (d, j=6.6 Hz, 2H) ppm.

Step 2: Synthesis of 1-methyl-4-N-thioacetylaminomethylpyridinium iodide

A stirred solution of 4-(Acetaminomethyl)-1-methyl-pyridinium iodide (1.92 kg, 6.5 mol) and Lawesson's reagent (1.87 kg, 4.6 mol) in acetonitrile (6 l) was warmed to 80° C. for 17 hrs. Then the reaction mixture was cooled to room temperature and stirred for an additional 4 hrs. The crude 5 thioamide was filtered off and washed with acetonitrile (2.8 l). To the obtained thioamide was added ethyl acetate (10 l) and the suspension was refluxed for1 h. At 72-73° C. a noxious gas was evolved and trapped with NaOH solution. The suspension was cooled to 60° C. The thioacetamaide was filtered off, washed with ethyl acetate (2 l) and dried (45° C.). 2 kg of thioamide was obtained.

Step 3: Synthesis of 1-methyl-4-N-thioacetylamino-1,2,3,6-tetrahydropyridine

A suspension of 1-methyl-4N-thioacetylaminomethylpyridinium iodide (2.07 kg, 6.7 mol) in water (6.2 l) was prepared in 25 l flask and stirred at room temperature. A solution of sodium borohydride (383 gr, 10.1 mol) in water (1.2 l) was added dropwise over a period of 3.5 h so that the temperature was maintained below 32° C. The reaction mixture was stirred for 2 h at room temperature, ethanol (600 ml) was added and stirring was continued for 30 min. Sodium carbonate (780 g) was added and the reaction mixture was stirred overnight. Dichloromethane (4 l) was added, and stirring was continued for 45 min. The solution was filtered in order to remove the solid which was washed with chloroform (1 l) and water (0.5 l). The filtrate was decanted, and the aqueous phase was extracted with chloroform (2.5 l). The organic phases were combined and washed with 10% sodium thiosulfate solution (2.2 l). The aqueous phase was extracted with chloroform (1 l), the organic phases were combined, dried over magnesium sulfate, filtered and concentrated. Acetone (1.5 l) was added, the suspension was stirred for 30 min at room temperature and for 45 min at 0° C. The thioacetamide was filtered off, washed with acetone (1.5 l) and dried (50° C.). 860 gr of thioamide was obtained. mp. 140° C; $^1$H NMR (CDCl$_3$) δ 2.21 (m, 2H), 2.36 (s, CH$_3$N), 2.56 (s, CH$_3$CS), 2.57 (t, 2H), 2.95 (m, 2H), 4.23 (d, CH$_2$NH), 5.65 (m, CH=C), 7.41 (bs, NH) ppm. MS m/e 184 (M$^+$), 151, 150, 149, 141, 140, 126, 114, 109 (100%), 109, 96, 94, 82, 70.

Step 4: Synthesis of 2,8-dimethyl-1-thia-3,8-diaza-spiro[4.5]dec-2ene AF150(S)

In three-necked round bottom flask (5 l) equipped with a mechanical stirrer, polyphosphoric acid (2.1 kg) was stirred and heated to 100° C. The thioacetamide (840 gr) was added in small portion. At the end of the addition the temperature was raised to 170° C. and this temperature was maintained for 2-3 hrs. The hot reaction mixture was slowly poured into a stirred cold aqueous solution of sodium carbonate (25%, 10 l). The basicity was raised by addition of aqueous sodium hydroxide solution (50%, 350 ml). The reaction mixture was extracted with chloroform (2×3 l), the organic phases were combined, dried (Na$_2$SO$_4$) and evaporated. The residue was dissolved in petroleum ether (3.5 l) to give a solution and small amount of insoluble material. Evaporation of the petroleum ether solution grave crude AF150(S). The described procedure was repeated and the crude AF150(S) from the combined batches was treated with activated carbon and was distilled twice under reduced pressure (0.5 mmHg, 61° C.) to give AF150(S) (>1.2 Kg, global yield of 40%). $^1$H NMR (CDCl$_3$) δ 1.8-2.0 (m, 4H), 2.18 (t, 3H, CH$_3$C), 2.28 (s, 3H, CH$_3$N), 3.9 (m, 2H, CH$_2$) ppn; IR (C=O) 1636 cm$^{-1}$; MS. M/e 184 (M$^+$).

EXAMPLE 15

Synthesis of 2,8-Dimethyl-1-thia-3,8-diaza-spiro[4.5]dec-2-ene 8-oxide AF406

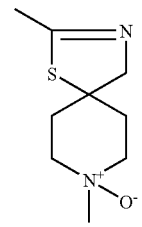

AF406

A solution of m-chloroperbenzoic acid, mCPBA, (1.40 gr, 8.11 mmol) in dichloromethane (30 ml) was added gradually to a solution of AF150(S) (1.45 gr, 7.88 mmol) in dichloromethane (10 ml). The reaction was stirred at room temperature overnight Chromatography of the reaction mixture was on a column of natural aluminum oxide (Merck)(metanol:chloroform 1/49) gave AF406 (0.75 gr) as a crystalline solid. A sample was crystallized from ethylacetate. A very hygroscopic solid was obtained. mp. 130-132° C. (145-159° C. dec.); $^1$H NMR (300 MHz, CDCl$_3$) δ 1.89 (m, 2H), 2.2 (t, j=1.5 Hz, CH$_3$C=N), 2.82 (m, 2H), 3.24 (m, 2H), 3.25 (s, CH$_3$N$^+$O$^-$), 3.35 (m, 2H), 4.03 (q, j=1.5 Hz, CH$_2$N=C) ppm; IR(CHCl$_3$) 2947, 1636, 1448, 1153, 931, 664 cm$^{-1}$; MS(EI) 200 (M$^+$), 184, 182, 149, 141, 140, 126, 110, 109, 108, 96, 82, 70.

EXAMPLE 16

Synthesis of 2-Methyl-1-thia-3,8-diaza-spiro[4.5]dec-2-ene. AF400

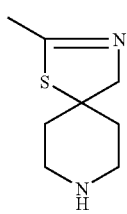

A solution of AF406 (2 gr, 0.01 mol) in chloroform (10 ml) was cooled to −10° C.−−5° C. in an ice-salt bath. A solution of FeCl$_2$ (1M, 0.7 ml) was added and the two phase reaction mixture was stirred for 4.5 h. The color of the reaction mixture changes with time from dark green to dark orange-brown. To the cooled reaction mixture was added cautiously a mixture of petroleum-ether (10 ml), ethylene diamine (600 mg, 0.01 mol) and 2N sodium hydroxide (10 ml, 0.02 mol). The pH of the water phase was 13. The organic was separated and the aqueous phase was extracted with chloroform, acidified with 5N HCl to pH=9 and extracted again with chloroform. All the organic fractions were combined, dried on potassium carbonate, filtered and evaporated. Chromatography [silica-gel (RIEDEL DE Haen 31607), CHCl$_3$:MeOH:NH$_4$O 90/9/1] of the residue gave AF400. mp. 40° C.; $^1$H NMR (CDCl$_3$) δ 1.74(m, 2H), 1.92 (m, 2H), 2.19 (t, j=1.8 Hz, 3H), 2.71 (m, 2H), 3.05 (m, 2H), 3.92 (q, j=1.8 Hz, 2H) ppm; MS m/e 171 (M$^+$+1), 170 (M$^+$).

EXAMPLE 17

Synthesis of 2-Methyl-8-methyl-d$_3$-1-thia-3,8-diaza-spiro[4.5]dec-2-ene, AF402

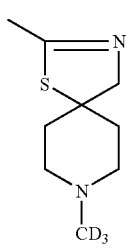

To a stirred cold (ice-water bath) solution of 4-picolyamine (50 g, 0.462 mol) in methanol (200 ml) acetic anhydride (75 g, 0.735 mol) was added slowly (1 hr). The temperature was kept at 10-15° C. during the addition. The reaction mixture was left overnight at room temperature. TLC [silica, chloroform/methanol/ammonia(33%) 90:10:1 (v/v)] showed one spot at Rf ~0.4. The product, N-Pyridin-4-ylmethyl-acetamide was not isolated and was processed to the next step.

Part of the reaction mixture (43 ml) was evaporated. The acetamide salt was obtained as yellow oil (14.5 g). Part of the oil (1.9 g, ≦0.06 mol) was dissolved in methanol (40 ml), stirred under nitrogen atmosphere and protecred from light. Iodomethane-d$_3$ (10 g, 0.07 mol) was added, maintaining the temperature of the reaction mixture at 15-25° C. The reaction mixture was left overnight at room temperature then triturated twice with ether (2×200 ml). 4-(Acetamido-methyl)-1-methyl-d$_3$-pyridiniumm iodide was obtained as yellow solid TLC [silica, chloroform/methanol/ammonia(33%) 90:10:1 (v/v)] showed one spot at Rf ~0.05] and was reduced in the next step without further purification.

To a cold (ice-water bath) solution of the pyridinum iodode salt in methanol (40 ml) under nitrogem atmosphere, sodium borohydride (3.9 gr, 0.2 mol) was gradually added (2 hr) so the temperature was maintained at 15-30° C., the reaction mixture was stirred for additional 2 hrs at room temperature and left overnight without stirring. The solvent was evaporated. N-(1-methyl-d$_3$-1,2,3,6,-tetrahydropyridine-4ylmethyl)-acetamide was obtained as stick yellowish oil (8.5 g). $^1$H-NMR (CDCl$_3$) δ 1.98 (s, 3H, CH$_3$CN), 2.12 (m, 2H), 2.52 (t, 2H), 2.91 (m, 2H), 3.76 (d, CH$_2$NHCO), 5.52 (m, CH═C), 6.66 (br. s, NH) ppm. MS m/e 172(M$^+$).

In a three-necked round bottom flask (250 ml) equipped with an addition funnel and condenser with a calcium chloride tube on its top, a solution of the tetrahydropyridine acetatide (8.5 gr) in dry acetonitrile (70 ml) was added. To the stirred solution, phosphorous pentasulfide (6.7 gr, 0.03 mol) was added followed by triethylamine (12 gr, 0.12 mol) which was added from the additional funnel during 10-15 min. The obtained solution was heated under reflux for 5 hrs and then left at 15° C. for three days. The solution was evaporated, basified with 10% aqueous potassium carbonate, then extracted with chloroform. The organic phase was dried and evaporated. Crude black N-(1-methyl-d$_3$-1,2,3,6,-tetrahydropyridine-4-ylmethyl)-thioacetamide (6.62 gr, 0.036 mol) was obtained. $^1$H-NMR (CDCl$_3$) δ 2.21(m, 2H), 2.56(s, CH$_3$CS), 2.58(t, j=4.4Hz, 2H), 2.97(m, 2H), 4.23(d, j=4.4 Hz, CH$_2$NH), 5.65(m, CH═C), 7.41(br s, NH) ppm. MS m/e 187(M$^+$).

In a flask (150 ml), polyphosphoric acid (30 g) was added to the crude thioacetamide (6.5 gr). The reaction was stirred and heated to 170° C. for 3.5 h. The hot reaction mixture was slowly poured into a stirred 25% aqueous sodium carbonate (150 ml). 25% Aqueous sodium carbonate (50 ml) was added to the residue in the reaction flask and the two solutions were combined. The basicity was raised by addition of an 50% aqueous sodium hydroxide (6 ml) and the reaction mixture was extracted with chloroform. The organic phase was separated, dried and evaporated. The residue was dissolved in petroleum ether (100 ml) to give after 12 h at −20° C. a solution and a small amount of insoluble material. The petroleum ether solution was evaporated and the obtained oil (5 g) was distilled at reduced pressure (b.p. 50-53° C., 0.2 mmHg) to give AF402 (2.15 g, 0.012 mol). $^1$H-NMR (CDCl$_3$) δ 1.87(m, 2H), 1.94(m, 2H), 2.1(m, 2H), 2.2(t, j=1.7 Hz, 3H), 2.76(m, 2H), 3.92(m, 2H) ppm. MS m/e 187(M$^+$).

EXAMPLE 18

Synthesis of N-[(2,8-Dimethyl-1-oxa-8-aza-spiro[4.5]dec-3-ylidene)-methyl-amine]-N-oxide, AF600

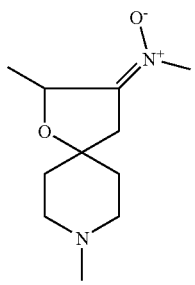

To a solution of N-methylhydroxylamine hydrochloride (0.85 gr, 0.01 mol) in ethanol (13.5 ml) was added sodium acetate (0.84 gr, 0.01 mol). A white precipitate was obtained. a solution of 2,8-dimethyl-1-oxa-8-aza-spiro[4.5]decan-3-one (1.62 gr, 0.0088 mol) in ethanol (7 ml) was added and the mixture was stirred at room temperature for 4.5 hrs. The solvent was evaporated, dichloromethane (675 ml) was added and the obtained solution was washed with 20% aqueous sodium carbonate. The organic phase was dried, the solvent was evaporated and flash chromatography (silica, CHCl$_3$/MeOH/NH$_4$OH 90/10/1) gave AF600 (1.5 gr) as a mixture of two isomers [less polar isomer(A)/more polar isomer(B) 1:4]. $^1$H-NMR (CDCl$_3$) δ 1.45 [d, j=6.37 Hz, CH$_3$ (A)], 1.54 [d, j=6.48 Hz, CH$_3$(B)], 1.7-1.9 (m), 2.29 [S, NCH$_3$ (A)], 2.31 [s, NCH$_3$(B)], 2.32-2.5 (m, 3H), 2.62 (s, CH$_2$), 3.63 [s, CH$_3$NO (A)], 3.68 [s, CH$_3$NO (B)], 4.78 [brCH (A)], 4.85 [brCH (B)] ppm. MS m/e 2.12 (M$^+$), 196, 169, 126, 110, 96, 70.

EXAMPLE 19

Synthesis of N-[C2,8-Dimethyl-1-oxa-8-aza-spiro[4.5]dec-3-ylidene)-benzyl-amine]-N-oxide, AF604

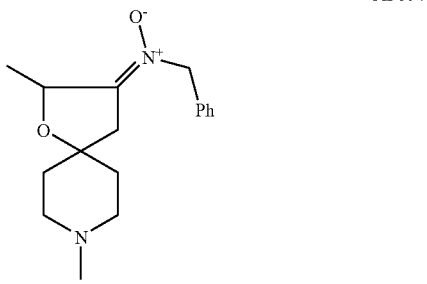

AF604

To a solution of N-benzylhydroxylamine hydrochloride (1.27 gr, 0.008 mol) in ethanol (6 ml) was added sodium acetate (0.65 gr, 0.008 mol). A white precipitate was obtained. A solution of 2,8-dimethyl-1-oxa-8-aza-spiro[4.5]decan-3-one (1.3 gr, 0.0072 mol) in ethanol (3.5 ml) was added and the mixture was stirred at room temperature for 4 hrs. The solvent was evaporated, dichloromethane (450 ml) was added and the obtained solution was washed with 20% aqueous sodium carbonate. The organic phase was dried, the solvent was evaporated and flash chromatography (silica, CHCl$_3$/MeOH/NH$_4$OH 90/10/1) gave AF604 (1.81 gr) as a mixture of two isomers [less polar isomer(A)/more polar isomer(B) 1:8]. $^1$H-NMR (CDCl$_3$) δ 1.42 [d, j=6.35 Hz, CH$_3$ (A)], 1.53 [d, j=6.45 Hz, CH$_3$ (B)], 1.7-1.9 (m), 2.29 (S, NCH$_3$), 2.32-2.55 (m), 2.62 (m, CH$_2$), 4.85(br CH), 4.91[s, CH$_3$NO (A)], 4.97 [s, CH$_3$NO (B)] pp MS m/e 288 (M$^+$), 272, 254, 197, 153, 91(100%).

EXAMPLE 20

Synthesis of N-[(2,8-Dimethyl-1-oxa-8-aza-spiro[4.5]dec-3-ylidene)-isopropyl-amine]-N-oxide, AF605

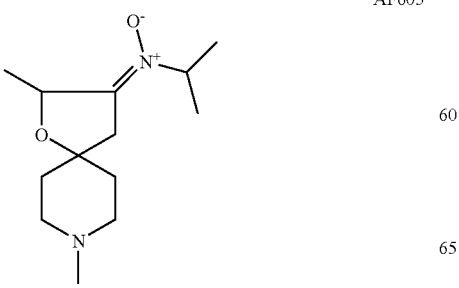

AF605

To a solution of n-isopropylhydroxylamine hydrochloride (1.84 gr, 0.01 mol) in ethanol (7 ml) was added sodium acetate (0.91 gr, 0.011 mol). A white precipitate was obtained. A solution of 2,8-dimethyl-1-oxa-8-aza-spiro[4.5]decan-3-one (1.84 gr, 0.01 mol) in ethanol (4 ml) was added and the mixture was stirred at room temperature for 4.5 hrs. The solvent was evaporated, dichloromethane (500 ml) was added and the obtained solution was washed with 20% aqueous sodium carbonate. The organic phase was dried, the solvent was evaporated and flash chromatography (silica, CH$_2$Cl$_2$MeOH/NH$_4$OH 90/10/1) gave AF605 (1.5 gr) as a mixture of two isomers [less polar isomer(A)/more polar isomer(B) 1:4]. $^1$H-NMR (CDCl$_3$) δ 1.40 (d, j=6.6 Hz, CH$_3$CH$_2$), 1.42 [d, j=6.2 Hz, CH$_3$(A)], 1.6-1.8 (m), 2.29 [s, CH$_3$(A)], 2.31 [s, CH$_3$(B)], 2.35-2.57 (m, 3H), 2.63-2.71 (m, 2H, CH$_2$), 4.05 [m, CHNO (A)], 4.18 [m, CHNO (B)], 4.83 (m, 1H, OCH) ppm.

EXAMPLE 21

Synthesis of N-[(2-Ethyl-8-methyl-1-oxa-8-aza-spiro[4.5]dec-3-ylidene)-methyl-amine]-N-oxide, AF601

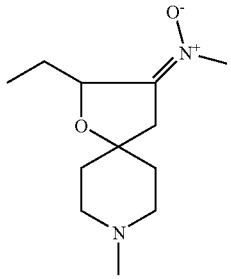

AF601

To a solution of N-methylhydroxylamine hydrochloride (0.95 gr, 0.011 mol) in ethanol (14.3 ml) was added sodiumacetate (0.94 gr, 0.011 mol). A white precipitate was obtained. a solution of 2-ethyl-8-methyl-1-oxa-8-aza-spiro[4.5]decan-3-one (2.1 gr, 0.01 mol) in ethanol (7.4 ml) was added and the mixture was stirred at room temperature for 5.5 hrs. The solvent was evaporated, dichloromethane (770 ml) was added and the obtained solution was washed with 20% aqueous sodium carbonate. The organic phase was dried, the solvent was evaporated and flash chromatography (silica, CHCl$_3$/MeOH/NH$_4$OH 90/10/1) gave AF601 (2.4 gr) as a mixture of two isomers [less polar isomer(A) and more polar isomer(B)]. $^1$H-NMR (CDCl$_3$) 0.94 [t, j=7.4 Hz, CH$_3$CH$_2$ (B)], 0.99 [t, j=7.4 Hz, CH$_3$CH$_2$ (A)], 1.59 (m, 1H), 1.74-1.86 (m), 1.98-2.05 (m, 2H), 2.29 [s, NCH$_3$ (A)], 2.30 [s, NCH$_3$ (B)], 2.45-2.60 (m, 5H), 3.63 [s, CH$_2$ (A)], 3.69 [s, CH$_2$ (B)], 4.66 [br OCH (A)], 4.78 [br OCH (B)] ppm. MS m/e 226 (M$^+$), 209, 197, 181, 169, 152, 138, 126, 110, 96, 70.

EXAMPLE 22

Synthesis of N-[(2-methyl-8-phenyl-1-oxa-8-azaspiro[4.5]dec-3-ylidene)-methyl-amine]-N-oxide, AF602

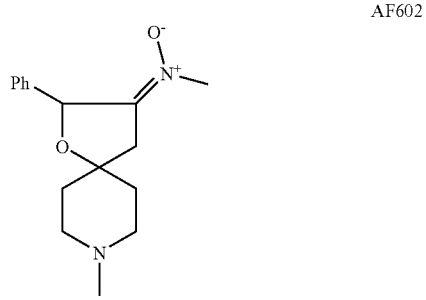

AF602

To a solution of N-methylhydroxylamine hydrochloride (0.33 gr, 0.004 mol) in ethanol (5.4 ml) was added sodiumacetate (0.32 gr, 0.004 mol). A white precipitate was obtained. a solution of 8-methyl-2-phenyl-1-thia-4,8-diaza-spiro[4.5]decan-3-one (0.85 gr, 0.004 mol) in ethanol (3 ml) was added and the mixture was stirred at room temperature for 4.5 hrs. The solvent was evaporated, dichloromethane (250 ml) was added and the obtained solution was washed with 20% aqueous sodium carbonate. The organic phase was dried, the solvent was evaporated and flash chromatography (silica, CHCl$_3$/MeOH/NH$_4$OH 90/10/1) gave AF602 (130 mg) as a mixture of two isomers [less polar isomer(A)/more polar isomer(B) 1:3]. $^1$H-NMR (CDCl$_3$) δ 1.24 (m, CH$_2$), 1.7-1.97 (m), 2.29 [s, NCH$_3$ (A)], 2.31 [s, NCH$_3$ (B)], 2.32-2.5 (m), 2.72 (m, CH$_2$), 3.30(m), 3.67 [s, CH$_3$NO (B)], 3.71 [s, CH$_3$NO (A)], 5.49 [br CH (A)], 4.74[br CH (B)], 7.28-7.56 (m, ArH) ppm. MS m/e 274 (M$^+$), 257(100%), 245, 168, 112, 96, 70.

EXAMPLE 23

Synthesis of Dihydro-5'-methylspiro[1-azabicyclo[2.2.2]octane-3,5'-(4'H)-3'-ylidene-methylamine-N-oxide, AF603

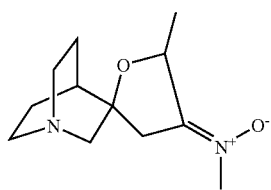

AF603

To a solution of N-methylhydroxylamine hydrochloride (1.17 gr, 0.014 mol) in ethanol (15 ml) was added sodium acetate (1.15 gr, 0.014 mol). A white precipitate was obtained. a solution of dihydro-5'-methylspiro[1-azabicyclo[2.2.2]octane-3,5'-(43'H)-3'-one (2.1 gr, 0.01 mol) in ethanol (7.4 ml) was added and the mixture was stirred at room temperature for 4.5 hrs. The solvent was evaporated, dichloromethane (770 ml) was added and the obtained solution was washed with 20% aqueous sodium carbonate. The organic phase was dried, the solvent was evaporated and flash chromatography (silica, CHCl$_3$/MeOH/NH$_4$OH 90/10/1) gave AF601 (0.45 gr) as a mixture of two isomers [less polar isomer(A) and more polar isomer(B)]. $^1$H-NMR (D$_2$O) δ 1.22 [t, j=7.09 Hz, CH (B)], 1.46 [t, j=7.0 Hz, CH (A)], 1.35 [d, j=6.5 Hz, (CH3)$_2$CH], 1.41-1.58 (m), 1.57-1.9 (m), 2.59 (m), 2.67-3.01 (m), 3.01-3.26 (m), 3.47 [s, N(O)CH$_3$ (A)], 3.49 (m), 3.52 [s, N(O)CH$_3$ (B)] ppm. MS m/e 224 (M$^+$), 207, 195, 178, 138, 124, 96, 83 (100%).

EXAMPLE 24

Synthesis of 2-Ethyl-8-methyl-1-thia-4,8-diaza-spiro[4.5]decane-3-thione, AF510

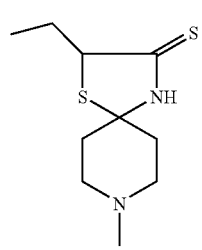

AF510

A mixture of AP267 (214 mg, 1 mmol) and Lawesson's Reagent (280 mg, 0.692 mmol) in acetonitrile (5 ml) was heated under reflux for 17 hrs. The solvent was removed and residue was dissolved in concentrate aqueous sodium carbonate (0.5 ml) and then extracted with ethyl acetate. The extract was dried and the solvent evaporated. The residue (250 mg), recrystallized fist from toluene and then from acetonitrile gave pure AF510. $^1$H-NMR (CDCl$_3$) δ 1.03 (t, CH$_3$CH2), 1.83 (m), 1.93-2.44 (m), 2.30 (s, CH$_3$N), 2.80 (m, 2H), 4.21 (dd, SCH), 8.66 (br, NH) ppm. MS m/e 230 (M$^+$), 197 (M$^+$-SH), 156, 128, 96 (100%).

EXAMPLE 25

Synthesis of 4-Benzyl-8-methyl-1-thia-4,8-diaza-spiro[4.5]decan-3-one, AF282

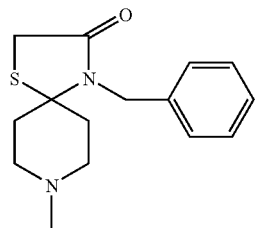

AF282

In a three-necked flask equipped with a magnetic stirrer and Dean-Stark and two dropping funnels a solution of mercaptoacetic acid (8 ml, 0.242 mol) in benzene (75 ml) was heated to reflux. Benzyl bromide (13 ml, 0.242 mol) and 1-methyl-4-piperidone (9.3 ml, 0.08 mol) were added simultaneously dropwise (45 min) and the reaction mixture was refluxed for additional 1.5 h (2 ml of water were collected). The reaction mixture was cooled to room temperature, water (30 ml) was added and the organic phase was separated, dried and the solvent was evaporated. Flash chromatography (silica, 10% methanol in chloroform) of the residue gave AF282 (3.8g). $^1$H-NMR (CDCl$_3$) δ1.65 (m, 2H), 2.19 (m, 4H), 2.27 (s, 3H, NCH$_3$), 2.78 (m, 2H), 3.64 (s, 2H, SCH$_2$), 4.78 (s, 2H, NCH$_2$), 7.25 (5), Ar) ppm.

EXAMPLE 26

Synthesis of 4-(2,4Dimethoxybenzyl)-8-methyl-1-thia-4,8diaza-spiro[4.5]decan-3-one. AF286

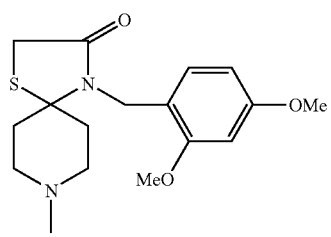

AF286

In a three-necked flask equipped with a magnetic stirrer and Dean-Stark a solution of 1-methyl-4-piperidone (0.27 ml, 2.4 mmol), 2,4-dimethoxybenzylamine hydrochloride (0.72 gr, 3.5 mmol)and, mercaptoacetic acid (0.24 ml, 3.5 mmol) in benzene (5 ml) was refluxed for 3 h. The reaction mixture was cooled to room temperature, water (10 ml) was added and the organic phase was separated. The pH of the aqueous phase was adjusted to pH 10 with 2.5N aqueous sodium hydroxide solution and then the aqueous phase was extracted with chloroform. The organic phases were combined, dried and the solvent was evaporated. Flash chromatography (silica, 10% methanol in chloroform) of the residue gave AF286 (140 mg, 15% yield). $^1$H-NMR (CDCl$_3$) δ 1.66 (m, 2H), 2.21 (m, 4H), 2.27 (s, 3H, NCH$_3$), 2.77 (m, 2H), 3.64 (s, 2H, SCH$_2$), 3.78 (s, 3H, OCH$_3$), 3.80 (s, 3H, OCH$_3$), 4.52 (s, 2H, NCH$_2$)

EXAMPLE 27

Synthesis of 4-(tert-Butyloxycarbonyl-8-methyl-1-thia-4,8-diaza-spiro[4.5]decan-3-one, AF284

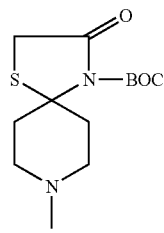

AF284

To a solution of AF277 (2.60 gr, 13.97 mmol) in dichloromethane (60 ml), triethylamine (1.95 ml, 13.99 mmol) di-tert-butyl dicarbonate (3.85 ml, 16.76 mmol) and 4-dimethylaminopyridine (1.71 gr, 13.99 mmol) were added. The obtained solution was stirred overnight at room temperature then the solvent was evaporated. Flash chromatography (silica, CHCl$_3$/MeOH/NH$_4$OH 80/20/1) of the residue gave AF284 (4 gr, >95% yield). $^1$H-NMR (CDCl$_3$) δ 1.55 (s, 9H, OC(CH$_3$)$_3$), 1.70-1.82 (m, 2H), 2.66 (m, 2H), 2.28 (s, 3H, NCH$_3$), 2.83-2.87 (m, 4H), 3.53 (s, 2H, SCH$_2$) ppm.

EXAMPLE 28

Formulation of AF150(S) in Paraffin Oil+Stability Studies

The stability of 10% w/w AF150(S) in pharmaceutical acceptable paraffin oil (Paraffin oil Eur. Ph) was examined at 40° C. under air or nitrogen atmosphere, in the presence or absence tocopherol. Samples were analyzed after two months storage. TLC, BPLC and GC were used to detect and determine the quantity of possible degradation product(s). Color changes were determined in comparison with Paraffin oil with or without tocopherol under the same conditions. AF150(S) was stable in the paraffin oil formulation. Degradation products, the thiolamide derivative (M$^{30}$ 202) obtained by hydrolysis of AF150(S), above 0.1% were not detected in any tested samples. A slight yellow color was observed in samples without tocopherol but color was not developed in samples containing 0.5% w/w tocopherol in AF150(S).

EXAMPLE 29

AF150(S) Citrate Salt+Stability Studies

To a solution of AF150(S) (30.13 gr, 163.8 mmol) in 2-propanol (60 ml) and tetrahydrofuran (100 ml) was added dropwise over 45 min a solution of anhydrous citric acid (29.51 gr, 153.5 mmol) in 2-propanol (200 ml). The resulted mixture was stirred at room temperature under argon atmosphere for additional 2 h, then the resulted white precipitate was filtered and washed with hexane under argon atmosphere. The white solid was introduced into a drying pistol which contained P$_2$O$_5$, the drying pistol was evacuated (0.2 mmHg) temperature and then heated at 55-60° C. for 6 h. AF150(S) citrate (53.8 g, 87.6% yield) was obtained. TLC (2% NH4OH in methanol) Rf 0.57; mp. 146.5-147.5° C.; $^1$H NMR (300 MHz, D$_2$O—Na$_2$CO$_3$, pH 12) δ 1.80(m, 4H), 2.08 (s, 3H, CH$_3$C=N), 2.17(s and m, 5H, CH$_2$+CH$_3$N$^+$), 2.46 (ABq, j=15.2 Hz, 4H, 2CH$_2$CO$_2$H), 2.73(m,2H), 3.81(s, 2H, CH$_2$N=C) ppm. $^{13}$C NMR (300 MHz, D$_2$O—Na$_2$CO$_3$, pH 12) 19.77, 36.17, 44.16, 45.64, 53.08, 72.71, 75.03, 170.91, 179.19 and 181.86 Hz.

HPLC analyses of samples of this salt stored under various conditions (at 60° C. for three months; in air at room temperature for three months) compared to a reference standard stored under anhydrous conditions showed the salt to be highly stable."

EXAMPLE 30

Brain Penetration of Compounds 1. pKa of AF267B: The freebase (non-ionized) form of the compound AF267B crosses the brain blood barrier. Since AF267B has a pKa of 7.8, at the pH=7.35 of the cerebrospinal fluid (CSF), 26.2% of the compound are in a free base form, calculated as shown below. This indicates that AF267B is highly penetrable into the brain since the free base is the specie that crosses the blood brain barrier. In comparison, some other known pharmaceutical CNS active compounds, for example wherein the base is quinuclidinyl, have a pKa≧9 (where the tertiary amine is highly basic). For such compounds at the relevant pH of 7.35, only 2.2% are in nonionized form. This indicates a higher preference for the brain for AF267B vs. such compounds. These calculations are based on the following:

BH$^+$→B+H$^+$

% B=100-% BH$^+$=100-100/[1+10$^{(pH-pKa)}$]

pKa (AF267B)=7.8 pH (CSF)=7.35

% B=100-100/1+10$^{-0.45}$]

% B=26.2%

For a base B' having a pKa=9.0

% B'100-100/1+10$^{-1.65}$]

% B'=2.2%

2) Rats were treated with AF267B (2 mg/kg, po) and plasma vs. brain levels of the drug were analyzed by GC. It was found that AF267B has a preference for the brain vs plasma:

a) by comparing the area under the curve extrapolated to infinite time (AUC) both in whole brain (ng/gr)*hr vs plasma (ng/ml)*hr both iv (1 mg/kg) and po (2 mg/kg), respectively, it was found that the ratio of AUC brain/AUC plasma is: for males 1.79 (iv) and 2.43 (po) and for females 1.32 (iv) and 1.25 (po). Thus greater amounts of the compound are found in the brain than in plasma;

b) by comparing the ratio of C$_{max}$ brain (ng/g)/C$_{max}$ plasma (ng/ml) (po) it was found that 25% of the compound in males and 16% in females is found in the brain. This calculation was based on the brain weight (2 gr) vs. total plasma volume (14 ml). This also indicates a high percentage of the compound in the brain.

3) ex vivo studies of AF150(S) and AF267B (100 µmole/kg, po) in mice brain tissue (GC analysis of AF150(S) or AF267B vs a standard compound (AF261) added to the brain tissue, or by displacement of a radioactive muscarinic compound such as tritiated-oxotremorine-M from the brain tissue) also show clearly a high brain penetration vs. plasma (GC and binding studies). AF150(S): $T_{max}$=1-10 min; $T_{1/2}$=21 and 53 min (two phases), iv; MRT (mean retention time)=50 min, iv, po. AF150(S) has a fast brain penetration (1 min iv); $C_{max}$=40.7 µmole/kg (40.7% in brain from the amount administered po); AF267B: detected in the brain between 2-240 min after dosing, a peak at 20-30 min, MRT=128 min. $C_{max}$=36.4 µmole/kg (36.4% in brain from the amount administered po).

EXAMPLE 31

Detection of AF292 Following AF267B Administration to Beagle Dogs.

The purpose of this study was to determine the levels of AF267B and AF292 (a metabolite of AF267B) in dog plasma following 13 weeks subchronic singly daily administration of AF267B (1.5, 3 and 6 mg/kg, po to male and female dogs) according to the method (see below).

Internal Standard (AF261): 2-Methyl-8-methyl-1-thia-4, 8-diaza-spiro[4.5]decan-3-one; MW 200. The analytical plasma samples originate from the in-life part of this study. Concentrations of AF267B and AF292 were determined by:
Column: Purospher STAR RP18e (4×50 mm, 3 µm)
Mobile Phases: Solvent A: 1 g/l $(HN_4)_2CO_3$ $(H_2O)$ Solvent B: Methanol
Loop/Injection Volume: 50 µl/10 µl
Ionisation Mode: Atmospheric Pressure Chemical Ionisation (APCI); positive ions
Sheath Gas Pressure: Nitrogen: 70 psi
Capillary Temperature: 250° C.
Spray Voltage: ~3.6 kV
Detection Mode: SRM (selected reaction monitoring)
AF292: m/z: 201.0 [CE (CE=collision energy 30V)]→m/z: 70.0 (0.0-5.2 min)]
AF261: m/z: 201.0 (CE 35V)→m/z: 70.0 (5.2-6.2 min); Internal standard
AF267B:m/z: 215.0 (CE30V)→m/z: 70.0 (6.2-10.0 min)
Collision Gas (CID): 2.5 mTorr/Argon Results:

After 13 weeks of repeated daily dosing AF267B has a plasma half life of 1-2 hrs with $T_{max}$=1.5-3 h, $C_{max}$ (ng/ml)= 162-1352 (linearly dose-dependent) and $AUC_{(0-t)}$ (ng*h/ml)= 712-3947 (linearly dose-dependent). AF292 has an approximately ten fold longer plasma life (~9-20 hrs) with $T_{max}$=3 hrs, $C_{max}$ (ng/ml)=136-555 and $AUC_{(0-t)}$ (ng*h/ml)=616-2451 (linearly dose-dependent). In comparison to AF267B, the pharmacokinetic profile of AF292 can be summarized as follows: AF292 has a $T_{1/2}$ in plasma about 3-5 times longer than AF267B (for example, AF292 $T_{1/2}$=10.6 hr for females, versus $T_{1/1\ =AF}$267B in females). The $C_{max}$ of AF292 is 50-90% vs. the Cmax of AF267B. AF292 shows an apparent shift to the right of $C_{max}$ vs the $C_{max}$ of AF267B (due to a delay in the appearance in plasma of AF292 vs. AF267B). On the basis of this observation, it will be appreciated that AF267B and AF292 may together form a pharmaceutical combination with a longer plasma $T_{1/2}$ than either compound alone. Such a combination may be adminstered as such.

EXAMPLE 32

Effects of the Tested Compounds on Secretion of α-$APP_s$ in Cell Cultures Stably Transfected With the M1 mAChR and in Rat Primary Hippocampal and Cortical Neuronal Cultures.

Cells were plated in 6 well culture plates and used at the age of 3-5 days after plating. Cells were washed twice in serum-free medium and incubated for 1 hour at 37° C. with AF150(S) and AF267B or AF292. The cell cultures were exposed for 1 hr to various concentrations of these tested compounds ($10^{-6}$-$10^{-3}$ M), and to carbachol ($10^{-4}$ M). Cells exposed to medium alone are referred as controls. Carbachol, rivastigmine and deprenyl were used as reference compounds.

Cell supernatants were collected into Eppendorff tubes containing a cocktail of protease intubitors (5 units/ml aprotinin, 5 mg/ml pepstatin A, 5 mg/ml leupeptin and $10^{-4}$ M Phenylmethylsulfonylfluoride (PMSF, a protease inhibitor); Sigma, USA). The collected media were concentrated with Centricon tubes (Amicon, Beverly, Mass., USA) and kept frozen for α-$APP_s$ secretion determination. Equal amounts of protein (50-100 µg) were loaded and separated on 10% sodium dodecyl sulfate-polyacrylamide gel electrophoresis (SDS-PAGE) Followed by western blotting onto nitrocellulose membrane, blocked by fat-free milk, and probed for 24 hours at 4° C., with anti-Alzheimer's precursor protein, A4 monoclonal antibody 22C11 (0.25 µg/ml; Boehringer Mannheim, Germany). The nitrocellulose membranes were washed and incubated for 2 hours at room temperature with peroxidase-linked goat anti-mouse IgG antibodies (Jackson Immunoresearch, USA), followed by extensive washout and staining with enhanced chemiluminescence detection system (Amersham). Quantitative evaluation of the immunoreactive bands, on the exposed films, was performed by video-imaging densitometry (Gel-aid software; Galai Co., Israel). $APP_s$ levels were expressed as x-fold increase over basal levels. In cell cultures stably transfected with M1 mAChR, α-$APP_s$-induced secretion was also calculated as % of maximal response to $10^{-4}$M carbachoL α-$APP_s$ secretion in cells expressing the M1 mAChR increased dosedependently following agonist stimulation. The maximal increase was obtained at $10^{-4}$ M AF267B (about 6-fold increase over control) and was equal to the maximal increase elicited by carbachol. Addition of the muscarinic antagonist, atropine at $10^{-5}$ M, inhibited completely the secretion of APP, induced by AF267B, indicating that the effect of AF267B is mediated via M1 mAChR. In several experiments, the activity of AF267B was compared to the activity of AF150(S). The results show that AF267B is more efficacious and potent than AF150(S) (50% of maximal response of carbachol for AF150(S) vs equal to maximal response of carbachol for AF267B). Additionally AF267B is more efficacious and more potent than its racemate (AF267) or AF102B (50% of maximal response of carbachol) on α-$APP_s$ secretion, while the less potent enantiomer AF267A is similar in potency to AF102B.

AF292 was as effective as AF267B (EC50=3 µM) and carbachol in activating elevation of $APP_s$, while rivastigmine and deprenyl were not effective in elevating $APP_s$ levels. Addition of atropine (10 µM) inhibited the secretion of $APP_s$ induced by carbachol, AF267B and AF292, indicating that the effect of these agonists is mediated via M1 mAChR Taken together, these results show that AF267B is a selective M1 muscarinic agonist and a "drug-prodrug" for AF292, which itself is a selective M1 muscarinic agonist and a weak M3 muscarinic antagonist AF267B and AF292 together form a pharmaceutical combination with a longer plasma half life and longer muscarinic activity than either compound alone.

Using the above tests, AF700 and AF704 were also found to be effective in increasing $APP_s$ levels in this preparation (at 100 μM 50% of maximal effect of carbachol).

The effect of various muscarinic agonists on the levels of secreted $APP_s$ were followed using rat primary cell cultures prepared from hippocampus, cerebral cortex (both which contain mainly M1 mAChR) and spinal cord (which contains M2 receptors). In this study the effects of carbachol (a non-selective muscarinic agonist) oxotremorine (>M2 selective muscarinic agonist), physostigmine (a cholinesterase inhibitor) and AF102B, AF150(S) and AF267B (M1 selective muscarinic agonists) on $APP_s$ secretion were tested.]

Primary cell cultures were prepared from embryos of Sprague-Dawley rats. The experiments were performed with cultures of hippocampus, cerebral cortex and spinal cord following the guidelines "Guide for Care and Use of Laboratory animals", National Research Council, Washington, D.C. 1996.

Brain tissues, hippocampus, cerebral cortex and spinal cord were removed from 13-14 or 18-19-day-old rat fetuses, respectively, by free-hand dissection and transferred into cold Gey's Balanced salt Solution (Gibco, BRL) containing 6 mg/ml glucose. After removal of meninges, the dissected tissue was mechanically dissociated using Pasteur pipettes followed by tripsyn-DNAase solution to obtain cell suspension. Dissociated cells were transferred to Dulbeco's Modified Eagle Medium (Biological Ind. Beit-Haemek, Israel) containing: 6 mg/ml glucose; 2 mM L-glutamate, 1000 IU/ml penicillin. The cell suspension was plated on poly-L-lysine (1 mg/ml)-pre-coated 12-well culture tissue plates at a density of $4 \times 10^5$ and $6 \times 10^5$ cells/well for hippocampal and cortical cells, respectively. Cell cultures were maintained for about 2 weeks in 37° C. incubator (95% air & 5% $CO_2$). Cells at 11-14 days in vitro were extensively washed and then subjected to various treatments as detailed below. Hippocampal and cortical cells were incubated with the tested ligands at a concentration of 100 μM for 1 h in magnesium-free Locke-HEPES buffer consisting of: 154 mM NaCl, 5.6 mM KCl, 3.6 mM $NaHCO_3$, 1.3 mM $CaCl_2$, 5.6 mM glucose and 10 mM HEPES, pH 7.4, containing 0.02% BSA. In the blockade studies the muscarinic agonists were co-incubated with the antagonist, pirenzepine (10 μM). Cells exposed to buffer alone were referred to as control. At the end of the incubation period, the conditioned media was removed and transferred to Eppendorff tubes, which contained a cocktail of protease inhibitors (as specified above). The supernatants were concentrated by centrifugation (2,500×g for 45 min at 4° C.) using Centricon-30 concentrators (Amicon, Inc. MA USA) and frozen at −70° C. till $APP_s$ levels were determined.

The content of protein in samples was determined in microplates according to Bio-Rad assay. Equal protein amounts of each sample (≈40 μg/lane) were loaded on 10% SDS-PAGE. When electrophoresis was completed, gels were blotted onto nitrocellulose membranes, blocked by fat-free milk and $APP_s$ bands were probed using the anti-Alzheimer precursor protein A4 (monoclonal 22C11, Boehringer Mannheim) and the secondary probe peroxidase-linked rabbit anti mouse IgG (Jackson ImmunoResearch, P). Following extensive washout the bands were stained with TMB (single solution, Zymed Lab., California) or developed with the Renaissance Chemiluminescence Reagent (DuPont, NEN) followed by exposure to an autoradiography film (Hyperfilm-ECL, Amersham).

Quantitative determination of the total $APP_s$ bands was performed by video-imaging densitometry (Gel-aid software, Galai Co. Israel). Data obtained for $APP_s$ were expressed as fold increase over control where the control was cells incubated with Locke buffer alone.

Primary rat cortical and hippocampal cultures cell cultures were exposed to the non-selective agonist carbachol (CCh) and oxotremorine (>M2 selective), to the M1 muscarinic agonists, AF150(S) and AF267B and to the cholinesterase inhibitor, physostigmine, all at 100 μM. The M1 agonists induced a significant increase in $APP_s$ secretion in both cell systems used, hippocampus and cortex as compared to levels determined in control cell cultures. In cortical cell cultures the increase in APPs levels ranged from 2.5 to 3.1-fold increase over control and an increase in the range of 1.8-2.8-fold over control was found in hippocampal cell cultures. AF150(S) and AF267B were more potent than CCh (2.8-fold and 1.5-fold over control, respectively). Oxotremorine and physostigmine were inactive. $APP_s$-induced secretion by AF150(S), AF267B and CCh was completely blocked by the M1 selective antagonist, pirenzepine (10 μM). These agonists did not activate $APP_s$ secretion in the spinal cord cultures, as these neurons do not contain M1 mAChR

EXAMPLE 33

Neurite-Outgrowth Response to Muscarinic Agonists in the Absence or Presence of Neurotrophins Rat pheochromocytoma cells transfected with M1 mAChR cells were grown as described in Gurwitz et al, (NeuroReport 6, 485, 1995). For determination of neurite outgrowth, cells plated in six-well plates were used 3-5 days after plating. Growth factors were added 1 day after plating and muscarinic agonists were added for the last 24 hrs.

Cells were observed under an inverted microscope. The percent of cells with neurite longer than cell diameter were scored in three random fields of several hundred cells from each well. Results were expressed as a percent of cells with neurites. Treatments were performed in triplicate cells. Both NGF (50 ng/ml) and EGF (100 ng/ml) were added 1 day after plating. Muscarinic agonists were added 24 hours before scoring.

The neurotrophic-like effects of AF102B, AF150(S) and AF267B vs carbachol (CCh) and their interaction with neurotrophins such as NGF, basic fibroblast growth factor (bFGF) and epidermal growth factor (EGF) were evaluated. Maximal response to CCh was 80% compared to 60% for AF267B and 30% for AF150(S). Pretreatment of rat pheochromocytoma cells transfected with M1 mAChR cells with NGF synergistically augments the neurotrophic response to all ligands tested and the efficacy of the agonists tested was increased.

There is an observable difference between the cellular response of rat pheochromocytoma cells transfected with M1 mAChR cells to NGF and bFGF on the one hand (induce differentiation) and to epidermal growth factor, EGF on the other hand (induces proliferation). The proliferating profile of EGF changed in the presence of muscarinic agonists as EGF together with muscarinic agonists induced an accelerated differentiation.

Taken together, the above results show that M1 selective agonists, alone or in combination with either endogenous or exogenously administered growth factors, may be used to induce neurotrophic effects beneficial in the treatment of neurodegenerative disorders, such as AD.

AF292, AF700 and AF704 were also found to be neurotrophic, and this effect was blocked totally by atropine, indicating the mucarinic nature of the effect

EXAMPLE 34

Effects on Aβ Levels in vitro

Primary mixed rat cortical neurons infected with recombinant Semliki Forest virus encoding either the human APP695 or APP C99 or C111 (Fassbeder et al, PNAS,98: 5856, 2001), were treated with one of the test compounds (AF102B, AF150 or AF267B, respectively for 5-8 hours. In these cell cultures APP is cleaved by γ- and β-secretase to produce Aβ, whereas α-secretase destroys Aβ. However, α-secretase is not present intracellularly. Cells were lysed and Aβ precipitated with W02 (anti Aβ antibody).

The mechanism of Aβ modulation was tested using C99 (and C111) that are truncated constructs generated from APP. Unlike APP, C99/C111 are direct substrates for γ-secretase. With both constructs it is possible to directly assay for γ-secretase activity, while with APP this is not possible. Both constructs are—as compared to APP—inefficient substrates for cc-secretase. Synergistc effects were also evaluated with CDX (methyl-β-cyclodextrin), an agent which extracts cholesterol from the plasma membrane. CDX inhibits also Aβ production CDX-treated cells were treated in addition to the respective muscarinic agonist for 5 min to reduce the cholesterol content.

Aβ levels were reduced upon treatment with the muscarinic agonists both in the cell lysate and medium in this system. AF267B was at least 5-fold more potent than AF150(S) in decreasing Aβ levels, being active in the μM range. A synergistic effect between AF267B and the general cholesterol lowering agent, CDX (5 mM), in their efficacy to decrease Aβ in this system to undetectable Aβ levels, was observed. It was also observed in these studies that the present M1 agonists, in addition to activating cc-secretase, inhibit γ-secretase. AF267B reduced the release of Aβ-like fragments (all fragments being in the 3-4 Kda) range by approximately 50%. This is equivalent to a γ secretase activity reduction of 50%. This was also evidenced by a complete loss of the p3 fragment (a fragment of APP resulting from γ-secretase cleavage) in the AF267B (1 mM)-treated cells vs the control. No other compounds have been reported with such a combined beneficial property on the various secretases (α-, β-, and γ-). The results indicate that the combination of an M1 agonist with a cholesterol lowering agent, such as a statin, enables the lowering of the dosage of the M1 agonist and thus reduction of possible side effects of the M1 agonist.

EXAMPLE 35

AF267B Decreases Elevated β-amyloids in Cortex in Hypercholesterolemic Rabbits

Dietary cholesterol induces Alzheimer-like Aβ-immunoreactivity in rabbit brain (Sparks et al. Exp Neurol 1994; 126: 88-94; Sparks Nutr Metab Cardiovasc Dis 1997; 7:255-266). New Zealand white male rabbits were allowed food and water ad libitur. Animals were fed either standard chow or chow supplemented with 2% cholesterol by weight (Purina) for 10 weeks. One group of animals were injected s.c. once a day with 0.9% sterile saline and the other group of cholesterol-fed animals were administered drug (AF267B; 1 mg/kg, s.c. body weight). Following 10 weeks of treatment animals were sacrificed and evaluated for Aβ immunohistochemistry, when all sections were stained simultaneously.

Limited neuronal Aβ was observed in cortex and hilus of chow fed rabbits. Among the cholesterol-fed animals injected with saline there are abundant neurons contained identifiable Aβ. Such neurons were observably smaller than those occasionally encountered in a control animal. The number of neurons expressing Aβ immunoreactivity was reduced 25-30% in the animals administered AF267B, and the intensity of the immunoreactivity was reduced approximately 50%. It was also noted that the neurons expressing Aβ after AF267B treatment were similar in size to those encountered in control brain and therefore larger than those found in cholesterol-fed saline injected rabbit brain.

These results show that AF267B is effective in decreasing elevated Aβ immunoreactivity in the brain following hypercholesterolemia, and has a neuroprotectve effect on the neurons that contain these Aβ peptides.

EXAMPLE 36

AF267B Decreases Elevated β-amyloids in Cortex in Hypocholinergic Rabbits (Lesioned Rabbits)

It is known that experimentally-induced cortical cholinergic denervation results in biochemical elevations of cortical Aβ concentrations and in histologic Aβ deposition (Beach et al, Neurosci Lett 283: 9-12, 2000), and that administration of muscarinic M1-selective agents to normal animals decreases CSF Aβ concentrations {Beach et al Brain Res.905: 220-223, 2001}. In the present example, animals with nbm lesions were treated with AF267B, an M1-selective agonist, to determine whether the lesion-induced increases in CSF and cortical Aβ could be prevented or reduced by chronic M1 receptor activation.

Twenty-eight female New Zealand White rabbits, about 2.5 kg each (young adults) were used. Twenty-one received lesions of the cholinergic nucleus basalis magnocellularis (nbm). The lesion was accomplished with unilateral i.c.v. injections of an immunotoxin consisting of the ribosomal toxin saporin conjugated to the monoclonal antibody MB20.4, which is directed against the low-affinity neurotophin receptor, p75. The ME20.4 antibody is made against monkey p 75 and also recognizes rabbit p75. The dose of immunotoxin was 32.4 μg in 12 μl; this was delivered to the right lateral ventricle 2 mm lateral to the bregma. Seven animals received i.c.v. injections of sterile normal saline (sham lesion). Animals which received the immunotoxin were divided into 3 groups of 7. One group received twice-daily s.c. injections of AF267B; each dose was 1 mg/kg for a total daily dose of 2 mg/kg. Another group received physostigmine hemisalicylate in normal saline by s.c. osmotic pump at a daily dose of 3 mg/kg. The third group received twice-daily sterile saline s.c. injections. The animals which received a sham lesion were implanted with s.c. osmotic pumps filled with sterile normal saline. Animals were euthanized 4 weeks after surgery. In the case of animals receiving AF267B injections, all animals received a final injection approximately 2-3 hours before sacrifice. Four animals died prematurely [(1 control animal and 3 physostigmine-treated animals), 1 to post-op hemorrhage, 1 was euthanized after developing uncontrollable seizures, 1 was euthanized due to hindlimb paralysis induced by i.m. injection of anesthetic agents prior to surgery and 1 was found dead with no cause of death found at autopsy)] and were excluded from analysis. Cerebrospinal fluid was taken from the cisterna magna of all animals at the time of sacrifice; the brain was removed and sliced coronally into 0.5 cm slices. One slice, at the level of the hypothalamus (this slice has hippocampus, as well as cortex), was fixed in 4% parafirmaldehyde and processed for immunohistochemical staining with an antibody to Aβ. The other slices were frozen on sheets of dry ice (the other slices are the non-fixed 0.5 cm coronal slices of cerebrum, brainstem and cerebellum). Western blot analysis for Aβ and sAPPα was performed on the CSF from 2 of the 4 groups, those with nbm lesion and normal saline treatment and those with nbm lesion and AF267B.

Quantification of the 4 kDa band representing CSF Aβ showed a noticeable decrease in CSF Aβ in the AF267B-treated animals versus the control animals (p=0.05, unpaired, two-tailed t-test). There was no significant difference in the intensity of the bands representing sAPPα. Sections from the same 2 groups of animals stained immunohistochemically for Aβ revealed vascular Aβ deposition as well as perivascular diffuse deposits in all animals. The lesion-and-treatment study showed that both AF267B and physostigmine reduced histologic deposition and biochemical levels of Aβ. Histologic Aβ deposition was reduced to 6.4% and 12% of the lesioned, untreated group for physostignine and AF267B, respectively. Analysis of variance found that the two treatment groups differed significantly (p=0.01) with respect to Aβ deposition (Aβ deposition was high in the untreated lesioned animals vs low in the animals which were lesioned and treated with AB267B) and that both AF267B and physostigmine-treated groups differed significantly from the lesioned, untreated group (p<0.05, Fisher's LSD) with respect to Aβ deposition (Aβ deposition was high in the untreated lesioned animals vs low in the lesioned animals treated with AB267B or physostigmine).

The results show that AF267B treatment of animals with nbm lesions reduces the increases in CSF Aβ and brain Aβ deposition that are induced by the lesion, and indicates thatM1 muscarinic agonists such as AF267B may used as preventative therapy for AD.

EXAMPLE 37

Prevention of Cytotoxicity and Programmed Cell Death (Apoptosis) Induced by Various Insults (Deprivation from Growth Factors or Growth Factor Found in Serum. β-amyloids, Oxidative Stress)

Confluent rat pheochromocytoma cells transfected with the M1 mAChR cultures were detached with trypsin, washed and plated in 24well, 6-well, 60-mm or 100-mm plates that were precoated with rat tail collagen (Sigma, Israel). Several experiments were performed in serum-free medium. For 3-(4, 5-dimethylthiazol-2-yl)-2,5-diphenyl-tetrazolium bromide (MIT) assay, cells ($1.5 \times 10^4$) were plated in 96-well collagen-precoated plates, in serum-free medium, with or without various drugs for 24 hours. For differentiation, cells were grown in the presence of 1% FCS and 1% HS, with addition of 50 ng/ml NGF for 7 days, to cause full differentiation. Cells were grown either on 100-mm plates ($5 \times 10^5$ cells per plate; MTT, Fluorescence activated cell sorter (FACS) activities), or on Chamber-Slides ($1.5 \times 10^4$ cells; TUNEL) that were precoated with collagen, or on 13-mm glass coverslip pretreated with Poly-L-Lysine, in 24-well plates (7500 cells per well; DAPI). After 7 days, cells were washed and the medium was either replaced to serum-free, or cells were detached and replated in serum-free medium. Cells in serum-free medium were treated either with Aβ peptides that were previously "aged" or with $H_2O_2$. Tested compounds were added together with the insults for the indicated time, unless otherwise stated.

Cell Viability Assay:

Cells were plated in 96-well plates in 100 μl medium. After exposure to various treatments, 10 μl of 5 mg/ml MTT [3-4, 5-dimethylthiazol-2-yl)-2,5-diphenyl-tetrazolium bromide; Sigma, Israel] solution in phosphate-buffered saline (PBS) was added to each well. Plates were incubated for 2 hrs at 37° C. followed by hydrocholoric acid-isopropanol addition (100 μl of 0.04N HCl/isopropanol). Plates were read using ELISA reader at a wavelength of 570 nm.

Nuclear Staining of DNA:

Cells were grown and treated on glass coverslips. After treatments, cells were fixed in cold methanol for 5 min at −20° C. followed by treatment with cold acetone at 4° C. for 2 min and washing in PBS. The coverslips were fluorescently stained with DAPI (4,6-diamidino-2-phenylindole; 5 mg/ml, Sigma, Israel) an intercalating agent that enables visualization of chromatin condensation in the cell nuclei for 15 min at room temperature. Cells were washed three times with PBS, mounted in a solution of glycerol containing 22 mM 1,4 dizabicyclo(2,2,2)octane (Sigma, Israel) to prevent fading, and viewed for nuclear chromatin morphology with a fluorescence microscope. Apoptotic and viable cells were counted (200 cells per coverslip, each experiment was performed in duplicates).

TUNEL Assay:

This method reveals DNA fragmentation in individual apoptotic cells. The TUNEL (Terminal deoxynucleotidyl transferase (TdT) mediated dUTP nick end labeling) method enzymatically labels DNA fragments at the 3'OH ends (representing the DNA strand breaks) with fluorescein-dUPT (Boehringer Mannheim, Germany). Briefly, following treatment, cells grown on Chamber slides were fixed with paraformaldehyde solution (4%) in PBS, pH 7.4 for 30 min at room temperature. Following washing with PBS cells were permeabilized using 0.1% Triton X-100, 0.1% sodium citrate solution, for 2 min on ice (4° C.), washed with PBS and 50 μl of TUNEL reaction mixture was added on each sample for 1 hr at 37° C., in a humidified chamber. Evans Blue reagent (diluted 1:2000 in PBS) was added for 5 min and the slides were viewed with fluorescence microscope.

Fluorescence Activated Cell Sorter (FACS) Analysis:

Cells were differentiated for 7 days and detached from the plates with Trypsin. $10^6$ cells were replated in 50-mm collagen-coated plates in serum-free medium in presence or absence of various treatments. 200-g-centrifuged pellets were prepared and resuspended in 300 μl PBS. 4 ml of cold methanol (−20° C.) were added to each test tube and the fixation was carried out for 15 min at −20° C. Cells were washed in PBS, spun and resuspended in 1 ml PBS. Five microliters of Propidium iodide stock solution (Sigma; 10 mg/ml) and 5 μl of 20 mg/ml solution of RNAse A were added for 5-10 min at room temperature. Fluorescence of individual nuclei was measured using Fluorescence Activated Cell Sorter (FACScan; Becton Dickinson Corp.) excited at 488 nm wavelength and collected through 575±21 nm BP filter. The data were analyzed by Cell Quest software computer system. By this method we were able to measure DNA content of the cells (apoptotic cells have less DNA). Cells in G1 phase of cell cycle are after mitosis and have less DNA than cells in G2/M phase (before and during mitosis). Apoptotic cells were identified as the pre-G1 phase.

The MTT assay measures primary early changes within the cells, reflecting the integrity of the electron transport chain and provides a readout of cellular redox activity. This test is a specific, early indicator of the mechanism of β-amyloid-mediated cell death and can be used to detect rapid inhibitory response. Starved, undifferentiated, rat pheochromocytoma cells transfected with M1 mAChR cells alone reduced cell viability by 10-20% and this effect was further augmented (up to 50-60% inhibition) by increasing concentrations of the neurotoxic full-length β-amyloid (β-$A_{1-42}$) peptide and its fragment, (β-$A_{25-35}$) (0.5-20 μM). When such cells were serum-deprived and treated with β-amyloids, in the absence or presence of muscarinic agonists, the cell death induced by β-$A_{25-35}$ (1 μM) after 24 hrs was significantly attenuated by addition of carbachol or AF292, AF150(S) and AF267B.

The potential of carbachol, AF150(S), AF267B and AF292 in protecting cells transfected with M1 mAChR cells from a direct oxidative stress induced by $H_2O_2$ was tested. These agonists were observed to protect the cells from $H_2O_2$-induced toxicity.

Surprisingly, muscarinic agonists were detected in compounds that have a muscarinic pharmacophore to which an antioxidant moiety is attached. These include AF604, AF700 and AF704, the structures of which include a selective M1 agonist moiety linked to an antioxidant moiety. Notably, AF700, AF703 and in particular AF704 and AF704B are more effective than carbachol and AF267B against β-$A_{25-35}$ (10 & 20 μM-induced cytotoxicity.

Using DAPI an intercalating agent which enables visualization of chromatin condensation in the cell nuclei apoptotic cell death after Aβ or $H_2O_2$ treatment was followed. Aβ-treated cells showed the morphology of apoptotic cells that shrank and lost their processes. DAPI staining revealed nuclear condensation and fragmented chromatin that is indicative of apoptotic processes. AF150(S) and AF267B were found to protect these cells from apoptosis and the neuritic-like processes are well observed.

A two-fold increase in apaptotic cell death was observed after starvation for 24 hrs of the cells transfected with the M1 receptor (but not in the untransfected cells). AF150(S) and AF267B significantly protect the apoptotic cell death induced by starvation. Atropine (a non-selective muscarinic antagonist) and pirenzepine (an M1 selective antagonist), reversed the protecting effect of the muscarinic agonists only in the M1 transfected cells.

Treatment of cells transfected with M1 mAChr with β-$A_{25-35}$ (25 μM) or β-$A_{1-42}$ (25 μM) further increased by 1.5-2 fold the apoptotic cell death over starvation. The selective toxic effect of both peptides was shown using the reversed peptide (β-A35-25) that did not induce apoptosis. Aβ-induced apoptosis was prevented by AF150(S) and AF267B only in the M1 tansfected cells, while muscarinic antagonists reversed these effects.

Oxidative insult induced by $H_2O_2$ (25 and 50 μM) increased the apoptotic population by 1.5 and 2.5 fold over starvation, respectively. AF150(S) and AF267B prevented $H_2O_2$-induced apoptosis and their effect was selective to M1 mAChR activation, as atropine reversed the effect.

The TUNEL method also reveals DNA fragmentation that occurs following apoptosis in individual apoptotic cells. The number of TUNEL-positive stained cells increased after 25 μM β-amyloid 25-35 treatment indicating on apoptotic process, while AF150(S) (100 μM) was able to block the apoptosis so that most of the cells were TUNEL-negative stained. The cells retained their processes, and only the cytoplasm was stained in red.

Quantification of apoptotic population was performed by measurement of cell DNA content, after various treatments using FACS analysis. DNA histograms obtained from serum-deprived neuronal cultures in the M1 transfected cells revealed the appearance of apoptotic cell population with degraded (subdiploid) DNA content (M1=pre-G1 phase). About 20% of total cells underwent apoptotic death after starvation for 24 hrs. Carbachol, AF150(S) and AF267B, protected cells from apoptotic death during starvation. β-Amyloid25-35 or β-amyloid 1-42 increased the apoptotic population to 30-35% of the cells. Co-addition of carbachol, AF150(S) or AF267B reduced the apoptotic population significantly, even below the values observed after starvation. The effect of the muscarinic agonists was blocked by 10 μM atropine indicating the involvement of M1 mAChR activation in the survival effects. Moreover, in non-transfected cells, the agonists were ineffective on starvation- and β-amyloid-induced apoptosis.

EXAMPLE 38

Protection Against Cell Death Induced by N-methyl-D-Aspartate (NMDA)

Primary rat brain cell cultures derived from 18-19 day old embryonic (Sprague Dawly rats) rat brains were prepared by mechano-dissociation. The brains were removed into cold Gey's Balanced salt Solution (GBSS, Gibco, BRL) containing 6 mg/ml glucose. The hippocamous and cortex were separated and transferred to Dulbecco's Modified Eagle Medium (DMEM, Biological Industries, Bet-Haemek, Israel) containing 6 mg/ml glucose, 2 mM L-glutamine (Biological Industries, Bet-Haemek, Israel), 1000 I.U/ml Penicillin G sodium and 3% ultrosere G (Gibco, BRL). Following cell dissociation using a fire polished Pasteur pipette, the resulting cell suspension was plated on tissue cultures pre-coated with poly-L-lysine (30,000-70,000 MW, Sigma) 1 mg/ml in borate buffer. Cells were plated at a density of 80000 cells/well on a 96 well culture plate, or at 400000 cells/well (hippocampal cells) and 600000 cell/well (cortcal cells) on 12 weft culture plates. Cell cultures were maintained in growth cell medium at 37° C. 5% $CO_2$/95% $O_2$ for about 2 weeks. Glial cell proliferation was arrested following 3-4 days in culture by addition of 5-fluoro-2'-deoxyuridine/uridine/cytosine arabinoside mixture (5 mM final concentration).

For evaluating exposure to NMDA, cortical and hippocampal cell culture at 10 days in culture plated in 96 well culture plates were exposed to 100 or 200 μM NMDA (RBI, USA). Neuroprotective potency of compounds from formula I was compared to that elicited by 20 μM of MK801 (a non-competitive NMDA receptor antagonist). Cell cultures were also exposed in parallel to medium alone and were referred as to controls. In order to produce widespread neuronal injury, all exposures were carried out for 20-24 hrs prior assessing neuronal cell death. Neurotoxicity was quantitatively assessed by measuring the extent of mitochondrial activity in living cells using {2,3-bis[2-methoxy-4-nitro-5-sulphopheny]-2H-tetrazolium-carboxanilide inner salt]}-based assay (Klausner, Biotechnol 5:779-786, 1987; Lipman et al, Cytotechnol 8:129-176, 1992).

AF150(S) and AF267B were effective in prevention of cell death. The neuroprotective potency of 100 μM of these agonists against 100 μM NMDA-induced toxicity was similar to that elicited by 20 μM MK801, but slightly less against 200 μM of NMDA.

EXAMPLE 39

1. Effects on Tau Protein Hyperphosphorylation:

Primary cell cultures were grown as described in EXAMPLE 38. Cell supernatants were removed and the cells were washed once in medium prior to the addition of cold phosphate buffre saline ph=7.4 (PBS) solution containing 0.2 mM EDTA. Cells were scraped using a rubber policeman, transferred to Eppendorf tubes, and centrifuged at 4° C. Cell pellets were resuspended in lysis buffer (EDTA 5 mM, Tris 50 mM, Triton 1%, NaCl 150 mM) containing protease inhibitors (5 units/ml apronitin, 5 mg/ml pepstatin, 5 mg/ml leupeptin and 0.1 mM PMSF, Sigma) and subjected to centrifugation at 4° C. Supernatants were transferred into Eppendorf tubes and kept at −20° C. till analyzed. The extent of tau-1 immunoreactivity (an antibody that recognizes a non-phosphorylated tau at $Ser^{199}$) was determined by western blots.

AF150(S) and AF267B were effective in elevating tau immunoreactivity both in cortical and hippocampal cell cultures in a dose range of 1-100 μM.

2. Effects on Tau Phosphorylation and Antagonism of Aβ-Induced Effects on Tau Phosphorylation Following the experimental design of Sadot et al., J.Neurochem. 66:877-880, 1996, including immunobloting with AT8 antibody, an antibody that recognizes phosphorylated tau at $Ser^{199/202}$, it was found that AF26713, AF292 AP704, and AF704B (100 μM) induce dephosphorylation of tau proteins in these cell cultures to the control level. By linking an M1 agonist to an antioxidant moiety tau phophorylation may be decreased, providing a new therapeutic strategy in a variety of CNS disease states due to combined damage due to oxidative stress and tau hyperphosphorylation.

EXAMPLE 40

Effects on ApoE Synthesis and Secretion in Rat Primary Type 1 Astrocyte Cultures Primary cultures of type 1 astrocytes were derived from the cortex of Sprague Dawley rats. The compounds tested were dissolved in the culture media and added to cells for 24, 48, 72 and 96 hrs. Media was then removed and kept frozen until ApoE protein levels were evaluated by immunoblot analysis as described in Poirier et al Neuroscience 55: 81-90 (1993). Alternatively the methods of Cedazo-Minuez et al [Neurosci 105: 651-661, 2001} may be employed. AF102B at 96 hrs was inactive toward ApoE metabolism (synthesis and secretion). The compound AF267B, and to a lesser extent AF150(S), inhibits the production of ApoE over time with a maximal effect at 96 hrs. The effects observed (60-80% fihibition) occur at 0.1 nM, a very low concentration of the compound. These results indicate that this compound inhibits apoE production, including ApoE4 in rat astrocytes, and thus may be used in therapies in which inhibition of ApoE production is indicated.

EXAMPLE 41

Competition Binding Assay for Muscarinic Receptor With an Agonist as the Labeled Probe.

Oxotremorine-M (OXO-M) is an agonist that binds to all muscarinic receptor subtypes with similar affinities. The ability of a test compound to displace [$^3$H]OXO-M binding provides a measure for the affinity of the test compound to the receptor agonist binding site. The competition of [$^3$]OXO-M binding with AF292 and its enantiomer, AF291, have $K_i$ values of 0.27 and 6.56 μM respectively as compared to the full agonist carbachol which shows a $K_i$ of 0.05 μM.

Pirenzepine (PZ), a muscarinic antagonist, binds preferentially to M1 receptors while OXO-M binds to all mAChR subtypes non-selectively; the ratio between the $K_i$ values for PZ versus that of OXO-M may be indicative of the selectivity of the tested compound. The smaller the ratio, the more M1 selective is the tested compound. Competition of [$^3$H]PZ binding to rat cortical membranes with AF292 ($K_i$=1.39 μM) and its enantiomer AF291 ($K_i$=10.7 μM) shows that AF292 is the active enantiomer. The OXO-M/PZ ratio is ~0.36 showing a moderately high selectivity for the M1 receptor.

EXAMPLE 42

Muscarinic Receptor Selectivity

1. Functional Studies in Cell Cultures Transfected With Human Muscarinic Receptor Subtypes 1.1 AF292 was tested for its agonistic or antagonistic properties, its potency, and its selectivity towards the human M1 vs. M3 and M5 receptors in activating phosphoinositide (PI) hydrolysis according to the method of Gurwitz et al Eur. J. Pharmacol. 267, 21, 1993. The effects of the compounds were atropine-sensitive in activating PI hydrolysis demonstrating, their muscarinic nature. AF292 and AF267B were found to be partial agonists at the M1 receptor, showing ~35% and ~66% activity, respectively, versus carbachol with respect to PI turnover measured in this paradigm. No activity was seen at the M3 and M5 receptor with AF292, as compared with AF267B (~30% vs. carbachol at the M3). AF292 was both a partial agonist at the M1 receptor and a weak antagonist at the M3 receptor ($pK_b$=0.66 μM), with no agonistic activity at M2 or M5 mAChR. The effects on the M2 receptor were measured in modified cell cultures that show an increase in intracellular Ca ions following activation with carbachol. In spite of an 8-fold increase in activity induced by carbachol on the M2 mAChR, AF292 was inactive as an agonist at all tested concentrations ($10^{-9}$-$10^{-3}$M).

1.2. AF292 was tested for its agonistic or antagonistic properties, its potency, and its selectivity towards the human M1 vs. M3 and M5 receptors in activating arachidonic acid (AA) hydrolysis according to the method of Gurwitz et al Eur. J. Pharmacol. 267, 21, 1993. AF292 was more potent on AA release induced by M1 mAChR (80%) than on PI turnover (35%), but still inactive as an agonist (AA release) on M3 and M5 mAChR. Thus AF292 is a more efficacious agonist on M1 mAChR-mediated AA release (mediated via phospholipase A2) than on PI (mediated via phospholipase C). In summary, not only is AF292 highly selective for the M1 mAChR as an agonist, but it also exhibits distinct activation of select G-proteins (e.g. not all the G-proteins are activated to the same extent by AF292, unlike carbachol, which acts as a non-selective mAChR agonist that activates all these receptors to the same extent 2. Binding Studies to Muscarinic Receptors and Other Systems 2.1 In competitive binding studies against the following ligands for mAChR receptors, AF267B was found to be highly selective for the following M1 mAChR subtypes: QNB [Muscarinic Antagonist in Rat Cortical (CTX) Membranes] ($K_i$=49.6±9 μM); QNB [Muscarinic Antagonist in Rat Cerebellar Membranes] ($K_i$=45.2±10.8 μM); Pirenzepine ($M_1$ selective Antagonist in CTX) ($K_i$=3.74± 0.59 μM); Oxotremorine-M (Muscarinic Agonist in CTX) ($K_i$=1.62±0.34 μM)]; vs. Serotonin, $5HT_3$ 51.3% inhibition at $10^{-4}$ M; Opiods/Opiate, Non-Selective 52.5% inhibition at $10^{-4}$ M; with no binding at all to Adrenergic(A), α1A, Adrenergic; α1B, Adrenergic; α2A (Human Recombinant); Adrenergic, α2B; Adrenergic, α2C (Human Recombinant); Adrenergic, β1; Adrenergic, β2; Benzodiazepine (BZD), Peripheral; Clozapine; Dopamine, D1; Dopamine, D2 (Human Recombinant); Dopamine, D3 (Rat Recombinant); GABA A, Agonist Site; GABA A, Benzodiazepine, Central; Glutamate, AMPA Site; Glutamate, Kainate Site; Glutamate, NMDA Agonist Site; Glutamate, NMDA, Glycine; Glycine, Strychnine-Sensitive; Histamine, H1; Histamine, H2; Histamine, H3; Nicotinic; Ganglionic site; Nicotinic, Neuronal site; Serotonin, 5HT1A (Human Recombinant); Serotonin, $5HT_{1B}$; Serotonin, $5HT_4$; Serotonin, $5HT_6$ (Rat Recombinant); Serotonin, $5HT_7$ (Rat Recombinant); Choline Acetyltransferase; Glutamic Acid Decarboxylase; Monoamine Oxides A, MAO-A; Monamine Oxidase B, MAO-B.

2.2. In binding studies, AF292 (10 μM) was found to be highly selective for the mAChR subtypes {M1 (human) (55%), M2 (human) (61%), M3 (human) (55%)} with no binding at all to: adenosine A1 (human); A2A (human); adenosine A3 (human); alpha 1 adrenergic (non-selective); alpha 2 (non-selective); beta 1 (human); angiotensin, AT1 (human recombinant); benzodiazepine (BZD) (central); bradykinin, B2 (human recombinant); cholecystokinin (CCKA) (human recombinant) (CCK1); dopamine D1 (human recombinant); D2S (human recombinant); endothelin, ETA (human recombinant); GABA (non-selective); galanin, GAL2 (human); chemokine, IL-8B (human recombinant) (CXCR2); chemokine, CCR1 (human recombinant); histamine, H1 (central); histamine, H2: melanocortine, MC4 (human recombinant); melatonin, ML1; tachykinin, NK2 (human recombinant); NK3 (human recombinant); neuropeptide, Y1 (human); neuropeptide, Y2 (human); neurotensin, NT1 (human recombinant) (NTS1); opiate, delta 2 (human recombinant) (DOP): opiate, kappa (KOP); opiate mu (human recombinant) (MOP); orphanin, ORL1 (human recombinant) (NOP); serotonin, $5-HT_{1A}$ (human recombinant); serotonin, $5-HT_{1B}$; serotonin, $5-HT_{2A}$ (human recombinant); serotonin, $5-HT_3$ (human recombinant); serotonin, $5-HT_{5A}$ (human recombinant) (5-ht5A); $5-HT_6$ (human recombinant); $5-HT_7$ (human); somatostatin, sst (non-selective); vasoactive intestinal peptide, VIP1 (human) (VPAC1); vasopressin V1a (human recombinant); $Ca^{2+}$ channel (L, verapamil site); K+V channel; SK+Ca channel; $Na^+$ channel (site 2); $Cl^-$ channel; norepinephrine NE transporter (human).

EXAMPLE 43

Effects in Aging Microcebes

Aging microcebes show similar cognitive deficits and cerebral lesions to those observed in aging humans and in AD patients. Thus this is a good animal model for AD, mimicing the three major hallmarks in AD {plaques (Aβ), paired helical filaments (hyperphophorylated and aggregated τ) and cognitive dysfunction}. This model may also be used to mimic MCI conducive to AD In this model AF150(S) [chronic treatment for 18 months]: i) improved the cognitive and behavioral impairments ii) decreased hyperphosphorylated τ proteins and the number of neurons containing aggregated τ protein (e.g. indicative of diseased brains) and the number of paired helical filaments; and iii) decreased astrogliosis and inflammation. This indicates AF150(S) may be used as a drug to treat or modify the effects of AD but does not produce tolerance following prolonged treatment.

EXAMPLE 44

M1 Agonists Reduce Neurobehavioral Impairments Following Closed Head Injury in Mice Closed head injury (CHI) was induced in mice as described in Chen et al, J Neurotrauma, 15: 231-237. 1998. Neurological severity scores (NSS) were assessed using a battery of 10 parameters (10=worst outcome, 0=normal function). The compounds tested (1 mg compound/kg body weight) vs. placebo-treated animals were injected ip 5 min after CHI vs. placebo-treated animals. Treated mice were evaluated at 1 h, to determine the severity of injury, and at 24 and 48 h to determine recovery. The NSS was as follows: 1. Control (N=10): 7.80±4.25 (1 h); 5.30±0.33 (24 h); 4.20±0.47 (48 h). 2. AF150(S) (N=10): 8.00±0.21 (1 h); 4.30±0.26 (24 h); 2.90±0.23$^b$ (48 h); AF267B (N=9): 7.89±0.26 (1 h); 3.67±0.24* (24 h); 2.89±0.26° (48 h) [*p=0.03; **p=0.03; $^a$p=0.009; $^b$p=0.005; $^c$p=0.004].

All the compounds tested showed a highly significant improvement on the motor functions. Recovery was faster in the AF267B treated animals in two balance tests (beam walk)—[22% vs 80% in control at 24 h (3 cm) or 33% vs. 80% in control at 48 h (2 cm)].

EXAMPLE 45

AF150(S), AF267B in Social Memory in Rats

Social olfactory recognition in rodents has been shown to assess short term memory and to be sensitive to cholinergic drugs (Dantzer et al. Psychopharmacol. 91:363-368, 1987; Perio et al Psychopharmacol. 97: 262-268. 1989). In this example the effect of AF150(S) and AP267B on investigatory behavior of naive rats was tested.

12 Male Wistar rats, 400-530 gr (4-5 months old) were used Rats were housed individually 14 days before testing. Juvenile Wistar rats 40-50 gr (at arrival) were kept in groups of 6 and served as social stimuli for the adult rats. Animals were kept at 21° C.±1, with an inverse light-dark cycle (light on from 2:00 P.M. to 2:00 A.M.). The sessions were conducted 7 hr into the dark part of the light/dark cycle, under red illumination.

Adult rats were placed in a dim illumination room 1.5 h before the beginning of the social test. All juveniles were isolated in cages for 30 min prior to the beginning of the experiment. At the beginning of testing, an unfamiliar juvenile rat was placed in the home cage of an adult rat for 5 min. The time spent by the adult rat in investigating the juvenile rat was recorded. The adult rat was then immediately (1-2 min) treated with vehicle or test compound. Two hours later, the same juvenile was presented to the same adult rat for another 5 min period, a time when normally the stimulus juvenile is no longer identified (i.e., the adult rat investigates the juvenile for the same amount of time as during the first presentation). Thus under the influence of a purported memory enhancing drug, the time spent in investigating the same juvenile is expected to be reduced. Two days later, a juvenile, different from the one used for the first exposure, was presented to the adult rat, 2 h after drug or vehicle administration. Any reduction in social exploration of this different juvenile is thus considered as reflecting a nonspecific effect of the drug (i.e., not memory related). On no occasion was a subject tested twice with the same juvenile stimulus animal, nor was a juvenile used more than once in a 48-hr period.

AF150(S) or AF267B (0.5, 1 and 5 mg/kg, p.o.) or vehicle, phosphate buffer saline (PBS) were administered to the adult rats immediately after the first exposure to the juvenile rat.

Time spent in social investigation of stimulus juvenile rat was measured (in sec) and then expressed for each animal as the ratio of the second exposure to the first exposure (Ratio of Investigation Duration (RID)). This transformation to RIDs was used in order to minimize possible individual as well as day-to-day variations in baseline performance (Perio et al Psychopharmacol. 97: 262-268. 1989). Therefore any reduction in investigation time during the second exposure will lead to a RID which is less than 1, indicating that the animal recognizes the juvenile rat. Analysis for repeated measurement was made by a 3-way ANOVA and post hoc comparisons were made by simple main effects contrasts analysis.

AF150(S) and AF267B decreased the investigation time of the same juvenile compared to placebo group in a dose-dependent manner. This improvement of memory cannot be attributed to non-specific effects, since it was not observed when a different juvenile was used for the second exposure. Both compounds thus appear to facilitate social memory in naive rats.

No significant difference was found between the total RIDs of the two compounds, but the interaction between similar/different juvenile x doses of both drugs was found statistically significant, $[F(3/33)=14.9, p<0.0001]$. Specifically, both compounds significantly reduced the investigatory time of the same juvenile at all three doses tested ($p<0.001$) relative to placebo. Furthermore, a significant difference was found between the RIDs of the 0.5 mg/kg and the two other doses ($p<0.05$); The RIDs observed for the 1 and 5 mg/kg were significantly lower than those observed for the 0.5 mg/kg.

It should be noted that a significant difference was found between the RIDs of the same juvenile group and a different juvenile group at all three doses ($p<0.01$-$p<0.001$).

EXAMPLE 46

Effects of AF267B and AF292 on Passive Avoidance (PA) in Cholinotoxin (AF64A)-Treated Rats The general procedure followed is described in Fisher et al., J. Pharmacol. Exptl. Therap., 257: 392, 1991. AF64A (10 mM) was prepared by alkaline hydrolysis of acetylethylcholine mustard.HCl. Rats, anesthesized with Equithesin (0.3 ml/100 g, IP) were injected bilaterally by stereotaxic application of AF64A (3 nmol/2 µl/slide) or saline (2 µl) into the lateral cerebral ventricles (AP=−0.8; L=±1.5 mm from bregma; and DV=−4.8 mm from skull surface). Infusions were made via a CMA 100 microinjection pump, through a 30-gauge injection cannula, at a constant rate of 0.25 µl/min. The cannula was left in place for 4 min after injection to allow diffusion of the solution into the ventricles. Compounds or phosphate-buffer-saline (PBS) were administered once, p.o., immediately after shock. Retention was tested 72 h after training.

A significant difference was found in the initial latency between all AF64A-injected rats (29.02±3.1 s) and all saline injected rats (20.55±1.95 s), $F(1/72)=5.13, p<0.05$. A statistical interaction was found between AF64A-injection x drug treatment, $F(3/72)=11.99, p<0.001$, in the retention latency. The retention latency of AF64A-injected rats treated with PBS (67.1±18.9 s) was significantly shorter (poorer memory) than that of saline-injected rats treated with PBS (455.3±55.1) ($p<0.001$, by simple main effects contrasts analysis).

The retention latencies of AF64A-injected rats treated with AF267B, 0.1 mg/kg (440.7±46.4 s), and AF292, 1 mg/kg (447±46.8 s), were significantly longer (better memory) than that of AF64A-injected rats treated with PBS ($p<0.001$, by simple main effects contrasts analysis). No significant difference was found between the retention latency of AF64A-rats treated with AF267B, 0.03 mg/kg (105.7±31.9 s), and that of AF64A-rats treated with PBS. No significant differences were found between the latencies of any of the saline-injected groups.

AF64A-injected rats demonstrated a clear impairment in retention of the PA task. The minimal effective dose of AF267B in attenuating AF64A-induced retention deficiencies is less than 0.1 mg/kg, p.o. Both AF267B, 0.1 mg/kg, and AF292, 1 mg/kg, in the PA task, are efficacious in improving AF64A-induced retention deficiencies, compared to AF64A-injected rats treated with PBS. The minimal effective dose of AF292 may be below 1 mg/kg, po.

EXAMPLE 47

Effects of AF267B Cognitive Impairments Induced by AF64A in Rats in the MWM Test.

AF64A or saline-injected (6 months old) Sprague-Dawley rats were tested in the Morris Water Maze (MWM) task. The paradigm used assesses spatial learning abilities in a reference memory regimen, and involves training (days 1-4), transfer test (Probe trial—day 4, 3 min following the last training trial) and reversal test (day 5).

At 4 months post-operation, each of the AF64A and saline groups of rats was randomly subdivided into four treatment subgroups (n=9): subgroups 1-3 were treated with AF267B in doses of 0.3, 1, and 3 mg/kg, po, in a volume of 10 ml/kg, whereas subgroup 4 (control group) was treated with the vehicle, phosphate-buffer saline, 10 mM (PBS) in the same volume. Drugs and PBS were administered once a day for 5 days before starting the behavioral testing, and then for the duration of the 5-day experiment, 30 min before testing.

The three measures, escape latency, path length and swimming speed were analyzed by MANOVA, followed by simple main effects contrast analysis.

Results: AF64A-injected rats showed a significantly longer escape latency than saline-injected rats, $F(1/64)=10.56, p<0.005$. In terms of path length, AF64A-injected rats showed a significantly slower learning curve than saline-injected rats, $F(3/192)=4.01, p<0.01$. AF267B had no significant effect on learning; however, AF64A-injected rats treated with AF267B-1 mg/kg showed a tendency for improvement, in escape latency only, while AF267B-3 mg/kg tended to impair performance in these rats. No correlation was found between the cognitive measures (escape latency and path length) and the nonspecific, motor measure (swimming speed).

All saline-injected rats showed a spatial bias in the probe trial, in both parameters, $F(3/192)=7.86, p<0.001$, and $F(3/192)=7.44, p<0.001$, for escape latency and path length, respectively. On the other hand, AF64A-injected rats treated with PBS showed only a partial spatial bias on this test. However, AF64A-injected rats treated with AF267B showed a complete spatial bias, similar to that of saline-injected rats, as presented in escape latency only, $F(9/192)=2.3, p<0.025$. No significant differences were found between the various doses of AF267B, in their beneficial effect on memory.

No significant differences were found between any of the groups tested in the reversal test. However, AF64A injection tended to deteriorate cognitive performance, in both measures. Additionally, AF64A-injected rats treated with AF267B-1 mg/kg showed a tendency for improvement, while AF64A-injected rats treated with AF267B-3 mg/kg showed a tendency for impairment on this test.

EXAMPLE 48

The Effects of AF150(S), AF267B, Rivastigmine and Nicotine on MWM Performance of C57BL/10SnJ vs. C57BL6J Mice C57BL/10SnJ (B10) mice were selected due to their small hippocampi and decreased number of hippocampal pyramidal neurons; the cell loss seemed to be associated with poor spatial learning. Deficiencies in spatial memory tasks observed in these animals were reported to be responsive to cholinergic manipulation (scopolamine) (Simons et al Life Sci., 42, 375-383, 1988), and both ACHE inhibitors (physostigmine) and muscarinic agonists (AF102B, PD151832) (Simons et al., 1988; Vincent et al Brain Res., 597, 264-268, 1992; Schwarz et al Drug Dev. Res., 40, 133-143, 1997) have shown positive effects in this model, using the MWM.

Each group of mice was randomly divided into 7 treatment groups (n=12-14/group). Groups 1-2 were treated with AF150(S) at doses of 0.5 and 1 mg/kg, i.p, in a volume of 10 m/kg, groups 3-4 were treated with AF267B at the same doses and volume, groups 5-6 were treated with rivastigmine and nicotine, respectively, at the dose of 1 mg/kg, i.p, and group 7 was treated with the solvent, saline 0.9%. All tested compounds and saline were administered once a day for 4 days before starting the behavioral testing, and then for the duration of the 5-day experiment, 30 minutes before testing.

Training: Each mouse was trained for four consecutive days, four trials (one block) per day, in which the platform position remained constant and was located in the center of the southeast quadrant of the pool. Within each block of four trials, each mouse started at each of the starting locations, but the sequence of locations was randomly selected. A trial consisted of placing a mouse by hand into the water facing the wall of the pool at one of four starting locations, north, south, east or west, around the pool's perimeter. Escape latency (the time to find the platform), path length (the distance traveled by the mouse) and speed (the swimming rate of the mouse) were recorded on each trial by the monitoring system.

For each mouse, the path length, escape latency, and swimming speed of the four trials on each of the 4 training days were grouped into blocks (one block for each day). The scores of all three measures were analyzed by a three-way MANOVA (2×7×4) with one repeated variable (days) and two non repeated variables [mice strain—C57BL/10SnJ or C57BL6J, and treatment—two doses of each, AF150(S) and AF267B, rivastigmine, nicotine (one dose for each) and saline]. Specific comparisons were performed, using the simple main effects contrasts analysis, which is specifically suited for testing significant interactions.

Escape latency. Small-hippocampi mice showed significantly longer escape latencies (indicating a worse RM performance) than normal hippocampus rats. AF150(S) and AF267B, and rivastigmine, positively affected the training performance of small hippocampus mice, $F(6/161)=6.39$, $p<0.0001$. Specifically, both doses of each of the muscarinic compounds improved the escape latencies of small hippocampus mice, compared to control group ($p<0.01$-$p<0.001$); Furthermore, AF267B showed a dose-response curve in its effect on performance ($p<0.02$) while AF150(S) affected performance equally by both doses. Both AF150(S) and AF267B affected performance more effectively than rivastigmine ($p<0.05$-$p<0.001$, respectively). AF150(S) increased the escape latencies of normal hippocampus mice, by both doses ($p<0.05$-$p<0.01$) whereas AF267B did not significantly affect the escape latencies of these mice during training. While nicotine had no improving effect of memory deficits shown by small hippocampus mice, it degraded the performance of normal hippocampus mice ($p<0.02$). The results also indicated a significant, general effect of training, $F(3/483)=90.49$, $p<0.0001$; the escape latencies of all groups decreased linearly during the four training days ($p<0.0001$, by a polynomial contrast).

Path length. Small hippocampi mice showed significantly longer path lengths than normal hippocampus mice, $F(6,161)$ 2.35, $p<0.033$. AF150(S) (both doses), AF267B (the higher dose) and rivastigmine positively affected the performance of small hippocampus mice ($p<0.05$-$p<0.01$). AF150(S) (only the higher dose) significantly ($p<0.05$) impaired the path length of normal hippocampus mice whereas neither AF267B nor rivastigmine had any effect on the path length of these mice. Nicotine had no significant effect on the performance of any of the mice strains tested. The results also indicated a significant general effect of training, $F(3/483)=86.98$, $p<0.0001$; the path lengths of all groups decreased linearly during the four training days ($p<0.0001$, by a polynomial contrast).

Swimming speed. Motor activity differences were observed between the two strains of mice treated with saline: The swimming speed of small hippocampus mice was significantly lower than that of normal hippocampus mice, $F(6/161)=14.32$, $p<0.0001$. Furthermore, both muscarinic drugs significantly increased the swimming speed of small hippocampus mice. Specifically, AF267B enhanced the swimming speed in a dose dependent manner ($p<0.001$, relative to control; $p<0.02$, between doses) while the enhancing effect of AF150(S) was equal in both doses ($p<0.001$). Moreover, AF267B-1 mg/kg significantly enhanced the swimming speed more strongly ($p<0.001$) than AF150(S)-1 mg/kg. Neither rivastigmine nor nicotine had any significant effect on the swimming speed of small hippocampus mice. AF150(S) significantly ($p<0.01$-$p<0.001$) impaired the swimming speed of normal hippocampus mice while AF267B had no such effect. Likewise, rivastigmine ($p<0.01$) and nicotine ($p<0.001$) significantly decreased the swimming speed of these mice. The results also indicated a significant general effect of training, $F(3/483)=15.34$, $p<0.0001$; the swimming speeds of all groups increased linearly during the four training days ($p<0.0001$), by a polinomial contrast).

Transfer test. During trial No. 17, on the fourth day, the platform was entirely removed from the pool (a probe trial). In this trial, the mouse was placed into the water for a limited period (30 s), and its spatial bias was measured by recording the relative distribution of escape latency and path length over the four quadrants of the pool. The path length and escape latency for the transfer trial (trial No. 17) were analyzed by a three-way MANOVA (2×7×4) with one repeated variable (quadrant in the pool) and two non repeated variables [mice strain—C57BL/10SnJ or C57BL6J, and treatment—two doses of each, AF150(S) and AF267B, rivastigmine and nicotine (one dose for each) and saline].

The three-way interaction for the escape latency measure was found statistically significant, $F(18/483)=1.62$, $p<0.05$, while the interaction for the path length measure was close to significance, $F(18/483)=1.5$, $p<0.08$. Normal hippocampus mice treated with saline showed a complete spatial bias in the transfer test. They spent significantly more time in the training quadrant ($p<0.001$) relative to the three other quadrants of the pool. On the other hand, small hippocampus mice treated with saline showed only a partial spatial bias in this test; They spent significantly more time in quadrant No. 1 relative to quadrants No. 3 ($p<0.001$) and 4 ($p<0.05$) but not relative to quadrant No. 2. However, small hippocampus mice treated with AF150(S) or AF267B (by both doses), or rivastigmine, showed a complete spatial bias, like normal hippocampus mice. In contrast, small hippocampus mice treated with nicotine showed only a partial spatial bias, like small hippocampus mice treated with saline. Normal hippocampus mice treated with AF150(S)-1 mg/kg showed only a partial spatial bias in the transfer test while all other normal hippocampus mice treated with the other drugs showed a complete spatial bias in this test. The results of the path length measure were very similar to those of the escape latency measure.

Reversal test. During trials 18-21, on the fifth day, the platform position was changed to the northwest quadrant, opposite to the training quadrant Thus, during reversal learning, the platform location was moved relative to the configuration of objects within the room, but the pool occupied the same place within the room throughout the entire experiment. Testing of the rats and measures taken were the same as in training.

For each mouse, the escape latency, path length and swimming speed of the reversal test (trials No. 18-21) were grouped into one block. All three measures were analyzed by a two-way MANOVA (2×7) with two variables ([mice strain—C57BL/10SnJ or C57BL6J, and treatment—two doses of each, AF150(S) and AF267B, rivastigmine, nicotine (one dose for each) and saline].

Escape latency. Small hippocampi mice showed significantly longer escape latencies during reversal learning than normal hippocampus mice, $F(6/161)=3.26$, $p<0.005$. Both muscarinic drugs, AF150(S) and AF267B (by both doses), significantly ($p<0.05$-$p<0.01$) improved the escape latency of small hippocampus mice while AF150(S)-0.5 mg/kg significantly ($p<0.05$) impaired the escape latency of normal hippocampus mice. Both rivastigmine and nicotine had no significant effect on either C57BL/10SnJ or C57BL6J mice.

Path length. The only significant effect ($p<0.05$) shown in this measure was the impairment of reversal learning by AF150(S)-1 mg/kg in normal hippocampus mice [$F(6/161)=2.85$, $p<0.011$, for the two-way interaction).

Swimming speed. No significant differences were obtained between the saline-treated, two strains of mice in motor activity. However, both muscarinic drugs, by both doses, significantly ($p<0.01$-$0.001$) increased the swimming speeds of small hippocampi mice, $F(6/161)=8.71$, $p<0.0001$. The swimming speeds of normal hippocampi mice were significantly decreased by AF150(S)0.5 mg/kg ($p<0.02$), AF267B-1 mg/kg ($p<0.05$), rivastigmine ($p<0.01$) and nicotine ($p<0.05$).

AF150(S), AF267B, and the ACHE inhibitor, rivastigmine, significantly attenuated these impairments in mice with small hippocampus. The improvement of cognitive functioning was more pronounced during acquisition and retention, although a similar improvement was shown by both muscarinic compounds in reversal learning. In contrast, nicotine had no beneficial effect on the cognitive performance of small hippocampi mice. A dose-response effect of AF267B was demonstrated in acquisition, by the differential improvement of the cognive deficits shown in escape latency measure. The beneficial effect of the 1 mg/kg dose was significantly stronger than that of the 0.5 mg/kg dose. During transfer trial, non-treated, small hippocampi mice showed only partial memory deficits concerning the platform location. A significant improvement of these deficits was demonstrated equally well by both muscarinic drugs, at the two doses tested, as well as by rivastigmine, but not by nicotine. The contribution of AF267B and AF150(S) to the improvement of learning and memory processes is emphasized by two findings: the dose-response effect shown by AF267B in acquisition, and the beneficial effect of both drugs demonstrated in the probe (transfer) trial. In this respect it should be noted that the probe trial is the foremost procedure in the MWM task, providing measures that quantify the strength and accuracy of the original learning.

EXAMPLE 49

AF150(S) is Effective in Restoration of Cognitive Impairments in Ischemic Rats.

Transient ischemia in rats was induced by a modification of the ischemia model (Voll et et al, Stroke, 20: 1700-1706, 1989). This was done by a bilateral carotid artery occlusion in Sprague Dawley rats: (42 male, 3 months old, weighing 270-340 g) combined with reduction in blood pressure induced by sodium nitropruside. Ischemia was induced in 21 rats whereas the other 21 rats served as sham controls. Under pentobarbital anasthesia (30 mg/kg, ip), sodium nitropruside 4.8 mg/kg/hr) was infused through a cannula implanted in the tail vein, for a period of 25 min. Five n after the initiation of the infusion, at the time when mean blood pressure was maintained at 30-60 mmHg (intial levels ~110 mm Hg) both carotid arteries were clamped for 20 min. Immediately afterwards 1.8 mEq sodium bicarbonate solution was administerd ip in order to minimize systemic acidosis. The sham operated rats were anesthetized as the ischemic rats and were infused with saline. Their carotid arteries were exposed but were not subject to carotid clamping. In rats subjected to ischemia, a mortality of about 30% was recorded within 24 hr after surgery. Animals were allowed to recover for 3 weeks prior to behavioral testing. Rats were randomly assigned to one of four groups: ischemic and sham-operated rats which were treated with AF150(S) (0.5 mg/kg, po) and ischemic and sham-operated control rats treated with double distilled water (DDW) (10 ml/kg, po). Each groups comprised of 10-11 rats. AF150(S) was administerd immediately following operation, once a day (6 days/week) for weeks before starting the behavioral testing, and then for the duration of the three-weeks experiment, 60 min before testing. The evaluation of the animals was done using the working-memory matching-to-sample paradigm in the MWM.

The ratio of escape latency (REL) and the ratio of path length (RPL) were calculated by the ratio of block no 2/block no 1 for each parameter. REL and RPL reflect the relative saving in performance from trial no 1 to trial no 2. REL and RPL were analyzed by a 3-way ANOVA (2×2×3), with one repeated variable (weeks) and two non-repeated variables (Operation-ischemia/sham-operated and Treatment-AF150(S)/DDW).

For both REL and RPL the interaction between operation x treatment was found statistically significant [$F(1/32)=8.08$; $p<0.01$ and $F(1/32)=6.75$; $p<0.025$, for REL and RPL, respectively). Simple main effects contrasts analysis showed that both REL and RPL of ischemic rats treated with DDW were higher than those of control rats treated with DDW ($p<0.01$ and $P<0.02$ for REL and RPL, respectively). This result indicates a deficit in working memory processes of ischemic rats compared to control rats.

AF150(S) significantly improved working memory performance of ischemic rats, compared with DDW-treatment; both REL and RPL of ischemic rats treated with AF150(S) were significantly lower ($p<0.05$) than those of ischemic rats treated with DDW. Control rats treated with AF150(S) did not show any significant change in performance. No differences in swimming speed were found in any of the tested groups. In concluson, chronic administration of AF150(S), 0.5 mg/kg, po, showed a clear improvement of working memory performance in ischemic rats during the three weeks of the experiment (following 3-6 weeks of drug administration). Nonspecific, motor coordination effects could explain neither the behavioral effects of the ischemic rats, nor the improving effects of AF150(S), because no significant effects were demonstrated in the swimming abilty of the rats in the Morris water maze testing.

EXAMPLE 50

Effects in Trihexyphenidyl Treated Rats—AF150(S), AF267B, AF292, AF704

Trihexyphenidyl is a selective M1 muscarinic antagonist that crosses the blood brain barrier and induces memory and learning impairments (Bymaster et al. J Pharmacol Exp Ther 267: 16-24, 1993. Roldan et al Neurosci. Lett. 230: 93-96, 1997; Kimura et al Brain Res. 834: 6-12, 1999).

Naive Wistar rats were used in the experiments below. The passive avoidance (PA) task is comprised of training (acquisition) phase and a retention phase. In the training procedure each rat was individually placed in the small illuminated compartment and after 60 sec. of familiarization/adaptation, the door to the large compartment was opened and the latency to enter was measured (Initial Latency). Immediately following entry into the dark compartment, the door was closed and inescapable foot shock (0.6 mA for 3 sec) was delivered through the grid floor. A cutoff point of 180 sec was used for initial latency. Animals that failed to enter (step-through) within 180 sec were excluded from the experiment. After the acquisition trial the rat was returned to its home cage. Retention of the passive avoidance task was measured 24 h later, by again placing the rat in the light compartment and after a 60 sec adaptation interval, the door was opened and the latency to renter the dark compartment was measured. A cutoff point of 300 sec was used for retention latency. Animals that failed to step through within 300 see were removed from the apparatus and a 300 sec latency was recorded for them.

The tested compounds include: AF150(S) (0.5, 1 and 5 mg/kg, p.o.), AF267B (0.5, 1 and 5 mg/kg, p.o.), AF102B 1 mg/kg, p.o.). The retention latency of trihexyphenidyl rats treated with AF150(S)-5 mg/kg (222±25.6), AF267B-0.5 mg/kg (181.1±35.4), AF267B-1 mg/kg (290.1±8.5) and AF102B-1 mg/kg (234.4±35.3) was significantly longer than that of trihexyphenidyl rats treated with double distilled water (DDW) (82.9±19.55) ($p<0.01$-$0.001$). Furthermore, the retention latency of the trihexyphenidyl rats treated with AF267B-1 mg/kg was significantly longer than that of trihexyphenidyl rats treated with AF267B-0.5 mg/kg ($p<0.01$) or trihexyphenidyl rats treated with AF150(S)-5 mg/kg ($<0.05$). No difference was found in the retention latency between control groups treated with various drugs or DDW. AF704 was also significantly effective in this test. Thus retention latency of trihexyphenidyl rats treated with DDW (116.25±36.36) was significantly shorter than that of control (DDW) rats treated with DDW (300±0) ($p<0.001$). However, the retention latency of trihexyphenidyl rats treated with AF704-0.1 mg/kg, po (214.70±36.63), 0.5 mg/kg, po (283.50±17.39) and 1 mg/kg, po (274.44±26.97) was significantly longer than that of trihexyphenidyl rats treated with DDW ($p<0.01$-$0.001$).

AF292 was the most potent compound among the tested agonists. AF292 was significantly effective at a dose of 0.1-0.05 mg/kg, po. When the lowest dose of AF292 0.03 mg/kg, po was tested after 24 and 72 hrs, only the 72 hrs delay showed a significant effect on PA in retention latency {225.9±36 vs. DDW—93.1±29.0; $p<0.01$ compared to trihexyphenidyl rats treated with DDW). No effects were found in the initial latency. These results show AF292 to be a highly potent agonist (e.g. more potent than AF150(S) by two orders of magnitudes), despite the higher potency of AF150(S) in binding studies against pirenzepine (high affinity & low affinity). This effect of AF292 cannot be attributted only to a higher bioavailability of AF292 vs AF150(S) in rats (49% vs. 31%).

EXAMPLE 51

Effects of AF267B, AF292 on Cognitive Function in Aged Rats.

Old (22-24 months old) and young (three months old) Sprague-Dawley rats had been tested in the MWM. Old rats showed a significantly slower learning curve than young rats, $F(3/267)=6.74$, $p<0.0001$, and $F(3/267)=4.66$, $p<0.003$, for escape latency and path length, respectively. No significant effect was found for any of the test compounds on learning, however, aged rats treated with AF267B-1 mg/kg showed a tendency for improvement. All young rats showed a spatial bias in the probe trial, in both parameters, relative to old rats, $F(3/267)=34.91$, $p<0.0001$, and $F(3/267)=9.06$, $p<0.0001$, for escape latency and path length, respectively. No significant effect was found for any of the test compounds on memory; however, relative to old rats treated with DDW, aged rats treated with AF292 in both doses, showed a tendency for partial spatial bias in this test Old rats showed significantly worse performance during reversal learning than young rats. AF267B-1 mg/kg improved significantly the reversal learning of aged rats, $F(4/88)=2.62$, $p<0.04$, and $F(4/88)=2.58$, $p<0.04$, for escape latency and path length, respectively. The beneficial effects of AF267B on reversal learning of old rats could not be attributed to non-specific, motor coordination effects, since AF267B had no significant effect on the swimming ability of these rats. AF292 did not reach significance in the reversal learning of aged rats, yet from the shape of the curves there is a tendency of improvement at both doses tested, 1 and 0.5 mg/kg, po.

EXAMPLE 52

CNS Safety Profile of AF292 (Table 1)

AF292 was evaluated in rodents for possible effects on general behavior and other GNS related pharmacological effects. No significant physical or behavioral signs were observed in rats administered AF292 at 1, 10, 30, 60, or 100 mg/kg orally, as compared to the vehicle control group. No behavioral or physical signs were observed 24 hours after administration. All rats were retained for 14 days, and throughout this retention period all rats appeared normal. In comparison, the compound AF267B begins to show some effects (salivation and lacrimation at about 40 mg/kg po) already in the first hour after admistration.

EXAMPLE 53

Cardiovascular Safety of AF292
1. Astemizole (human ether-a-go-go related gene (HERG) Channel) Binding Assay. AF292 was inactive in this binding assay as it failed to inhibit [$^3$H]-Astemizole binding to the hERG-encoded channel.
2. Isolated Guinea Pig Right Atrium (atrial fibrillation). AF292 had no significant effect on contractile force, but tended to slightly reduce the contractile rate beyond what is seen in the vehicle group.

3. Effects of AF292 (dose 5 mg/kg orally) on cardiac electrophysiological, cardio-haemodynamic in instrumented, awake dogs. Healthy trained and chronically instrumented female Beagle dogs of varying age and ranging in body weight from 9.4 to 12 kg, were used for recording of the cardiovascular parameters: heart rate, diastolic and systolic blood pressure, pressure rate product, LV dp/dt max, LV dp/dt max/pd, LV dp/dt min, cardiac output, stroke volume, systemic vascular resistance and the ECG parameters (PQ-, QRS-, QT-, QTcBazett—(QTcB), QTcFridericia—(QTcF) and QTcVan de Water—(QTcVdW) interval duration and QT-dispersion. During the last 18 hours prior to the experiments, the dogs had no access to food. Water was available ad libitum. At the beginning of each experiment, control values of the various parameters were recorded for at least 30 min. Thereafter, 5 mg/kg of AF292 (n=4) or the corresponding volume of the solvent (n=4) was administered orally by gavage. The various haemodynamic parameters were recorded continuously for 4 hours thereafter.

AF292 orally administered at a dose of 5 mg/kg has no statistically significant and relevant effect on hemodynamic or ECG parameters: e.g. blood pressure, cardiac contractility (LV dp/dt max; LV dp/dt max/pd) and relaxation (LV dp/dt min), stroke volume, systemic vascular resistance, the duration of the PQ-, QRS-, QT-, QTcB-, QTcF- and QTcVdW-interval, QT-dispersion and on ECG-morphology.

EXAMPLE 54

Effects of AF292 on Cytochrome P450 Isoform Inhibition

Cytochrome P450 activity can be an indicator for potential drug-drug interactions. AF292 was evaluated in a microtiter plate assay for P450 inhibition. AF292, at a concentration up to 10 μM, did not induce significant. inhibition of CYP1A2, CYP2C9, CYP2C19, CYP3A4 and CPY2D6 isoforms, five major human P450 enzymes responsible for drug metabolism and associated drug-drug interactions.

EXAMPLE 55

In vitro Metabolizm of AF292

The metabolic stability of AF292 was evaluated by monitoring its disappearance while incubated with rat, rog, monkey, and human hepatic microsomes. Testosterone, and propranolol were run as assay controls. The results are shown in Table 1.

EXAMPLE 56

Human Colon Adenocarcinoma (Caco-2) Cell Permeability Studies of AF292.

This test is used to determine intestinal permeability of tested compounds. Caco-2 cells, when grown on semipermeable filters, spontaneously differentiate in culture to form confluent monolayers which both structurally and functionally resemble the small intestinal epithelium. Because of this property they are useful as an in vitro model for the study of drug absorption and metabolism during absorption in the intestinal mucosa. Caco-2 monolayers were grown to confluence on collagen-coated, microporous, polycarbonate membranes in 12 well plates and permeability of the test material was determined. The average permeability coefficient ($P_{app}$) of AF292 was $17.4 \times 10^6$ cm/sec ranking it as having a high absorption potential (bidirectional assay performed).

EXAMPLE 57

Protein Binding

Protein binding studies were carried out in human plasma, $\alpha_1$-glycoprotein, human serum a (HSA), and Dulbecco's Phosphate Buffered Saline (PBS). AF292 was added to a final concentration of 10 μM. The results showed 0% protein binding in PBS buffer dose conc. (μM) and in human α-glycoprotein (AGP), (see Table 1).

EXAMPLE 58

Pharmacokinetic Profile of AF292 in Rats and Dogs

The results of the PK profile of AF292 in rats and Beagle dogs (overnight fasting; drug administered in water solution; gavage) are listed in Table 1.

EXAMPLE 59

Toxicology Profile of AF267B

AF267B has been extensively tested in chronic toxicity studies for up to 13 weeks in the Wistar rat and the Beagle dog. In the dog, the no-adverse-effect-level (NOAEL) is considered to be in the range of 6-9 mg/kg/day, po. Effects seen in the dog (>9 mg/kg) and rat (>40 mg/kg) are consistent with the profile of AF267B as a muscarinic agonist without toxic cardiovascular effects (tested in awake dogs). AF267B was evaluated extensively in beagle dogs for up to 13 weeks in oral toxicity studies and electrocardiograms (ECG) were routinely recorderd pre- and post-administration of the test agent. Heart rate, P wave duration & amplitude, P-Q, QRS, and QT intervals were measured and no changes in the ECG considered to be related to the adminstration of the test agent were observed.

EXAMPLE 60

Effects of AF267B on Rat Hippocampal Neurons Exposed to AD Fibrils as Followed by: Survival and Apoptosis: GSK-3β Activity: Cytoplasmic and Nuclear Stabilization of β-catenin: Cyclin D1 Expression This study was performed in rat hippocampal primary cell cultures using the methods described by Garrido J L et al. (FASEB J 2002; 16:1982).

AF267B does not affect the survival and morphology of hippocampal neurons at concentrations of 0.5-50 μM. However AF267B (10 μM) protects >90% the hippocampal neurons from Aβ1-40 (5 μM) that alone caused a 45% decrease in survival and in morphology. These protective effects of AF267B are mediated by M1 muscarinic receptors since these are blocked by pirenzepine (10 nM), an M1 antagonist. AF267B (100 μM) decreased GSK-3β activity by 60% in cultures of rat hippocampal neurons. In such a preparation 10 μM Aβ fibrils increased GSK-3β activity to 370% vs control (100%). Furthermore AF267B (10 μM) antagonized the effects of Aβ fibrils (10 μM) decreasing GSK-3β activity to the same of 150% vs. control. AF267B (10 μM) prevented Aβ1-40 (5 μM)-induced apoptosis to the control level. When cultured hippocampal neurons were exposed to Aβ1-40 (5 μM), soluble β-catenin was degraded and this degradation was prevented by AF267B (100 μM). In fact, AF267B increased soluble β-catenin level above control in a concentration dependent manner [e.g. 1 μM (100%) 10 μM (300%), 100 μM (350%)]. Aβ1-40 (S P decreased nuclear β-catenin (by 60%), an effect blocked by AF267B (1 μM (140% vs control). These protective effects of AF267B are mediated by M1 mAChR since these are blocked by pirenzepine (10 nM). The destabilizing effect of Aβ1-40 (5× in rat hippocampal neurons was shown by dendritic shrinkage detected by immunofluorescent stain The position of the nucleus was shown by c-jun antibody. AF267B protected the neurons and the cells have healthy neurites when treated with this M1 agonist. The effect of AF267B is M1 mAChR mediated since it is blocked by pirenzepine (10 nM). Finally AF267B has a protective effect (50% increase vs. control) against Aβ1-40 (5 μM)-induced decrease (40% vs. control) of cyclin D1, a target gene of the Wnt pathway. Again this effect of AF2671 is blocked by by pirenzepine (10 nM).

The results shown here indicate that AF267B protects neuronal cells as evaluated by MTT reduction, immunofluorescence of neurofilaments and apoptotic analysis.

As shown above, compounds used in embodiments of the present invention are low molecular compounds that are capable of crossing the blood brain barrier. Many of these compounds have additional beneficial effects including, inter alia, improvement of memory and learning in a variety of animal models that mimic various aspects of AD and other related disorders with an excellent safety margin.

Table 1 compares some of the results of tests on AF292 and AF267B.

TABLE 1

| EFFECT | AF292 | | AF267B | |
|---|---|---|---|---|
| Trihexyphenidyl-rats-Passive avoidance | 0.03, 0.05, 0.1, 0.3, 0.5 mg/kg, p.o. positive effects; MED</0.03 mg/kg, p.o. LONG DURATION OF ACTION | | 0.5, 1, 5 positive effects MED 0.1-0.5 mg/kg, p.o. | |
| CNS (rat): General Observation | IRWIN TEST@ 1, 10, 30, 60, 100 mg/kg, p.o. No effect on: motor activity {open field; vertical & horizontal screen; rotarod; locomotor ataxia; body posture & tone; tremors; twiches; paralysis; catalepsy} reflexes {righting; corneal; pinnal; extension; limb tone; flexor withdrawal; startle} excitation or sedation {convulsion clonic/tonic; opisthotonus; vocalization; C-tail; Straub tail; circling; stereotypies; sedation; hypnosis (sleep} eye condition {palpebral ptosis; lacrimation; chromodacryorrhea; enophtalamus; exophtalamus} skin condition {skin plasticity, piloerection, blanching (ear); hyperemia, cyanosis} various effects {salivation; diarrhea; diuresis; response to handling; abdominal constriction; rectal temp.; death} | | Mydriasis: 25 mg/kg, p.o. Salivation: 40 mg/kg, p.o. Lacrimation: 50 mg/kg, p.o. Hypothermia: 50 mg/kg, p.o. Gnawing; 50 mg/kg, p.o. Convulsion: 50 mg/kg, p.o. Sedation: 100 mg/kg, p.o. Chromodacryorrhea: 100 mg/kg, p.o. IRWIN TEST: 1, 10, 100 mg/kg, p.o. 1 & 10 no effect on gross behavior & physiological state. 100 mg/kg: abnormalities of carriage, apathy, decreased corneal reflex, diarrhea, reduced grooming, increased urination, salivation, lacrimation & chromodacryorrhea, reduced locomotor activity, passivity, decreased respiration, reduced startle response (onset: 0.5 hr; duration 3-6 hrs.). | |
| [$^3$PZ]; rat cortex; Ki, μM | 1.64 +/− 0.13 | | 3.74 +/− 0.59 | |
| [$^3$OXO-M]; rat cortex; Ki, uM | 0.57 +/− 0.15 | | 1.62 +/− 0.34 | |
| α-APPs secretion in cell cultures transfected with rat M1 mAChR (% of max CCh) | 100% Equipotent with AF267B & carbachol. (CCh), EC50 = 3 μM; Even though less efficacious on PI | | 100% | |
| MTT assay against Aβ 25-35 & H$_2$O$_2$ in cell cultures transfected with rat M1 mAChR | Equipotent with AF267B & CCh at 100 μM; Even though less efficacious on PI | | 100% | |
| PI turnover vs. CCh (as 100%) in cell cultures transfected with the human mAChR subtype | PI, AA: M1 mAChR: 35%, >88% PI., AA: M3 mAChR: Not active as agonist An M3 antagonist (pKb = 660 nM) M2 mAChR - no effects as agonist PI, AA: M5 mAChR - no effect as agonist PI, rat M1 mAChR; 50% | | PI, AA: M1 mAChR: 66%, 100% PI: M3 mAChR: 30% PI, rat M1 mAChR: 75% | |
| Metabolic Stability | Rat Liver Microsomes: T½ = 92 min Dog Liver Microsomes: T½ > 100 min Monkey Liver Microsomes: T½ = 74 min Human Liver Microsomes: T½ > 100 min {BETTER THAN AF267B} | | Liver Microsomes: T½ = 88 min Dog Liver Microsomes: T½ > 100 min Monkey Liver Microsomes: T½ = 27 min Human Liver Microsomes: T½ > 100 min | |
| Protein Binding | PBS = 0% Human α-glycoprotein (AGP) = 0% Human serum albumin (HSA) = 22% Human Plasma = 35% | | PBS = 0% AGP = 5.7% HSA = 32% Human Plasma = 25% | |
| Pharmacokinetic study^ | Rats, 10 mg/kg, p.o. | Dogs, 5 mg/kg. p.o. | Rats, 5 mg/kg, p.o. | Dogs., 1 mg/kg, p.o. |
| T½, hr | 0.99 | 2.04 | 0.64 | 1.33 |
| Tmax, hr | 0.5 | 0.8 | 0.25 | 0.58-0.75 |
| MRT, hr | 1.5 | 4.85 | 1 | 1.96 |
| Cmax, ng/ml | 1906 | 1193 | 852, 1704** | 257, 1085# |

TABLE 1-continued

| | | | | |
|---|---|---|---|---|
| AUC$_{(0-inf)}$, (ng * hr/ml) | 2146 | 4648 | 773, 1546** | 552, 2760# |
| Bioavailability (% F) | 49 | 70 | 30*** | 53 |

| Toxicokinetic study: 13 w* | | | |
|---|---|---|---|
| AUC(0-inf) ng * h/ml | F (1×): outlier, 3901-4840; M (1×): 1142-10932 | | F (1×): 985-3179; M (1×): 800-3691 |
| | F(13 w): 1866-12723; M(13 w): 1609-4170 | | F(13 w): 1033-4164; M(13 w): 1041-4471 |
| MRT (area) [h] | F (1×): outlier, 8.7-18.7; M(1×): 5-27.3 | | F (1×): 4.7-5.3; M (1×): 3.8-5 |
| | F(13 w): 5.1-33.7; M(13 w): 5-7.8 | | F(13 w): 3.6-5.2; M(13 w): 3.0-4.2 |
| Elimination half life [h] | Mean T½ (M) = 6.34 +/− 5.9; | | Mean T½ (M) = 2.1 +/− 0.6 |
| | Mean T½ (F) = 10.6 +/− 7.6 | | Mean T½ (F) = 3.3 +/− 1.5 |

*Dogs: AF267B {1.5, 3, 6 mg/kg, p.o.; single = 1× & for 13 weeks = 13 w}; (AF292 obtained from AF267B, in vivo); treatment by gavage ½ h after feeding; solid drug in capsule. Plasma levels of the drug are analyzed at various time points by LC-MS;
**extrapolated for 10 mg/kg;
***calculated for 2 mg/kg, po;
(extrapolated for 5 mg/kg). Oral and intravenous area under the concentration vs. time curve (AUC) were compared to determine the % biovailability (% F) by the following formula: Dose (IV) × AUC (oral)/Dose (oral) × AUC(IV).
A % F of over 30% generally suggests good bioavailability.
Cmax levels are equally important to determine if sufficient plasma levels are attained to produce the desired pharmacological effect and a value >1 μM is usually sufficient.
AUMC is the first statistical moment of the AUC and is used to calculate the mean residence time (MRT = AUMC/AUC) which is the average time the compound is in the animal.
The Cmax represents the maximum concentration observed, the Tmax is the time to reach that maximum concentration and the T½ is the calculated half-life of the compound in plasma (ln2×MRT).
Clearance is the volume of fluid (containing compound) from which compound is removed completely per unit time.
Rat and dogs were dosed intravenously (iv) and by oral gavage.
Plasma levels of the drug are analyzed at various time points by LC-MS-MS.
@Irwin, S. PSYCHOPHARM 13: 222-257, 1968.

The results shown in Table 1 indicate that AF267B and AF292 have the same affinity, but differing efficacy for mAChR subtypes.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

We claim:

1. A crystalline form of (S)-2-ethyl-8-methyl-1-thia-4,8-diaza-spiro[4.5]decane-3-one (AF267B) having the following properties: P2$_1$2$_1$2$_1$ (No 16) a=10.394 ((10) (α=90°), b=20.133 (2) (β=90°), c=5.856 (4) (γ=90°) Å, T=110K.

2. A crystalline form according to claim 1, further having the following properties: Volume=1224.2 (9) Å$^3$, Z=4, Fw=202.32, Calculated density, Dc=1.092 Mg/m$^3$, Absorption coefficient, μ=0.232 mm$^{-1}$.

3. A crystalline form of (S)-2-ethyl-8-methyl-1-thia-4,8-diaza-spiro[4.5]decane-3-one (AF267B) having the following configuration:

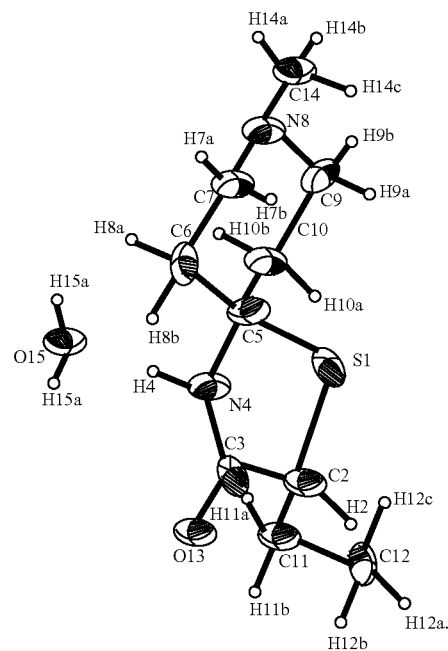

4. A pharmaceutical composition comprising a crystalline form according to claim 1, and a pharmaceutically acceptable carrier, diluent or excipient therefore, wherein said pharmaceutical composition is a powder, tablet, pill, capsule, cachet, suppository or a plurality of dispersible granules.

5. A pharmaceutical composition according to claim 4, wherein said pharmaceutical composition is in unit dosage form.

6. A pharmaceutical composition according to claim 5, wherein said pharmaceutical composition comprises between about 0.5 and about 100 mg of AF267B per unit dosage form.

7. A pharmaceutical composition according to claim 4, wherein said pharmaceutical composition is a powder, tablet, pill, capsule, cachet, or a plurality of dispersible granules.

8. A pharmaceutical composition comprising a crystalline form according to claim 2, and a pharmaceutically acceptable carrier, diluent or excipient therefor, wherein said pharmaceutical composition is a powder, tablet, pill, capsule, cachet, suppository or a plurality of dispersible granules.

9. A pharmaceutical composition according to claim 8, wherein said pharmaceutical composition is in unit dosage form.

10. A pharmaceutical composition according to claim 9, wherein said pharmaceutical composition comprises between about 0.5 and about 100 mg of AF267B per unit dosage form.

11. A pharmaceutical composition according to claim 8, wherein said pharmaceutical composition is a powder, tablet, pill, capsule, cachet, or a plurality of dispersible granules.

12. A pharmaceutical composition comprising a crystalline form according to claim 3, and a pharmaceutically acceptable carrier, diluent or excipient therefor, wherein said pharmaceutical composition is a powder, tablet, pill, capsule, cachet, suppository or a plurality of dispersible granules.

13. A pharmaceutical composition according to claim 12, wherein said pharmaceutical composition is in unit dosage form.

14. A pharmaceutical composition according to claim 13, wherein said pharmaceutical composition comprises between about 0.5 and about 100 mg of AF267B per unit dosage form.

15. A pharmaceutical composition according to claim 12, wherein said pharmaceutical composition is a powder, tablet, pill, capsule, cachet, or a plurality of dispersible granules.

16. A crystalline form of (S)-2ethyl-8-methyl-1-thia-4,8-diaza-spiro[4.5]decane-3-one (AF267B) monohydrate.

17. A pharmaceutical composition comprising a crystalline form according to claim 16, and a pharmaceutically acceptable carrier, diluent or excipient therefor, wherein said pharmaceutical composition is a powder, tablet, pill, capsule cachet, suppository or a plurality of dispersible granules.

18. A pharmaceutical composition according to claim 17, wherein said pharmaceutical composition is in unit dosage form.

19. A pharmaceutical composition according to claim 18, wherein said pharmaceutical composition comprises between about 0.5 and about 100 mg of AF267B per unit dosage form.

20. A pharmaceutical composition according to claim 17, wherein said pharmaceutical composition is a powder, tablet, pill, capsule, cachet, or a plurality of dispersible granules.

21. A crystalline monohydrate of (S)-2-ethyl-8-methyl-1-thia-4,8-diaza-spiro[4.5]decane-3-one (AF267B).

22. A pharmaceutical composition comprising a crystalline monohydrate according to claim 21, and a pharmaceutically acceptable carrier, diluent or excipient therefor, wherein said pharmaceutical composition is a powder, tablet, pill, capsule, cachet, suppository or a plurality of dispersible granules.

23. A pharmaceutical composition according to claim 22, wherein said pharmaceutical composition is in unit dosage form.

24. A pharmaceutical composition according to claim 21, wherein said pharmaceutical composition comprises between about 0.5 and about 100 mg of AF267B per unit dosage form.

25. A pharmaceutical composition according to claim 21, wherein said pharmaceutical composition is a powder, tablet, pill, capsule, cachet, or a plurality of dispersible granules.

* * * * *

UNITED STATES PATENT AND TRADEMARK OFFICE
CERTIFICATE OF CORRECTION

PATENT NO.         : 7,439,251 B2                                              Page 1 of 1
APPLICATION NO.    : 10/512673
DATED              : October 21, 2008
INVENTOR(S)        : Fisher et al.

It is certified that error appears in the above-identified patent and that said Letters Patent is hereby corrected as shown below:

On the Title page,

[*] Notice:   Subject to any disclaimer, the term of this patent is extended or adjusted under 35 U.S.C. 154(b) by (316) days Delete the phrase "by 316 days" and insert -- by 353 days --

Signed and Sealed this

Eighth Day of September, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,439,251 B2 | Page 1 of 1 |
| APPLICATION NO. | : 10/512673 | |
| DATED | : October 21, 2008 | |
| INVENTOR(S) | : Fisher et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 639 days.

Signed and Sealed this

Fifteenth Day of March, 2011

David J. Kappos
*Director of the United States Patent and Trademark Office*